US011946048B2

(12) United States Patent
Grunwald et al.

(10) Patent No.: US 11,946,048 B2
(45) Date of Patent: Apr. 2, 2024

(54) NON-HUMAN PAPILLOMAVIRUSES FOR GENE DELIVERY IN VITRO AND IN VIVO

(71) Applicant: Fraunhofer-Gesellschaft zur Förderung der angewandten Forschung e.V., Munich (DE)

(72) Inventors: Thomas Grunwald, Leipzig (DE); Lea Bayer, Leipzig (DE)

(73) Assignees: FRAUNHOFER-GESELLSCHAFT ZUR FÖRDERUNG DER ANGEWANDTEN FORSCHUNG E.V., Munich (DE); ANGEWANDTEN FORSCHUNG E.V., Munich (DE)

( * ) Notice: Subject to any disclaimer, the term of this patent is extended or adjusted under 35 U.S.C. 154(b) by 11 days.

(21) Appl. No.: 16/763,957

(22) PCT Filed: Nov. 13, 2018

(86) PCT No.: PCT/EP2018/081102
§ 371 (c)(1),
(2) Date: May 13, 2020

(87) PCT Pub. No.: WO2019/096796
PCT Pub. Date: May 23, 2019

(65) Prior Publication Data
US 2020/0385718 A1 Dec. 10, 2020

(30) Foreign Application Priority Data
Nov. 14, 2017 (DE) .................... 10 2017 220 276.9

(51) Int. Cl.
*C12N 15/113* (2010.01)
*A61K 38/16* (2006.01)
*A61K 47/66* (2017.01)
*C07K 14/005* (2006.01)

(52) U.S. Cl.
CPC .......... *C12N 15/113* (2013.01); *A61K 38/162* (2013.01); *A61K 47/66* (2017.08); *C07K 14/005* (2013.01); *C12N 2710/20022* (2013.01); *C12N 2710/20023* (2013.01); *C12N 2710/20042* (2013.01); *C12N 2710/20045* (2013.01); *C12N 2800/22* (2013.01)

(58) Field of Classification Search
CPC combination set(s) only.
See application file for complete search history.

(56) References Cited

U.S. PATENT DOCUMENTS

| 6,416,945 B1 | 7/2002 | McCarthy et al. |
| 6,991,795 B1 | 1/2006 | Lowe et al. |
| 7,205,126 B2 | 4/2007 | Qiao et al. |
| 8,326,547 B2 | 12/2012 | Liu et al. |

FOREIGN PATENT DOCUMENTS

| JP | 2017-528137 A | 9/2017 | |
| WO | WO 2011/039646 A2 | 4/2011 | |
| WO | WO-2011039646 A2 * | 4/2011 | ........... C07K 14/005 |
| WO | WO 2016/038625 A2 | 3/2016 | |
| WO | WO 2017/075399 A1 | 5/2017 | |
| WO | WO 2018/152505 A1 | 8/2018 | |
| WO | WO 2019/096796 A1 | 5/2019 | |

OTHER PUBLICATIONS

Pastrana et al. Cross-neutralization of cutaneous and mucosal Popillomavirus types with anti-sera to the amino terminus of L2. (2005) Virology; vol. 337; pp. 365-372 (Year: 2005).*
Buck, Christopher B., et al. "Efficient intracellular assembly of papillomaviral vectors." Journal of virology 78.2: 751-757. (Year: 2004).*
Richardson, Sarah M., et al. "Gene Design: rapid, automated design of multikilobase synthetic genes." Genome research 16.4: 550-556. (Year: 2006).*
Rector, Annabel, et al. "Ancient papillomavirus-host co-speciation in Felidae." Genome biology 8.4: 1-12. (Year: 2007).*
Fujita et al., "Applications of Engineered DNA-Binding Molecules Such as TAL Proteins and the CRISPR/Cas System in Biology Research", International Journal of Molecular Sciences, (2015); 16: 23143-23164.
Bayer et al., "Non-human Papillomaviruses for Gene Delivery in Vitro and in Vivo", PLOS One, (2018); 13(6): e0198996.
Buck et al., "Generation of HPV Pseudovirions Using Transfection and Their Use in Neutralization Assays", Methods in Molecular Medicine, (2005); 119: 445-462.
Cerqueira et al., "Efficient Production of Papillomavirus Gene Delivery Vectors in Defined In Vitro Reactions", Molecular Therapy: Methods & clinical development, (2017); 5: 165-179.
Gaj et al., "ZFN,TALEN and CRISPR/Cas-Based Methods for Genome Engineering", Trends in Biotechnology, (2013); 31(7): 397-405.
Grunwald et al., "Improvement of DNA Vaccination by Adjuvants and Sophisticated Delivery Devices: Vaccine-Platforms for the Battle against Infections Diseases", Clinical and Experimental Vaccine Research, (2015); 4: 1-10.

(Continued)

*Primary Examiner* — Arthur S Leonard
*Assistant Examiner* — Josephine M Gonzales
(74) *Attorney, Agent, or Firm* — Knobbe, Martens, Olson & Bear LLP

(57) ABSTRACT

A non-human papilloma pseudovirus or virus like particle has at least one papilloma capsid protein codon-optimized for expression in eukaryotic cells or cell lines. A pharmaceutical composition includes the non-human papilloma pseudovirus or virus like particle, and a diagnostic agent, an imaging agent, and a therapeutic agent. A non-human papilloma pseudovirus or virus like particle can be used as a medicament. A method for producing a non-human papilloma pseudovirus or virus like particle involves codon-optimizing of capsid proteins of non-human papillomaviruses for expression in eukaryotic cells, synthesizing of the sequences and cloning of the synthesized sequences into expression vectors, and producing non-human papilloma pseudovirus or virus like particles. ι-carrageenan can be used as transduction enhancer for non-human papilloma pseudovirus or virus like particles in vitro.

6 Claims, 4 Drawing Sheets
Specification includes a Sequence Listing.

(56) References Cited

OTHER PUBLICATIONS

Grunwald et al., "Novel Vaccine Regimen Elicits Strong Airway Immune Responses and Control of Respiratory Syncytial Virus in Nonhuman primates", Journal of Virology, (2014); 88(8): 3997-4007.
Haas et al., "Codon Usage Limitation in the Expression of HIV-1 Envelope Glycoprotein", Current Biology, (1996); 6(3): 315-324.
Harms et al., "Mouse Genome Editing using CRISPR/ Cas System", Current Protocols in Human Genetics, (2014); 83: 15.7.1-15.7.27.
Herbst et al., "Genomic Characterization of Two Novel Reptilian Papillomaviruses, Chelonia Mydas Papillomavirus 1 and Caretta Caretta Papillomavirus 1", Virology, (2009); 383: 131-135.
Kines et al., "Human Papillomavirus Capsids Preferentially Bind and Infect Tumor Cells", International Journal of Cancer, (2016); 138: 901-911.
Kohlmann et al., "Protective Efficacy and Immunogenicity of an Adenoviral Vector Vaccine Encoding the Codon-Optimized F Protein of Respiratory Syncytial Virus", Journal of Virology, (2009); 83: 12601-12610.
Morton et al., "Structural Characterization of Respiratory Syncytial Virus Fusion Inhibitor Escape Mutants: Homology Model of the F Protein and a Syncytium Formation Assay", Virology, (2003); 311: 275-288.
Pastrana et al., "Cross-Neutralization of Cutaneous and Mucosal Papillomavirus Types with Anti-Sera to the Amino Terminus of L2", Virology, (2005); 337: 365-372.
Rao et al., "Expression of Codon Optimized Major Capsid Protein (L1) of Human Papillomavirus Type 16 and 18 in Pichia Pastoris; Purification and Characterization of the Virus-like Particles", Vaccine, (2011); 29 (43): 7326-7334.
Rector et al., "Animal Papillomaviruses", Virology, (2013); 445, 213-223.
Ternette et al., "Immunogenicity and Efficacy of Codon Optimized DNA Vaccines Encoding the F-Protein of Respiratory Syncytial Virus", Vaccine, (2007); 25: 7271-7279.
Ternette et al., "Expression of RNA Virus Proteins by RNA Polymerase II Dependent Expression Plasmids is Hindered at Multiple Steps", Virology Journal, (2007); 4(51): 10.1186.
Vinzon et al., "Protective Vaccination against Papillomavirus-Induced Skin Tumors under Immunocompetent and Immunosuppressive Conditions: A Preclinical Study Using a Natural Outbred Animal Model", PLOS Pathogens, (2014); 10(2): e1003924.
Wagner et al., "Rev-Independent Expression of Synthetic Gag-Pol Genes of Human Immunodeficiency Virus Type 1 and Simian Immunodeficiency Virus: Implications for the Safety of Lentiviral Vectors", Human Gene Therapy, (2000); 11: 2403-2413.
Zhao et al., "Disassembly and Reassembly of Human Papillomavirus Virus-Like Particles Produces More Virion-Like Antibody Reactivity", Virology Journal, (2012); 9(52); 1-13.
International Search Report; PCT/EP2018/081102, filed on Nov. 13, 2018, dated Feb. 25, 2019.
Bayer, L., et al., Non-Human Papillomaviruses for Gene Delivery In Vitro and In Vivo, PLOS One, vol. 13, No. 6, e0198996, 2018.
International Preliminary Report on Patentability, dated May 19, 2020, International Application No. PCT/EP2018/081102.
International Search Report & Written Opinion, dated Feb. 25, 2019, in International Application No. PCT/EP2018/081102.
Kines, R.C., et al., Human Papillomavirus Capsids Preferentially Bind and Infect Tumor Cells, International Journal of Cancer, vol. 138, No. 4, pp. 901-911, 2016.
Pastrana, D.V., et al., Cross-neutralization of cutaneous and mucosal Papillomavirus types with anti-sera to the amino terminus of L2, Virology, vol. 337, pp. 365-372, 2005.
Vinzon, S.E., et al., Protective Vaccination Against Papillomavirus-Induced Skin Tumors Under Immunocompetent and Immunosuppressive Conditions: A Preclinical Study Using A Natural Outbred Animal Model, PLoS Pathogens, vol. 10, No. 2, e1003924, 13 pages, 2014.
Buck et al., Efficient Intracellular Assembly of Papillomaviral Vectors, Journal of Virology, vol. 78, No. 2, pp. 751-757, 2004.
Buck et al., Carrageenan Is a Potent Inhibitor of Papillomavirus Infection, PLoS Pathogens, vol. 2, Issue 7, e69, pp. 0671-0680, 2006.
Graham et al., Mucosal delivery of human papillomavirus pseudovirus-encapsidated plasmids improves the potency of DNA vaccination, Mucosal immunology, vol. 3, No. 5, pp. 475-486, 2010.
Horvath et al., CRISPR/Cas, the immune system of bacteria and archaea, Science, vol. 327, pp. 167-170, 2010.
Kines et al., Vaccination with Human Papillomavirus Pseudovirus-Encapsidated Plasmids Targeted to Skin Using Microneedles, PLoS One, pp. 1-18, 2015, e0120797.
Lathe, R., Synthetic Oligonucleotide Probes Deduced from Amino Acid Sequence Data, J. Mol. Biol., vol. 183, pp. 1-12, 1985.
Office Action dated Sep. 6, 2022 in JP Application No. 2020-544150 in 9 pages.
Final Rejection dated Apr. 4, 2023 in Japanese Application No. JP 2020-544150.
Rector et al., Animal papillomaviruses, Virology, vol. 445, Nos. 1-2, pp. 213-223, 2013.

* cited by examiner

A

B

SEQUENCE LISTING

```
<160> NUMBER OF SEQ ID NOS: 40

<210> SEQ ID NO 1
<211> LENGTH: 1485
<212> TYPE: DNA
<213> ORGANISM: Artificial Sequence
<220> FEATURE:
<223> OTHER INFORMATION: CcPV1_L1

<400> SEQUENCE: 1
atggccgtgt ggaccctag caccaaggcc ctgtttgtgc ccccgtgaa tgtgcccacc      60 ctgtacagca cccgggaata cgtgcggcgg accagctatg tgttccacgg caccaccgag     120
cggctgatca ccatcggcaa ccctacttc gccctgaccg acaacgccac cgtgaccgtg     180
cctaaggtgt ccgcctacca gcaccgggtg ttccggatca agctgcccga ccccaacaag     240
ttccccatcc ctgaaagcgc cgtgggcgac agagacacca ccagacttgt gtgggccgtg     300
cggggcatcc aagtgaacaa gtctcagcct ctgggcgtgg gcgccagcgg caacaccatg     360
tttaacggcc tgcaggactt cgccgagaca caccacccca gcatggaaaa gcccgaccct     420
cccgaggaca gaagagtgaa cgccgccttc gacgccaagc agagccaggc actgatcgtg     480
ggctgcatcc ctcctgtggg ccagcattgg gatgccgcca agagatgcgt ggaagataac     540
```

```
aacaaggaca tgtgccctcc actggaactg cagcacaccg tgatcgagga cggcgacatg    600
atcgacatgg gcatgggcac cctgaacttc aagagcctga gcctgaactg gtccaccctg    660
cccctggaac tgatcaacag cgtgtccaag tacccgact  ggctgaccat gaacgccgac    720
ccctacggca accactgctt cttcatgctg aagcgggaac aggtgtacat gaagggcgtg    780
ggactgcacc tgggcaacat cggcgaggat gagcccacca ccatgttccg aagggcacc     840 acaggccaga agtaccagac ccccggcaga cacagctggt ccctctgct  gagcggcagc    900 ctgagcacca gcgacaatca gctgttcaac cggccctact ggctggaaaa cagcaccgcc    960
cccaacgacg gcatctgctg gcacaaccag atgttcgtga cctgcgtgga caccacccgg   1020
aataccatct tccagatcag ccagttcaag aaaggcgtga ccgccaccgc cgactacaaa   1080
gaggccaact acgatatgta cgcccggcac gtggaagagt acgagatcag cttcatcctg   1140
cagctgtgca gcatcaagat ggacctgccc gtgctgaacc atctgcacaa catggacgcc   1200
agcctgctgg acgattgggg ctttggagcc acccccctc  agaacctgac tgtggaagat   1260
cagtaccggt tcctgaacag caaggccacc aagtgcccac ctccaccagc cacaccagcc   1320
gatgctgatc cctggggcaa gtacaagttc tgggacgtgg actgtaccgc ccagatctcc   1380
agcgacctga ccccctttcc tctgggacgg cggttccagc agctgtatcc tcaggccgga   1440
aagcctgccc ccagcaaccc tagaaagcgg cggagaggca gatga                   1485
```

<210> SEQ ID NO 2
<211> LENGTH: 1359
<212> TYPE: DNA
<213> ORGANISM: Artificial Sequence
<220> FEATURE:
<223> OTHER INFORMATION: CcPV1_L2

<400> SEQUENCE: 2

```
atgatgagca gcggcggag  agtgaccaga gccagccccg atgacatttg gcggcactgc     60
aagcagttcg gcgactgccc cgacgacatc cagaaggtgt acacaggcaa cacaatcgcc    120
gacaacatcc tgaagtgggc cagcagcttc ctgttcttcg gcggcctggg aatcggatct    180
gccgaaggcg ctgtggccgc tgccgcctct gaacacatcc tgcctatcgg cggaggcagc    240
ctgcccaagc agcctatcga tgtgcccatc accagagtgc cgccagcaa  tgtgaccccc    300 ggcttcagcg acatcaccgt gaaccctgac gtggccctgg atgccggaac agtggtgcat    360
gccgccgaac ctgtggatcc tgtgtctggc acccccccca tcattcacgc cagccccaat    420
agcaccgaag tgatccccc  tatccggccc gtggaaaacc cccctggca  gaacccttc     480 gacagcggcc tggaaacccc aggcgtgaac gtgggcgtgg tggattacag cgccggcaac    540
gagatcgagc tgagcgtgct gtctagcacc gcccctaccc tgaccaacgc cgtggaagag    600
acagagctgt tcagcagatt cgagctggac cccagaacca gcacccccaa caccacaaca    660
agaggcggct ggatgtccca cgtggccgtg ggcagatttg ccaagacagc cgccagagaa    720
gtgcccctgc ctgtgctgac atctaccggc ggagtgatgc agttcgagaa ccccgccttc    780
gagttcagcg aggccgtgtc cgaggtgtcc cggtccatca gcttcaacga ccccgacagc    840
gccccctttc gccagactgt ctagacccagc ctgttccaga gagccggcag actgggagtg    900
cagagagtgg gcaatctgct gggcatggtc accagggccg gcaagcagct gttcgtgccc    960
cgggtgtact acaacgagct gtccagcatc ttcgagagcc ccgacgtgct ggaaatggaa   1020
cccatcatca tcgaggacag cggacccccc atcgaggatg aggctattcc tggcgctcct   1080
```

```
gccggcgtgt tcccacaggg caatagaccc tacgcctaca acggctacct gttcggcccc      1140
atccccgtgg acgtgtccat caaggtgtcc ggcaccggct tcatccccat gcctgtgacc      1200
gtgtccggaa acaccatctt cccactgtac cccagcttcg acaagagcac cccctgtac       1260 cccccagac acgtgttctt ctccgacctg gacgaccca tcatgttcaa gcggagaaag        1320
aagtgcttcg ccgacggctg cgtggacgcc ttctactga                             1359
```

<210> SEQ ID NO 3
<211> LENGTH: 1521
<212> TYPE: DNA
<213> ORGANISM: Artificial Sequence
<220> FEATURE:
<223> OTHER INFORMATION: CcrPV1_L1

<400> SEQUENCE: 3

```
atggctgtgt ggctgccgc ccagaacaag ttctacctgc cccctcagcc cagcaccaga       60
gtgctgagca ccgacgagta cgtgacccgg accagcatct tctaccacgc cagcaccgac      120
cggctgctga cagtgggcca cccctacttc gacatctacc acgagaacaa gaaagacatc      180
atcgtgccca aggtgtcccc caacgcctac cgggtgttca gactgaagct gcccgacccc      240
aacaacttcg ccttcggcga caagagcatc ttcgaccccg agaagaacg gctcgtgtgg       300 gccctgagag gcgtggaaat cgacagaggc cagcctctgg gctgtggcat cacaggccac      360
cccatcttca caagttcgc cgacgtggaa acgccaaga acgtgggcac cggccacgac        420
gccatgaatg ccatcggcag caacaccgcc ttcgacccta gcagaccca gatgttcctg       480 atcggctgca agcctgccct gggcgagcat tggtctagag ccgcctggtg caagaacaac      540
gagggcggag gactgggcca aaggacacc gattgccccc catcgagct gaaaaccacc        600 agcatcgagg acggcgacat ggtggacatc ggcttcggcg ccatggactt caacgacctg      660
cagcaggaca agaccagcgt gcccctggac atctacaaga gcaagtgcaa gtaccccgac      720
tacatcaaga tggccaacga ccccctacggc gacttctgct tcttctacgt gcggcgcgag     780
cagatgtacg cccggcacta cttcaccaga tacggcaaga tcagcgagaa agagcagggc     840 gacacccctgg aagatgacaa cccccccctg tccaccaaca actactttac cagccccagc     900
ggcagcctgg tgtctagcga gggccagctg ttcaaccggc cctattggat ccagcggagc      960
cagggccaga caacggaat cgcctggaac aatcagctgt cctgaccgt ggtgacaac         1020 accagaggca ccgccctgaa tatcatcgtg gccagaatg caccccaa ccagggcgcc         1080 ttcaaggcca acgagtacta cacctacctg cggcacgtgg aagagttcga catcagcgtg      1140
atcctgcagc tgtgcaaagt gcggctgacc cccgagaacc tggccatcat ccacaccatg      1200
gaccctaaca tcatcgaggc ctggcaccctg aacgtgaacc cccttccgg catcctggac      1260 gagacatacc ggtacatcca ctctatggcc accaagtgcc ccagcaacgt gccccccagc      1320
gaaaaagagg acccctacag caagctgaag ttctgggagg tggacctgcg ggacagactg      1380
accgagcagc tggatcagac ccccctgggc cggaagttcc tgttccagac caacgtgatc      1440
agaggcggcg tgaagcggcc cagagttgtg accacaagca gcaaggccaa gcccgtgaag      1500
agaaggcggg gcaacaaatg a                                                 1521
```

<210> SEQ ID NO 4
<211> LENGTH: 1605
<212> TYPE: DNA
<213> ORGANISM: Artificial Sequence
<220> FEATURE:
<223> OTHER INFORMATION: CcrPV1_L2

<400> SEQUENCE: 4

```
atgcacgcca gacggaaaag agccgcccct aaggacatct accccagctg caagatcagc        60
aacaactgcc ccgacgacat ccggaacaag atcgagcaca cacccctggc cgacaagatc       120
ctgaagtggg gctctgccgg cgtgttcttt ggctctctgg catcggcac cggcagaggc        180
acaggctctt atgtgccact gggcagcggc gtgaacgtgg caccagagt gtctaccgtg        240
aagcccagca tccccatcag cagcgtgggc acagccgacg tgatcccgt ggacgccatg        300
aatcctctgg gacctgctct ggcccctccc aagtttccta ccgccgtgga gatcccgtg        360
atcatcagac cccccaagtt ccccagcatt gtggaagatc ctgtgattgt gcacagcgcc       420
gctgagcacc ctgccgtgct ggaccctgat acattgccg tggtggacat cagcggcgag        480
acagtgcagg aaatccccta caccaccagc aacgtcgtga ccgaggaaca gcccgctgtg       540
ctggacgtgt ccaccgagac aagagccccc aagatcatca gccggaccca gtacgagaac       600
cccagcttcg aggtggccat cacctccaat gccacagccg cgaaaccag cgccaccgac        660
cacatcctgg tggacggcta ttctggcggc cagcacatcg gcgagcagat cgagctgcag       720
gaactggcca cacggtcctt cagcaccacc atcgaggaag aaaccagctt cctgaccagc       780
acccccaacg aagctgtcgt gcggcccaag accggaacc tgaacagcag aagatacctg        840
cagacccaag tgaccgaccc cgccttcgtg acccagccta aagcctcgt gaccttccag        900
aaccctgcct tcgacgagag cgtggacctg atcttcgaga aggacgtggc cgacttcccc       960
ctggccgctc ctaacgagga cttccgcgat ctgatcagcc tgagcaagcc catctaccac      1020
cggtccaacg agaacaccgt gcgggtgtcc agattcggca ccaaggccag cgtgaaaacc      1080
agatccggcg tgatcgccgg accccagatc cactacttct acgacctgag cgagatcgcc      1140
cctgccgaca acatcgagct ggccacactg gctctagcc ctgtgggaga gcagagcgga       1200
gagagcgtga tctctagcgg caccaccgac atggaaatca tctccctgac cggcagcacc      1260
ctggaaagct actccgatga gagcctgctg gatatctacg agcctatcgc caacgacctg      1320
cagctcgtga tcggcatcgg aagaagagtg cggcctatca gcgtgcccga cctgctgacc      1380
accaagttcc agatcttccc tggcttcgag ggcgtgcacg tgcacaccag cagcagcaac      1440
gagacaccca agatccctat caaccccctg gaaaccccag ccgtcgtgat tgatctgctg      1500
ggcggcaccg acttctacct gcaccccgcc ctgttcaaga agaagaaaaa gcggctgttc      1560
tgcgacttct cgccgacgg cggagtggcc tcctgcaccg aatga                      1605
```

<210> SEQ ID NO 5
<211> LENGTH: 1521
<212> TYPE: DNA
<213> ORGANISM: Artificial Sequence
<220> FEATURE:
<223> OTHER INFORMATION: CgPV1_L1

<400> SEQUENCE: 5

```
atggctatgt ggcggcccag cgacaacaag gtgttcctgc ctcctgccac ccccgtgtcc        60
aaggtgctga gcaccgacga ctacgtgtcc cggaccacca tctactacta cgccggcagc       120
agcagactgc tgaccgtggg ccaccctac ttccccatca gaagtccgg cggcagaaac         180
agcctgctgg tgcctaaggt gtccggctac cagtaccggg tgttcagagt gcggctgccc       240
gaccccaaca gttcggact gcctgagggc agcctgtaca ccccgagac acagagactt          300
gtgtgggcct gcagaggcgt ggaagtgggc agaggacagc ctctgggcgt gggcacatct       360
```

```
ggccaccctc tgagcatcga cctggaagat accaagaaca gcaccctgtt cgatggcgcc    420
cctggcaacg acagcagaga caacgtgtcc atggattaca agcagaccca gctgttcatc    480
atcggctgca agcccccact gggagagcac tgggctaagg cacccctg caatagcagc      540 accgtgaacg ccggcgattg cccacctctg gaactggcca gcaccaccat ccaggacggc    600
gacatggtgg ataccggctt cggcgccatg gatttcgccg ccctgcagag caacaagagc    660
gacgtgcccc tggacatcct gaacgccaca tgcaagtacc ccgactacct gcagatggcc    720
gccgagccct acggcgacaa gatgttctt t agcctgcggc gcgagcagat gttcgtgcgg    780
cacttctaca cagagccgg caccatgggc gagagcgtgc ccgaggaact gatcctgaaa     840 ggcgcccta gcagctccag agccacacct ggcagctcca tctacgccag cacacccagc     900
ggcagcatgg tgtctagcga gagccagctg tttaacaagc cctactggct gcagcgggcc    960
cagggaagaa acaacggcat ctgctggggc aatcaggtgt tcctgaccgt ggtggacacc   1020
acccggtcca ccaatctgac cgtgtgtgcc acagccacca gcgagacaac ctacaaggcc   1080
agcaacttca aagagtacct gcggcacggc gaggaattcg acctgcagtt catcttccag   1140
ctgtgcgtcg tgaacctgac cgccgaagtg atgacctaca tccacggcat ggacccatcc   1200
ctgctggaag attggaactt cggcaccctg ccccctccaa gcgcctctct gggcgatacc   1260
taccggttcc tgcagtccca ggccatcacc tgtcagaggc ctccagcccc cgagaaggac   1320
aagcaggatc cttacgccgg cctgaccttc tgggaggtgg acctgaccga gcggttcagc   1380
gtggacctgg accagttccc cctgggcaga aagttcctgc tgcagacagg cggcagacct   1440
agagccgccc tgccagcag aaaaagaaca gccgctcctg ccgctgcccc tgcccacaag    1500
agaaaaaaga ccaagagatg a                                             1521

<210> SEQ ID NO 6
<211> LENGTH: 1401
<212> TYPE: DNA
<213> ORGANISM: Artificial Sequence
<220> FEATURE:
<223> OTHER INFORMATION: CgPV1_L2

<400> SEQUENCE: 6
atggtggcca gagccagaag aagaaagcgg gccagcgcca cccagctgta ccagacctgt     60
aaagccgccg gaacctgccc ccctgacatc atccctaaga tcgagcacag caccgtggcc    120
gacaacatcc tgaagtacgg cagcctgggc atcttcctgg gcggcctggg aatcggcaca    180
ggctctggaa caggcggcag aaccggctac atccccgtgg gctctagacc ccctaccgtg    240
gtggatgtgg acccgtggc tagacctccc gtcgtgattg aacctgtggg cgccagcgac     300
cccagcatcg tgacactggt ggaagatagc agcatcatcc aggctggcgc cgctcacccc    360
aatttcacag gcagcggcgg cttcgaagtg accaccagcg gcacaacaac ccctgccgtg    420
ctggatatca caccagctgg cggcggagtg cagatcagca gcagctcctt cagcaacccc    480
ctgttcaccg agccccagtt cgtggaagct ccccagaccg cgaagtgtc cggccacatc    540 ctgatcagca cccctacaag cggcgctcac ggctacgaag agatccccat ggtcaccttc    600
gctcaggaag gctccggcct ggaacccatc agctctacac ctctgcctgg cgtgcgcgaga   660 ctggccggac ctagactgta cagcagagcc taccagcaag tgcgggtgga cgaccctcag    720
ttcgtgtctc agcctgccac cttcgtgacc tacgacaacc ccgtgtacga ccccgaggaa   780
accatcctgt cgaccggac cggcctgcac gatccccccg atcctgactt cctggacatc   840
gtggccctgc acagacctgc cctgagagcc acaagacagg gcagcgtgcg gttcagcaga   900
```

```
ctgggcagaa gggccaccct gagaaccaga agcggcaaga ccatcggcgc cagagtgcac      960
ttctaccacg acctgagccc catctctgcc gccgacaata tcgagctgca gccctgctg      1020 cccgtggatc cttctggcgt gacacccgac gagcctgtgt acgacatctt cgccgacccc    1080
gatgccctgc agcaggctgc tccaagccag agaagcagcc tgagcgtgta cagacccagc    1140
gtggtggccc tgtccgccac aagctctcac cctagcaccg tgcctctgtc tgctggcgtg    1200
gacgcccctg tgtttagcgg ccctgatgtg gatatccctg cgcctctcc atggcctcag     1260 ccagtgcctc ctcacaccac accccagcac agcatctacg tgcacggcac cgacttctac    1320
ctgctgccag gctacctgtt cgtgcccaag cggcggaagc ggttcatcta cagcttcgcc    1380
gatggctacg tggccgcctg a                                              1401
```

<210> SEQ ID NO 7
<211> LENGTH: 1491
<212> TYPE: DNA
<213> ORGANISM: Artificial Sequence
<220> FEATURE:
<223> OTHER INFORMATION: MfPV6_L1

<400> SEQUENCE: 7

```
atgagcctgt ggcggcccag cgacagcaag gtgtacctgc ctcctgcccc cgtgtccaag     60
gtggtgtcca ccgatgagta cgtgacccgg accagcatct actaccacgc cgccagctct    120
agactgctgg ccgtgggcca cccttactac gccgtgaaga aaggcaacaa agtgaccgtg    180
cctaaggtgt ccggcctgca gtaccgggtg ttcagagtgc ggctgcccga ccccaacaag    240
ttcggactgc ccgatgccaa cttctacgac cccaataccc agcggctcgt gtgggcctgt    300
atcggcctgg aagtgggcag aggacagcct ctgggcgtgg gcatctctgg acacccctg    360 ctgaacaagc tggacgacac cgagaacggc cccaaggtgg cagctggaca gggcgtggac    420
aaccgcgagt gcgtgtccat ggattacaag cagacccagc tgtgcctgct gggctgcaag    480
cctcctgtgg gagagcactg gggcaagggc aatccttgct ctgccggaaa cgccggcgat    540
tgccctccac tggaactgca gaacagcgtg atccaggacg gcgacatggt ggatacaggc    600 tacgcgcca tggacttcag cgtgctgcag gccaacaagt gcgacgtgcc cctggacatc    660
tgcaacagcg tgtgcaagta cccccgactac ctgaagatgg ccgccgagcc ctacggcgac    720
agcctgttct tttacctgcg cgcgcagcag atgttcgccc ggcacatgtt caacagagcc    780
ggcaacattg gcgacgccgt gcccgacgag ctgtacatca gggctctgg acagaaggcc     840 gccctgccca gccacatatt cttccccaaca ccctccggca gcatggtcac ctctgaggcc    900 cagctgtttta caagcccta ctggctgcag cgggcccagg ccacaacaa tggcatctgc     960 tggggcaacc aggtgttcct gaccgtggtg gacacaaccc ggtccaccaa catgaccctg    1020
tgtgccgcca ccggcaccga cagcacctac aagaacgaga acttcaaaga gtacatgcgg    1080
cacgtggaag agtacgacct gcagttcatc tttcagctgt gcaagatcac cctgaccacc    1140
gaagtgatgg cctacatcca acatggac gccagcatcc tggaagattg aacttcggg      1200 ctgcaagctc cccccagcgg ctctctgcag gacacctaca gattcgtgac cagcagcgcc    1260
atcacctgtc agaagcctgc cccccctaaa gagaaagagg acccctggc caaatacgcc     1320 ttctgggacg tgaacctgaa agagaagttc agcgccgacc tggaccagtt ccccctgggc    1380
agaaagttcc tgctgcaagc aggcatgcgg ccagaccca ccctgaagaa gagaagcgcc     1440
cctagcacca gcagcagcac cccgccaag cggaagcgcg tgaagagatg a             1491
```

<210> SEQ ID NO 8
<211> LENGTH: 1434
<212> TYPE: DNA
<213> ORGANISM: Artificial Sequence
<220> FEATURE:
<223> OTHER INFORMATION: MfPV6_L2

<400> SEQUENCE: 8

| | | | | | |
|---|---|---|---|---|---|
| atgaagcacg | cccggctgag | cagaagaaag | cgggccacac | agcagagccc | ccccagagcc | 60 |
| agaagaaaaa | gagccagcgc | cacccagctg | taccagacct | gtaaagccgc | cggaacctgc | 120 |
| cccctgacg | tgatccctaa | ggtggaaggc | agcaccgtgg | ccgaccagat | cctgaagtac | 180 |
| ggcagcatgg | gcgtgttctt | cggcggcctg | ggaatcggca | caggctctgg | aacaggcggc | 240 |
| agaaccggct | atgtgcctct | gggcgctaga | ccctctgtgg | tgcctgaggt | gctgcccaga | 300 |
| cctcccgtga | cagtggaacc | tgtggcccc | accgatccca | gcatcgtgtc | tctgctggaa | 360 |
| gagagcagcc | tgatcgaggc | cggcgtgcca | gctcctatcg | tgcctacaca | cggcggcttc | 420 |
| gaagtgacca | ccagcgagac | aagcaccccc | gccatcctgg | atgtgtctca | gggcagcagc | 480 |
| aacgtgcaca | tcagcgtgaa | caccttcaac | aaccccgcct | tcaccgagcc | cagcgtgctg | 540 |
| catcctccac | ctccagtgga | agccagcggc | agacttgtga | tcagcagctc | caccgtgtcc | 600 |
| acccagaact | acgaagagat | ccccatggac | accttcgtga | tcaccggcga | ccaccggttc | 660 |
| aacaccacca | gcacacctat | ccccggcagc | agacctcctg | ccagactggg | cctgtatggc | 720 |
| agagcactgc | agcaagtgcg | ggtggtggat | cccgcctttc | tgaccacacc | cgccagactg | 780 |
| atcacctacg | acaaccccgt | gtacgagggc | gtggacgatg | ccaccctgca | gttcagccac | 840 |
| cccaccatcc | acgagccccc | cgaccctgac | ttcctggata | ttgtggccct | gcacagaccc | 900 |
| gccctgacaa | gcagacgggg | cacagtgcgg | tttagcagag | tgggccagag | ggccagcatg | 960 |
| cacacaagaa | gcggcgccag | aatcggagcc | cgggtgcact | actttcagga | cctgagcagc | 1020 |
| attgcccctg | ccgaggccac | aaccgagagc | atcgaaatgc | agcccctgct | gcctgccgcc | 1080 |
| acacaggaca | tcgacctgta | cgacatctac | gccgtggacg | aggacgtgac | ctctcctgcc | 1140 |
| cagcctaccc | tgcctttccc | aagctctaca | gcctccgccg | tggatgccac | actgccttgg | 1200 |
| acatccaccg | tgcctctgag | caccggcctg | gacatcacac | tgcagcctgg | ccccgatatc | 1260 |
| cctctgcagt | ttcctctggc | cgagagcccc | ctgcaccctg | tgacacctct | gacacctatc | 1320 |
| ggccacgtgg | tggtgcacgg | cggcgatttc | tatctgcacc | ccagctacta | caccctgcac | 1380 |
| aagcggcgga | agcggatgcc | cagatttctg | gccgatgtgt | ccgtggccgc | ctga | 1434 |

<210> SEQ ID NO 9
<211> LENGTH: 1500
<212> TYPE: DNA
<213> ORGANISM: Artificial Sequence
<220> FEATURE:
<223> OTHER INFORMATION: MfPV11_L1

<400> SEQUENCE: 9

| | | | | | |
|---|---|---|---|---|---|
| atgagcctgt | ggcggcctag | cgacgccaag | gtgtacctgc | ctcctgcccc | tgtgtccaag | 60 |
| gccatcagca | ccgacgagta | cgtgacccgg | accagcacct | actaccacgc | cggctctagc | 120 |
| agactgctgg | ccgtgggcca | cccttactac | cccgtgaaga | agtccaacgg | caagatcgcc | 180 |
| gtgcccaagg | tgtccggcct | gcagtacaga | gtgttcagag | tgaagctgcc | cgaccccaac | 240 |
| aagttcggcc | tgcccgatgc | caacttctac | gaccccaata | cccagcggct | cgtgtgggcc | 300 |
| tgcatcggca | tggaagtggg | cagaggacag | cctctgggcg | tgggcacatc | tggacacccc | 360 |

| | |
|---|---|
| ctgctgaaca agctggacga caccgagaac agccacaaca acggcgccaa ccagggcacc | 420 |
| gacaaccgcg agtgtgtgtc catggattac aagcagaccc agctgtgcct gctgggctgc | 480 |
| aagcctccta caggcgagca ctggggcaag ggcacccctt gtacatctgg cgccgatggc | 540 |
| gattgccccc ctctggaact gatcaacagc gtgatccagg acggcgacat ggtggatgcc | 600 |
| ggctacggct gcctggattt ccaggccctg cagaccaaca gagcgacgt gcccctggac | 660 |
| atctgcatga gcacatgcaa gtaccccgac tacctgaaga tggccagcga gccctacggc | 720 |
| gaccggctgt tcttttttcct gcggcgggaa cagatgttcg tgcggcacat gttcaacaga | 780 |
| gccggcacca tgggcgagac actgccagc gacctgtaca tcaagggcac aggcaacaga | 840 |
| agcagcctgg ccagccacat cttcagcagc acaccctccg gcagcatggt cacctctgag | 900 |
| agccagctgt ttaacaagcc ctactggctg cagcgggccc agggacacaa caatggcatc | 960 |
| tgctggggca accaggtgtt cctgaccgtg gtggacacca cccggtccac caatgtgacc | 1020 |
| ctgtgcgcca ccaagaccag cgaggacacc tacaagaacg acaacttccg cgagtacctg | 1080 |
| aggcacatgg aagagttcga cctgcagttc gtgtttcagc tgtgcaagat caccctgacc | 1140 |
| accgaagtga tggcctacat ccacaacatg gaccccagca tcctggaaga ttggaacttc | 1200 |
| ggcgtgcagc cccctcctgc cggaacactg caggatacct acagattcgt gcagagcgag | 1260 |
| gccatccggt gccagaaaac agccgcccct aaagtgaaag aggaccccct gagcaagtac | 1320 |
| accttctggg acgtggacct gcgggacaag ttcagcgccg acctggacca gttccccctg | 1380 |
| ggcagaaagt tcctgctgca agctggcatg cgggccagaa gcacactgag agcccccaaa | 1440 |
| agacccgccc ctaccacaag cagcggcagc agcaagaaga gaaagaccac cagaagatga | 1500 |

<210> SEQ ID NO 10
<211> LENGTH: 1428
<212> TYPE: DNA
<213> ORGANISM: Artificial Sequence
<220> FEATURE:
<223> OTHER INFORMATION: MfPV11_L2

<400> SEQUENCE: 10

| | |
|---|---|
| aagcttgcca ccatgaagca gcccgccaga gccagcagaa gaaggcggaa cgccaacggc | 60 |
| cacgtgcacc ggcccagaag aaaaagagcc agcgccaccc agctgtacca gacctgtaaa | 120 |
| gccgccggaa acctgccccc tgacgtgatc cctaaggtgg aaggcaccac cgtggccgac | 180 |
| cagatcctga gatacggcag catgggcgtg tacttcggcg gcctgggaat cggaacagcc | 240 |
| cctggatctg cggcagatc tggctatgtg cccctgggaa gcagacctgc cacagtgcct | 300 |
| gaggtgctgc ccagacctcc tgtgctggtg gaacctgtgg ccccagcga tcctagcatc | 360 |
| gtgtccctgg tggaagaggc caacctgatc gatgccggac tgcctgcccc tagcgtgcca | 420 |
| acaggcggag cttttaccgt gaccaccagc gacgtgtcca ccccgctat cctgcctgtg | 480 |
| acaccagccg agacaagcgt gcacgtgaca gtggacacct tcaccaaccc cctgttcacc | 540 |
| gagcccagcg tgttcacccc tccacccct atggaagcca ccggccacat cgtgctgagc | 600 |
| agcgatacag tgtccgccca cagctacgaa gagatcccca tggatacctt cgtcgtgacc | 660 |
| ggcgacaacg cctacaaccc taccagcacc cccatcccca ccccagacc tagagctaga | 720 |
| ctgggcctgt acggcagagg catgcagcaa gtgcgggtgt ccgatccgc cttcctgtct | 780 |
| agccctgccc ggctgatcac cttcgacaac cctgcctatg agggcctgcc cgaggacagc | 840 |
| ctgcagttcg agcacagcag catccaccag ccccccgacc ccgacttcct ggatattgtg | 900 |

| | |
|---|---|
| gccctgcaca gacccgccct gaccagcaga cagggcacag tgcggtatag cagagtgggc | 960 |
| aaccgggcca ccatccggac aagaagcggc aagcagatcg gcgccagagt gcacttcttc | 1020 |
| caggacatca gcgccatccc ccaccctgaa gagatcgaga tgcagcctct ggtgtctgcc | 1080 |
| caggaacccc tgttcgacgt gtacgccgac ctggaagatg cccccgaagt ggaaggcggc | 1140 |
| acaggcagcg ctacaagcag ctctgtgcct ccactgcagg gctccgccac ctggaacaca | 1200 |
| accgtgcctc tgaacaccgg cctggacatc tggtgcagc ctggacctga tgtgcccag | 1260 |
| cagtttcctg tggccgagag cccttactgg cccgccatgc cagtgtttcc gcagggccat | 1320 |
| gtgtacgtgt ccggcggaga ctttctgtgg caccccctccc tgtacacccc tcggcggaag | 1380 |
| agaaagcggg tgcacacctt cttcgccgat gtgtccgtgg ccgcctga | 1428 |

<210> SEQ ID NO 11
<211> LENGTH: 1506
<212> TYPE: DNA
<213> ORGANISM: Artificial Sequence
<220> FEATURE:
<223> OTHER INFORMATION: MmPV1_L1

<400> SEQUENCE: 11

| | |
|---|---|
| atgagcatgt ggcggcccag cgacagcaag gtgtacctgc ctcctgtgcc cgtgtccaag | 60 |
| gtggtgtcca ccgacgagta cgtgtcccgg accagcatct actaccacgc cggcagctct | 120 |
| agactgctgg ccgtgggcca cccttactac gccgtgaaga aaggcaacaa caaggtgtcc | 180 |
| gtgcccaaag tgtccggcct gcagtaccgg gtgttcagag tgcggctgcc cgaccccaac | 240 |
| aagttcggac tgcccgatgc caacttctac gaccccaata cccagcggct cgtgtgggcc | 300 |
| tgtctgggcg tggaagtggg aagaggacag cctctgggag tgggcacatc tggccacccc | 360 |
| ctgctgaaca gctggacga caccgagaac ggccccaagc tggctggcgg acagggcgcc | 420 |
| gataacagag aatgcgtgtc catggattac aagcagaccc agctgtgcat gctgggctgc | 480 |
| aagcctccag tgggagagca ctggggcaag ggcaatcctt gtaccacagc cgccgctggc | 540 |
| gattgccctg ctctggaact cgtgaacagc gtgatccagg acggcgacat ggtggataca | 600 |
| ggctacggcg ccatggactt caacgccctg caggccaaca gagcgacgt gcccatcgac | 660 |
| atctgcacca gcgtgtgcaa gtaccccgac tacctgaaga tggccagcga cccctacggc | 720 |
| gacagcctgt tcttttacct gcggcgcgag cagatgttcg tgcggcacct gttcaacaga | 780 |
| gccggcacca tgggcgacag cgtgcccgac gatctgtaca tcaagggcag cggcagcaac | 840 |
| gtgaagctgg cctcccacgt gttctacccc acaccctctg gcagcatggt cacctccgat | 900 |
| gcccagctgt taacaagcc ctactggctg cagaaggccc agggccacaa caacggcatc | 960 |
| tgctggggca accaggtgtt cctgaccgtg gtggacacaa cccggtccac caacatgacc | 1020 |
| ctgtgtgcca gcaccgcctc caccgtgacc accccctaca caacgagag cttcaaagaa | 1080 |
| tacctgcgcc acgtggaaga gttcgacctg cagttcatct ccagctgtg taaagtgacc | 1140 |
| ctgaacaccg aagtgatggc ctacatccac agcatggacg ccagcatcct ggaagattgg | 1200 |
| aactttggac tgcagccacc cccaagcggc agcctgcagg acacctacag attcgtgacc | 1260 |
| agcgccgcca tcacctgtca gaagcctgcc cccctaaag agaaagagga ccccctggcc | 1320 |
| aagtacacct tctgggaggt ggacctgaaa gagaagttca gcgccgacct ggaccagttc | 1380 |
| ccctgggca gaaagttcct gctgcaagct ggcatgcggg ccagacctac actgagagcc | 1440 |
| cctaagagaa ccgccagcag caccagctcc agcagccccc ggaagcggaa acggaccaag | 1500 |
| agatga | 1506 |

<210> SEQ ID NO 12
<211> LENGTH: 1566
<212> TYPE: DNA
<213> ORGANISM: Artificial Sequence
<220> FEATURE:
<223> OTHER INFORMATION: MmPV1_L2

<400> SEQUENCE: 12

| | | | | | | |
|---|---|---|---|---|---|---|
| atgaagcacg | cccacgtgtc | agaagaaag | agagccgccc | ctagaccccc | tggcggcaga | 60 |
| cagaaaagag | ccagcgccac | ccagctgtac | agacctgta | aagccgccgg | aacctgcccc | 120 |
| cctgacgtga | tccctaaggt | ggaaggcacc | accgtggccg | accagatcct | gaagtacggc | 180 |
| agcatgggcg | tgtacttcgg | cggcctggga | attggatctg | gcgctggaac | aggcggcaga | 240 |
| tccggctatg | tgcctctggg | ctctagaccc | gccagcatcc | tgagcctct | gcccagacct | 300 |
| cctgtgacca | tcgagcctgt | gggccccagc | gatcctagca | tcgtgtccct | gctggaagag | 360 |
| agcagactga | tcgaggccgg | cgtgccagcc | cctaccttc | ctacacacgg | cggcttcgag | 420 |
| atcagcacca | gcgaggtgtc | cacccccgcc | atcctggatg | tgtctagcag | cggcagcaat | 480 |
| gtgcacgtgt | ccgtgaccac | cttcaccaac | cctaccttca | ccgagcccag | cgtgctgagg | 540 |
| cctcctccac | ctgtggaagc | ctctggcaga | cttgtgatca | gcgccagctc | cgtgtctacc | 600 |
| cacagctacg | aagagatccc | catggacacc | ttcgtgatca | ccggcgacca | caactacaac | 660 |
| accaccagca | cccccatccc | cggcagtaga | gcaccagcta | gactgggcct | gtacggcaga | 720 |
| gccacacagc | aagtgcgggt | ggtggacccc | gccttcatca | aaccctgc | ccggctcgtg | 780 |
| acctacgaca | accctgccta | tgagggcgtg | gacgacgcca | cctgcagtt | cagccacagc | 840 |
| gacatccacc | agcccctga | ccccgacttc | ctggatattg | tggccctgca | cagaccgcc | 900 |
| ctgaccagca | gaaagggcac | cgtgcggttt | agccggctgg | gccagagagc | caccctgacc | 960 |
| acaagaagcg | gcaagcggat | cggcgccaag | gtgcacttct | accacgacct | gagccctatc | 1020 |
| gcccctgccg | agagcattga | gctgcagcct | ctgtctagcc | agggcgagct | gtacgacatc | 1080 |
| tacgccgatg | tggacggcca | ggaagatgtg | ccgccatgg | ccgacacccc | cctgaacagc | 1140 |
| aatagctctg | gcaccgcctc | ccctggaat | accaccgtgc | cactgtctgc | tggcgccgac | 1200 |
| gtgacactgc | agtctggccc | tgatgtgtcc | ctggatgccc | ctgtggccga | aagccctgtg | 1260 |
| catcctgggg | tgccactgag | gcctagcgcc | cacatcatcc | tgtatggcgg | cgacttctac | 1320 |
| ctgcacccca | gctacctggg | catccggcgg | aagcggaaga | gaatgcacaa | cttcttcagc | 1380 |
| gacgtgtacg | tggccgcctg | agggactcct | cgagctgggc | tcatgggcc | ttccgctcac | 1440 |
| tgcccgcttt | ccagtcggga | aacctgtcgt | gccagctgca | ttaacatggt | catagctgtt | 1500 |
| tccttgcgta | ttgggcgctc | tccgcttcct | cgctcactga | ctcgctgcgc | tcggtcgttc | 1560 |
| gggtaa | | | | | | 1566 |

<210> SEQ ID NO 13
<211> LENGTH: 1503
<212> TYPE: DNA
<213> ORGANISM: Artificial Sequence
<220> FEATURE:
<223> OTHER INFORMATION: PcPV1_L1

<400> SEQUENCE: 13

| | | | | | | |
|---|---|---|---|---|---|---|
| atggccgtgt | ggctgcccgc | ccagaacaag | ttctacctgc | ccctcagcc | caccaccaga | 60 |
| gtgctgcaca | ccgacgagta | cgtgacccgg | acccggatct | tctaccacgc | cagcagcgac | 120 |

```
agactgctga ccgtgggcca cccattcttc gacatctaca agaaccagga aatcatcgtg      180
cccaaggtgt cccccaacca gtaccgggtg ttccggctga gactgcccga ccccaacaac      240
ttcgccttcg gcgacaagag cctgttcaac cccgagaaag aacggctcgt gtgggccctg      300
agaggcctgg aaatcggcag aggacagcct ctgggcgtgg gcgtgtccgg caaccctacc      360
ttcgacagat acagcgacgt ggaaaacgcc aacaagaacc ccaccggcca cgccgacaat      420
gcccccgacc ctagagtgaa tatgccgtg gaccccaagc agacccagat gttcatggtg      480
ggatgcaagc ccgccctggg cgagcattgg gtcaaggcca gatggtgcaa tggcgccgct      540
cacgagagcc agcagtgccc tcctatcgag ctgaagaaca cccccatcga ggacggcgac      600
atggtggaca tcggcttcgg cgccatggac ttcaagaacc tgcagcagaa ccgcagcgcc      660
gtgccctgg acatcatcga cacccactgc aagtaccccg actacatcaa gatggccaac      720
gaccctacg gcgatacctg cttcttcttc gtgcggcggg aacagctgta cgccagacat      780
ctgctggccc gctctggaca agtgggcgag cctgagcctg agagaaccgt ggccaccaga      840
agcacctacc ccacccgtgaa ctacttcagc agccccagcg gcagcctggt gtctagcgaa      900
gcccagctgt tcaacagacc ctattggatc cagcggagcc agggccagaa caacggaatc      960
gcctgggaga ccagctgtt tctgacagtg ccgacaaca ccagaggcac cccccctgacc     1020
atcaacgtgg gccccaatga cagagccgag gatggcgagt acaaggccgg cagctacaag     1080
acctacctgc ggcacgtgga agagttcgac atcagcgtga tcctgcagct gtgcaaggtg     1140
cagctgaccc ccgagaatct ggccaccatc acacaatga accccgatat catcgagagc     1200
tggcacctga acgtgaaccc cccttctggc gccctggacg acacctaccg gtacatcaca     1260
agcctggcca caaagtgccc caccaacgtg ccccccaaag agagagagga cccttacgcc     1320
cacctgaagt tctgggaggt ggacctgcgg gacaagctga ccgagcagct ggatcagacc     1380
ccctgggcc ggaagttcct gttccagacc aatgtgctgc agggcggagg cagcaagagg     1440
gccagagtga ccacaagcgt gtccaaggac aagcccgtga gcggcggag aggccagaaa     1500
tga                                                                  1503
```

<210> SEQ ID NO 14
<211> LENGTH: 1548
<212> TYPE: DNA
<213> ORGANISM: Artificial Sequence
<220> FEATURE:
<223> OTHER INFORMATION: PcPV1_L2

<400> SEQUENCE: 14

```
atgctgctga agcggcggaa gagagccgcc cctaaggaca tctacccca gtgcaagatc       60
agcaacacct gtccccccga cgtgctgaac aaggccgagc agtctaccct ggccgacaag      120
atcctgaagt acggctctgc cggcgtgttc ctgggctctc tgggaatcgg aacaggcaga      180
ggctctggcg gcacactggg ctatgtgcct gtgggaacag gacagggcgt gcggctgggc      240
accagagtgt ctacagtgcg gcctagcctg cccatcagct ctgtgggcac agccgacgtg      300
atccccatcg acgctgtgga tcctctggga cctgctgtgc tgcccggcaa cgtgttccct      360
accgccgtga agatcccctt caccatccag ccccccagat tccccagcat cgtggaagaa      420
cccgtgtccg tgcacagcga gagcatcgtg accgagagcg tgacagaggt gcccgtgaac      480
accccccaaag tgaccatcga cggacagccc gccgtgctgg aagtggtgcc tgagacaaga      540
gagccccgga tcctgagcag aagccagtac ggcaacagcg ccttcgaggt gtccctgaca      600
gcctctgctg gcagcggcga gacaagcagc agcgaccaca ttctggtgca cggcttcaca      660
```

```
ggcggccacg tgatcggaga gcagatcccc ctgcaggaac tgggcggcag atccttcagc    720
tccaccctgg aagccgagac aaccttcacc acctccaccc ccaaggccga tgccgtggcc    780
gaacccagaa gagtgttcac cagcaggcgg ctggaacaga tccccgtgcg ggatcctggc    840
ttcatcagca accccggtc cctcgtgacc ttccagaacc ccaccttcga tgagagcgtg    900
gacctgttct tcgagcggga cgtggcagaa ctggccctgg ccgctcccaa cgaggacttc    960
agagatctgg tgtctctgag caagcccacc ttcagccgga cactggaagg cagagtgcgg   1020
gtgtccagac tgggcacaaa ggccaccatg agaacccgca gcggcctcgt gattggcccc   1080
cagagccact actactacga cctgtccgat atcgcccctg ccgagaacct ggaactgacc   1140
cccatcggca acatgagcct gggcgaacag agcggacagg ccgtgatcag cagcggcacc   1200
agcgacctgg aaatcatcag cctggaaagc agcaccatcg acagctaccc cgaagagttc   1260
ctgctggccg agatcgaaag cgtggccaac gacctgcagc tggtgttcgg cgatagaagg   1320
gcccagcagc ctatcagcgt gccccacatt cagaggccca gccccaggt gttccctcag   1380 tttgagggcg tgtacgtgtc ccagggcaca ggcagtgtgc ccctaccat ccccaccgac   1440 cctaacaaga cccccgccat cattctggaa atctggggct ccggcgagaa ctacagcctg   1500
cacccaagcc tgctgaagag aagaaagcgg aagcggctga ttctctga                1548
```

```
<210> SEQ ID NO 15
<211> LENGTH: 1509
<212> TYPE: DNA
<213> ORGANISM: Artificial Sequence
<220> FEATURE:
<223> OTHER INFORMATION: P1PV1_L1

<400> SEQUENCE: 15
```

```
atggccgtgt ggctgccgc ccagaacaga ttctacctgc cccctcagcc cagcaccaag     60
gtgctgaaca ccgacgacta cgtgacccgg accagcatct tctaccgc cggcagcgag    120 agactgctga cagtgggcca ccccctgtac gacatctacg acgccgagaa cgagcacgtg   180
atcgtgccca aggtgtccgc caaccagtac cgggtgttcc ggatcagact gcccgacccc   240
aacaacttcg ccttcggcga caaggccatc ttcgaccctg agaaagaacg gctcgtgtgg   300
gccgtgcggg gcctggaaat tggaagagga cagcctctgg gcgtgtgcgt gtccggcaac   360
cccctgttcg ataagaacaa cgacgtgaa accccacca gtacttcgc caaccacgag    420 caggccgaca cagagtgaa cgtggccttc gaccccaagc agacccagct gttcatgatc   480
ggctgcaagc ccgccatcgg cgagcattg ggacaggcta agatgtgtgt gggcgagggc   540 cacacccag ccactgtcc tccaatcgag ctgaagaaca ccaccatcga ggacggcgac   600
atgatcgaca tcggcctggg cgccatggac ttcagagtgc tgcagcagaa caaggccggc   660
gtgcccctgg acatcagcaa cagcgagtgc aagtaccccg actacatcaa gatggccaac   720
gacccctacg cgacaacct gttcttctac gtgcggagag agcagctgta cgcccggcac   780
atgttcacca gaagcggcaa cctgggcaac gagacagtgc ccaccgatag atacgtgaac   840
cgggccgaca ataccatccc caccagcaac tacttcagca ccccagcgg cagcctggtg   900 tctagcgagg ctcagctgtt taaccggccc tattggatcc agcggagcca gggccagaac   960
aacggaatcg cctggcagaa tcagctgttc atcaccgtgg tggacaacac ccggggcacc   1020
agcctgaaca tcatcatggg caaggacgac aagaccgcca aggcgacctt caaccccgcc   1080
gactaccggt gctacatgcg gcacgtggaa gagtacgaga tcagcctgat cctgcagctg   1140
```

```
tgcaaagtga agctgacccc cgagaacctg gccttcatcc acaccatgaa ccccgacatc    1200
atcgaggatt ggcacctgaa cgtgaacccc cctgccggcg ctatcgacga cgtgtaccgg    1260
ttcatcaaca gcctggccac caagtgcccc gacaacgtgc cccctaagac cagagaggac    1320
ccttacggcc tgtacagatt ctgggaggtg gacctgaagg acaagatgac cgagcagctg    1380
gaccagaccc ccctgggcag aaagttcctg ttccagaccg gcgtgctgca gaggcgggcc    1440
agacctgcca atagagtgtc caccagcacc accagacggg ccgtgaagag aaagcgggcc    1500
agcaaatga                                                            1509
```

<210> SEQ ID NO 16
<211> LENGTH: 1548
<212> TYPE: DNA
<213> ORGANISM: Artificial Sequence
<220> FEATURE:
<223> OTHER INFORMATION: P1PV1_L2

<400> SEQUENCE: 16

```
atgaccacca gaagccggaa gagaagggcc gctcccagag acatctaccc cagctgcaag    60
ctggccaaca cctgtccccc cgacatcgtg gacagcatcg agaacaacac cctggccgac    120
aagatcctga gtacggctc tgccggcgtg ttcttcggct ctctgggcat cggaaccggc    180
agaggcacag gcggcagcac aggctatatc cctctgggag aaggcgctgg cgtgcggctg    240
aataccgagt gtctaccgt gcggcccagc ctgcctatca gcagcgtgca ccctaccgac    300
gtgatccccg tggatgccgt ggatcctctg gacctgcca tcgtgcctct gagcgagctg    360
cctagcatcg tggaagatcc cgaccccatc ctgccccca gatttccaac agccgtggaa    420
gagagcgtga tcgacttcag ccctgctggc cctggcggcg atctgcctat ccagagccct    480
aaagtgacca ccaccgacac cagcgccctg atcgaagtga ccccgagac aagaccccc    540 agaatcatca gcagaagcca gtacagcaac cccagcttcg aggtgcacat caccagcacc    600
tctggcagcg gcgaaagctc tgccgtggac cacgtgctga tcgacggcta ctctggcgga    660
gaagtgatcg gcgaggaaat ccctctgatc gacctgcaga gcacccggtc cagcaacacc    720
ttcagcacca ccgaagtgcg ggaaaccagc ttcttcacct ccaccccag aggggagctg    780 ccaagcgcca gacctagaac cctgtacaac cggcgggtgc agcaggtgca ggtggtggat    840
cctgccttcc tgagcagacc tggcgccctc gtgaccttcg acaacccgc ctacaccgac    900 gacgtggaac tgatcttcga gcaggacctg gacgacctgg ccagagccgc ccctcacgag    960
gacttcagag atatcgtgtc cctgggcaga cccgtgtacg gcagaaatcc tcagggcggc    1020
gtgcggatca gcagactggg acagaaagcc accatgcgga ccagatccgg cctgagaatc    1080 ggccccccaga gccacttctt ctacgacatc agcgagatcg ccgagccga gctggaactg    1140 gtgcctctgg aacacccttt cgtgggcgag cagacaggcg agagcgtcgt gggatctgcc    1200
ctgggcgagt cgagacaat cagcctgagc aacgagcccg ccatctaccc tgaggacacc    1260
ctgattgacg agtacgaggt cgtgggcagc gatctgcagc tgatcatcgg cgatagcgga    1320
ggcgagaggc ctatccctgt ggccgacttt gccagacccc tgccaagct gttccctgag    1380 ctggatggcg tgcaagtgat caacggccgg acgtgtcca gatccgccac cgtgcctgtg    1440
attcccgagg atacccccct gatcatcatc gaagtgctgg acggctccgg cgactacttc    1500 ctgcaccca gcctgttccg gaagcggcgg aagaggccat tcttctga              1548
```

<210> SEQ ID NO 17
<211> LENGTH: 1506

```
<212> TYPE: DNA
<213> ORGANISM: Artificial Sequence
<220> FEATURE:
<223> OTHER INFORMATION: PtPV1_L1

<400> SEQUENCE: 17
atgtggcggc cagcgacaa caagctgtac gtgccacctc ctgcccccgt gtccaaggtg      60
ctgaccacag atgcctacgt gacccggacc aagatcttct accacgccag cagcagcaga    120
ctgctggccg tgggcaaccc ctacttcccc atccggaagg ccaacaagac catcgtgccc    180
aaggtgtccg gcttccagtt ccgggtgttc aagatcgtgc tgcccgaccc caacaagttc    240
gccctgcccg acaccagcat cttcgacagc accagccaga gacttgtgtg ggcctgcatc    300
ggcctggaag tgggcagagg acagcctctg ggcgtgggct attgtggcca ccctgcctg     360
aacaagtttg acgacgtgga aaacagcgcc agctacgccg tgaacccggg ccaggacaac    420
agagtgaacg tggccatgga ctacaagcag acccagctgt gcctcgtggg ctgtgctcct    480
ccactgggag agcactgggg caagggcaag cagtgttctg gcgtgtccgt gcaggacggc    540
gattgccctc ctctggaact cgtgaccagc gtgatccagg atggcgatat ggtggacacc    600
ggcttcggcg ccatggattt cgccgagctg cagagcaaca gagcgacgt gcccctggac     660
atctgcacca gcacatgcaa gtaccccgac tacctgcaga tggccgccga ccctatggc     720
gaccggctgt tcttctacct gcggaaagaa cagatgttcg cccggcactt cttcaacaga    780
gccggcacag tgggcgagca gatccccgat gagctgttcg tgaagggcac caccagcaga    840
gccaccgtgt ccagcaacat ctacttcaac accccagcg gcagcctggt gtctagcgag     900
gcccagctgt tcaacaagcc ctactggctg cacaaggccc agggccacaa caacggcatc    960
tgctggggca caccctgtt tgtgaccgtg gtggatacca ccgcagcac aacatgacc     1020
gtgtgcgcca gcaccacctc tagccctagc gccacataca ccgccagcga gtacaagcag   1080
tacatgcggc acgtgaaga gttcgacctg cagttcatct tccagctgtg taccatcaag    1140
ctgacagccg agctgatggc ctacatccac accatgaacc ccaccgtgct ggaagagtgg   1200
aacttcggcc tgagccccc tcccaatggc accctggaag ataccacag atacgtgcag    1260
agccaggcca tcacctgtca gaagcccacc ccgacaaaga gaagcagga cccttacgcc    1320
ggcctgtcct tctgggaagt gaacctgaaa gagaagttca gcagcgagct ggaacagtac   1380
cccctgggcc ggaagttcct gctgcagaca ggcgtgcagt ctaccagcct ggccagagc    1440
ggaacaaaga gagccgccag cacaagcacc gccaccccca ccagaaagaa agtgaagcgg   1500
aaatga                                                             1506

<210> SEQ ID NO 18
<211> LENGTH: 1389
<212> TYPE: DNA
<213> ORGANISM: Artificial Sequence
<220> FEATURE:
<223> OTHER INFORMATION: PtPV1_ L2

<400> SEQUENCE: 18
atggcccaca gccggcccag aagaagaaag agagccagcg ccacccagct gtaccagacc      60
tgcaaggcca gcggcacctg tcccgacatc atccccaagg tggaacagaa cacccctggcc    120
gacaagatcc tgaagtgggg cagcctgggc gtgttctttg gcggcctggg aatcggcaca    180
ggctctggca caggcggcag aacaggctac gtgccactgg aaagcgcccc cagacccgcc     240
atccctttg gcccaacagc cagaccccct atcgtggtgg ataccgtggg ccccaccgac     300
```

```
agcagcatcg tgtccctggt ggaagatagc gccatcatca acagcggcgc cagcgacctg    360
gtgccttcta ccacggcgg cttcgagatc agcaccagcg agagcacaac ccctgccatc     420
ctggacgtgt ccatcaccac ccacaacacc accagcacct ccatcttccg gaaccccgcc    480
ttcgccgagc ctagcatcgt gcagtctcag ccctctgtgg aagccggcgg acatctgctg    540
acctccacct tcacctccac catcagcccc cacagcgtgg aagagatccc cctggacacc    600
tttatcgtgt ccagcagcaa cagcaaccc gccagcagca cccctgtgcc tacaacagtg     660
gccagaccca gactgggcct gtacagcaaa gccctgcatc aggtgcaagt gaccgaccct    720
gccttcctga gcccccca gagactgatc accttcgaca ccccgtgta cgagggcgag       780 gacatcagcc tgcacttcga gcacaacagc atccacgagc cccccaacga ggccttcatg    840
gacatcatca gactgcacag gcccgccatc accagcagac ggggagttgt gcggttcagc    900
agaatcggcc agcggggcag catgtacacc agaagcggca agcacatcgg cggcagagtg    960
cacttcttca ccgatatcag ccccatcagc gccgacgccc aggacattga actgcagcct   1020
ctggtggccg ctgcccagga cgatagcgac ctgttcgaca tctacgtgga ccccgacacc   1080 accccgtgg ccgtggacaa tatccccagc gccaactcca ccctgttcat caagagcagc    1140
atcttcgaca ccagctgggg caataccacc atccccctga gctgcccaa caacatcttc    1200 gtgcagcctg gccccgacat cctgttccct acaacaccag ccgtgccccc ctacggccct   1260
gtgatttctc tctgcctgt gggccccgtg ttcatcagcg gcagcgagtt ctacctgcac    1320
ccctccctgt acttcgcccg gaagaggcgg aagcgggtgt ccctgttctt tagcgacgtg    1380
gccgcctga                                                          1389

<210> SEQ ID NO 19
<211> LENGTH: 1662
<212> TYPE: DNA
<213> ORGANISM: Artificial Sequence
<220> FEATURE:
<223> OTHER INFORMATION: RaPV_L1

<400> SEQUENCE: 19
atgacccagc tgcacatgac caccggcctg atctacacct gtacctgcct gggcaagagc     60
gccaatggcg tgccatctgc cctgctgcag atggccctgt ggatcccatc tccccaggcc    120
gtgtatgtgg cccctgcccc tgtgaccacc atccccagca ccgaggactt catcacccgg    180
accccctact tctaccacgc caacagcgac cggctgctga ccgtgggcaa tcccttctac    240
gccatcaagg accccggcac ccagaaaatc ctggtgccca ggtgtccgg caaccagtac     300 cgggtgttcc ggatcagatt ccccgacccc aacaagttcg ccctgcccga ccctaacgtg    360
ttcaaccccg acaccgagag acttgtgtgg ggcctgagag catcgaagt gggcagaggc    420 ggaccctgg gcatggaagt gacaggcaat ctgggcttcg ccggaacgc cgacgtggaa      480 aaccctaacc aggccgagag gaacatggcc gcgtgggca ccaagagatt caacgtggga    540
atggaaccca gcagaaccca gctgctgatt gtgggctgta cccagcctg ggcgagttc     600 tgggatagca cccctgcttg caccgagggc gatacccag tggatcctgg cgctggcgat    660
tgccctgccc tggaactgaa gtccaccaga ctgcaggacg gcaccatgac agacatcggc    720
tttggccaca tgaacttcaa gagcctgcag gatgacaaga gcggcgtgcc cctggaaatc    780
gtgaacagcg tgtgcgtgta ccccgacttc tacaagatga gcaaggaccc ttacggcaac    840
agctgcttct tcagcgtgcg gaaagaacag atgtatatcc ggcactactt cagcagagtg    900
ggcgcctacg gcgacaccgt gcccaccgat atgtacctga aggacaagac caacggcgga    960
```

```
gccaactgga ccggccctgt gtacatggga acacccagcg gcagcatcgt gtctaccgag    1020
ggccaggtgc tgaaccggcc ttactggctg ctgaaggccc agggcagaaa caacggcatg    1080
ctgtggggca atcagtgctt cgtgaccgtg gtggacaata ccagaagcct gaacttcctg    1140
atcaacgtga agaacgacgc cggcaccagc ttccaggccg acgagttcgc caactacctg    1200
cggcacaccg aggaatacga gatcgcctgc atcgtgcagc tgtgcaaagt gcggctggac    1260
cccgagacac tgagcatcct gaacaccatg gaccctgaga tcctggaaga gtggcagatc    1320
ggcgtgaacc ccctgtgtc cagccaagtg aacgaccggt acagattcgt gcacagcctg    1380
gccacccact gccccgacaa agagaaggcc aaagagaaag aggacccta cgccggcctg    1440 gccttctgga acctggattt caccgagagc ctgagccccg acctggacca gtttcctctg    1500
ggcagacggt tcctgacaca ggccggcaga gccggaagaa ccagcggcac aagaagcacc    1560
gccagaaccg cagaacagg caccgtcgtg aagcggtcca tcgtgtccac aaccgtggcc    1620
ggcaagccta gaagcgtgcc cgctaagcgg cggagaagat ga                       1662
```

<210> SEQ ID NO 20
<211> LENGTH: 1671
<212> TYPE: DNA
<213> ORGANISM: Artificial Sequence
<220> FEATURE:
<223> OTHER INFORMATION: RaPV1_L2

<400> SEQUENCE: 20

```
atggccccca gaaagcggag agccaccaga gtgcctagag acagcgccac caacctgtac     60
agacagcccg gctgcagagt ggacggcaac tgtccttggg gcgtgaaaga gcagatcgag    120
aacaagaccc ctgccgaccg gatcctgcag tacggcagcg ccgtgatcaa tctgggcggc    180
ctgggaatcg aacaggcgc tggatctggc ggcagaggcg gctatattcc catgggcgcc    240
gatagaggca tcggcgtggg agcttggcct agacctgcct accctgccag acctgtggtg    300
cccgccattg agacagtggg ccccaccatc agcatccccg aagtggtggc cacagacgtg    360
atcgagatgg aacccatcgt gaccgccgtg gaccccagcg tgatcgatac ccacccccc    420 atcgacccta ccgaccctgc catcgtggaa gatttcggca gctaccccc cagacccgcc    480 atcattgatg agagcgtgcc aacccagggc ggcaacagaa ttcaggtggt ggccgaggtg    540 caccacccg ccgatctgtt ccaagcacc accatctcta gcggcggctc cacaacaagc    600
gccgtgctgg aagtgggcga gcagatcccc ctgatgccca aagcaaccc cccccacatc    660 cacgagccta gcctgctgac caccacaacc agcttcggca ccaacgccga cgtcgtggga    720
agcagagcca gcatcatcga cttcgacgcc gtggatgaag ccgtgggcga cgacatccct    780
ctgctggaca gaacctacga ccggaacgcc aacctggaat ccggaccag cacaccccag    840 agcggcagac ggcctaatcc tgtgaaggcc ctgaagtccc tgtacaacaa atacgtgcgc    900
caggtgccag tggaagatcc cctgttcatg aagcccctg ccacctgat cgagttcggc    960 aaccctgtgt ccagcccga ggaaagcctg gaatacccac tgcaggacaa ccccctggcc   1020 tccccgatg agagactgca gggaacccac agactgcacc ggcccatcct gtctgaagtg   1080
ccaggcggca ggggcatcag actgtctaga ctggagccat cggcgccat gcggatgaga   1140 tctggcctga ccgtgggccc tagagtgcac gtgtaccacg acatcagcag catcgaggaa   1200
gccatcgagc tgcagcccct gggcgtgaa cctcactctg tgacaggcga ggccgtgatg   1260 caggacaccct ctgtggatgc cctgaccgaa gaggacatca ccgagcaggg cttcgaggac   1320
```

-continued

```
gtgccactgc tgtctccaca tgccggacag caagtgcgcc tgcaagtggg acctggcgga      1380
cggaacaacc ggaacgtggt gtccctggaa atccccacca ccaaccgggc cgacaccttc      1440
ggcatcaata tcggcgaggc cagcgacatc tacgtgcact acgccgacga gaagcacacc      1500
atccccggct tcgtgcctgg cattcctctg gaacctgctg tgcccctgt  gattgtggaa      1560 gatgacaccg ccgcctacga ctattggttc gacctgtacc tgcatctgcc ccggaagaaa      1620
cggaagtggt gcagcttctg cagcctgacc gacggcatcg tggacacctg a              1671
```

<210> SEQ ID NO 21
<211> LENGTH: 494
<212> TYPE: PRT
<213> ORGANISM: Artificial Sequence
<220> FEATURE:
<223> OTHER INFORMATION: CcPV1_L1

<400> SEQUENCE: 21

```
Met Ala Val Trp Thr Pro Ser Thr Lys Ala Leu Phe Val Pro Pro Val
1               5                   10                  15

Asn Val Pro Thr Leu Tyr Ser Thr Arg Glu Tyr Val Arg Arg Thr Ser
            20                  25                  30

Tyr Val Phe His Gly Thr Thr Glu Arg Leu Ile Thr Ile Gly Asn Pro
        35                  40                  45

Tyr Phe Ala Leu Thr Asp Asn Ala Thr Val Thr Val Pro Lys Val Ser
    50                  55                  60

Ala Tyr Gln His Arg Val Phe Arg Ile Lys Leu Pro Asp Pro Asn Lys
65                  70                  75                  80

Phe Pro Ile Pro Glu Ser Ala Val Gly Asp Arg Asp Thr Thr Arg Leu
                85                  90                  95

Val Trp Ala Val Arg Gly Ile Gln Val Asn Lys Ser Gln Pro Leu Gly
            100                 105                 110

Val Gly Ala Ser Gly Asn Thr Met Phe Asn Gly Leu Gln Asp Phe Ala
        115                 120                 125

Glu Thr His His Pro Ser Met Glu Lys Pro Asp Pro Pro Glu Asp Arg
    130                 135                 140

Arg Val Asn Ala Ala Phe Asp Ala Lys Gln Ser Gln Ala Leu Ile Val
145                 150                 155                 160

Gly Cys Ile Pro Pro Val Gly Gln His Trp Asp Ala Ala Lys Arg Cys
                165                 170                 175

Val Glu Asp Asn Asn Lys Asp Met Cys Pro Pro Leu Glu Leu Gln His
            180                 185                 190

Thr Val Ile Glu Asp Gly Asp Met Ile Asp Met Gly Met Gly Thr Leu
        195                 200                 205

Asn Phe Lys Ser Leu Ser Leu Asn Trp Ser Thr Leu Pro Leu Glu Leu
    210                 215                 220

Ile Asn Ser Val Ser Lys Tyr Pro Asp Trp Leu Thr Met Asn Ala Asp
225                 230                 235                 240

Pro Tyr Gly Asn His Cys Phe Phe Met Leu Lys Arg Glu Gln Val Tyr
                245                 250                 255

Met Lys Gly Val Gly Leu His Leu Gly Asn Ile Gly Glu Asp Glu Pro
            260                 265                 270

Thr Thr Met Phe Arg Lys Gly Thr Gly Gln Lys Tyr Gln Thr Pro
        275                 280                 285

Gly Arg His Ser Trp Phe Pro Leu Leu Ser Gly Ser Leu Ser Thr Ser
    290                 295                 300
```

```
Asp Asn Gln Leu Phe Asn Arg Pro Tyr Trp Leu Glu Asn Ser Thr Ala
305                 310                 315                 320

Pro Asn Asp Gly Ile Cys Trp His Asn Gln Met Phe Val Thr Cys Val
            325                 330                 335

Asp Thr Thr Arg Asn Thr Ile Phe Gln Ile Ser Gln Phe Lys Lys Gly
            340                 345                 350

Val Thr Ala Thr Ala Asp Tyr Lys Glu Ala Asn Tyr Asp Met Tyr Ala
            355                 360                 365

Arg His Val Glu Glu Tyr Glu Ile Ser Phe Ile Leu Gln Leu Cys Ser
            370                 375                 380

Ile Lys Met Asp Leu Pro Val Leu Asn His Leu His Asn Met Asp Ala
385                 390                 395                 400

Ser Leu Leu Asp Asp Trp Gly Phe Gly Ala Thr Pro Pro Gln Asn Leu
            405                 410                 415

Thr Val Glu Asp Gln Tyr Arg Phe Leu Asn Ser Lys Ala Thr Lys Cys
            420                 425                 430

Pro Pro Pro Ala Thr Pro Ala Asp Ala Asp Pro Trp Gly Lys Tyr
            435                 440                 445

Lys Phe Trp Asp Val Asp Cys Thr Ala Gln Ile Ser Ser Asp Leu Thr
450                 455                 460

Pro Phe Pro Leu Gly Arg Arg Phe Gln Gln Leu Tyr Pro Gln Ala Gly
465                 470                 475                 480

Lys Pro Ala Pro Ser Asn Pro Arg Lys Arg Arg Gly Arg
            485                 490
```

<210> SEQ ID NO 22
<211> LENGTH: 452
<212> TYPE: PRT
<213> ORGANISM: Artificial Sequence
<220> FEATURE:
<223> OTHER INFORMATION: CcPV1_L2

<400> SEQUENCE: 22

```
Met Met Ser Lys Arg Arg Arg Val Thr Arg Ala Ser Pro Asp Asp Ile
1               5                   10                  15

Trp Arg His Cys Lys Gln Phe Gly Asp Cys Pro Asp Asp Ile Gln Lys
                20                  25                  30

Val Tyr Thr Gly Asn Thr Ile Ala Asp Asn Ile Leu Lys Trp Ala Ser
            35                  40                  45

Ser Phe Leu Phe Phe Gly Gly Leu Gly Ile Gly Ser Ala Glu Gly Ala
    50                  55                  60

Val Ala Ala Ala Ala Ser Glu His Ile Leu Pro Ile Gly Gly Gly Ser
65                  70                  75                  80

Leu Pro Lys Gln Pro Ile Asp Val Pro Ile Thr Arg Val Pro Ala Ser
                85                  90                  95

Asn Val Thr Pro Gly Phe Ser Asp Ile Thr Val Asn Pro Asp Val Ala
            100                 105                 110

Leu Asp Ala Gly Thr Val Val His Ala Ala Glu Pro Val Asp Pro Val
        115                 120                 125

Ser Gly Thr Pro Pro Ile Ile His Ala Ser Pro Asn Ser Thr Glu Val
    130                 135                 140

Ile Pro Pro Ile Arg Pro Val Glu Asn Pro Pro Trp Gln Asn Pro Phe
145                 150                 155                 160

Asp Ser Gly Leu Glu Thr Pro Gly Val Asn Val Gly Val Val Asp Tyr
                165                 170                 175
```

```
Ser Ala Gly Asn Glu Ile Glu Leu Ser Val Leu Ser Ser Thr Ala Pro
            180                 185                 190

Thr Leu Thr Asn Ala Val Glu Glu Thr Glu Leu Phe Ser Arg Phe Glu
        195                 200                 205

Leu Asp Pro Arg Thr Ser Thr Pro Asn Thr Thr Thr Arg Gly Gly Trp
    210                 215                 220

Met Ser His Val Ala Val Gly Arg Phe Ala Lys Thr Ala Ala Arg Glu
225                 230                 235                 240

Val Pro Leu Pro Val Leu Thr Ser Thr Gly Gly Val Met Gln Phe Glu
                245                 250                 255

Asn Pro Ala Phe Glu Phe Ser Glu Ala Val Ser Glu Val Ser Arg Ser
            260                 265                 270

Ile Ser Phe Asn Asp Pro Asp Ser Ala Pro Phe Ala Arg Leu Ser Arg
        275                 280                 285

Pro Ser Leu Phe Gln Arg Ala Gly Arg Leu Gly Val Gln Arg Val Gly
    290                 295                 300

Asn Leu Leu Gly Met Val Thr Arg Ala Gly Lys Gln Leu Phe Val Pro
305                 310                 315                 320

Arg Val Tyr Tyr Asn Glu Leu Ser Ser Ile Phe Glu Ser Pro Asp Val
                325                 330                 335

Leu Glu Met Glu Pro Ile Ile Ile Glu Asp Ser Gly Pro Pro Ile Glu
            340                 345                 350

Asp Glu Ala Ile Pro Gly Ala Pro Ala Gly Val Phe Pro Gln Gly Asn
        355                 360                 365

Arg Pro Tyr Ala Tyr Asn Gly Tyr Leu Phe Gly Pro Ile Pro Val Asp
    370                 375                 380

Val Ser Ile Lys Val Ser Gly Thr Gly Phe Ile Pro Met Pro Val Thr
385                 390                 395                 400

Val Ser Gly Asn Thr Ile Phe Pro Leu Tyr Pro Ser Phe Asp Lys Ser
                405                 410                 415

Thr Pro Leu Tyr Pro Pro Arg His Val Phe Phe Ser Asp Leu Asp Asp
            420                 425                 430

Pro Ile Met Phe Lys Arg Arg Lys Lys Cys Phe Ala Asp Gly Cys Val
        435                 440                 445

Asp Ala Phe Tyr
    450

<210> SEQ ID NO 23
<211> LENGTH: 506
<212> TYPE: PRT
<213> ORGANISM: Artificial Sequence
<220> FEATURE:
<223> OTHER INFORMATION: CcrPV_L1

<400> SEQUENCE: 23

Met Ala Val Trp Leu Pro Ala Gln Asn Lys Phe Tyr Leu Pro Pro Gln
1               5                   10                  15

Pro Ser Thr Arg Val Leu Ser Thr Asp Glu Tyr Val Thr Arg Thr Ser
            20                  25                  30

Ile Phe Tyr His Ala Ser Thr Asp Arg Leu Leu Thr Val Gly His Pro
        35                  40                  45

Tyr Phe Asp Ile Tyr His Glu Asn Lys Lys Asp Ile Ile Val Pro Lys
    50                  55                  60

Val Ser Pro Asn Ala Tyr Arg Val Phe Arg Leu Lys Leu Pro Asp Pro
65                  70                  75                  80
```

-continued

```
Asn Asn Phe Ala Phe Gly Asp Lys Ser Ile Phe Asp Pro Glu Lys Glu
                85                  90                  95

Arg Leu Val Trp Ala Leu Arg Gly Val Glu Ile Asp Arg Gly Gln Pro
            100                 105                 110

Leu Gly Cys Gly Ile Thr Gly His Pro Ile Phe Asn Lys Phe Ala Asp
        115                 120                 125

Val Glu Asn Ala Lys Asn Val Gly Thr Gly His Asp Ala Met Asn Ala
    130                 135                 140

Ile Gly Ser Asn Thr Ala Phe Asp Pro Lys Gln Thr Gln Met Phe Leu
145                 150                 155                 160

Ile Gly Cys Lys Pro Ala Leu Gly Glu His Trp Ser Arg Ala Ala Trp
                165                 170                 175

Cys Lys Asn Asn Glu Gly Gly Leu Gly His Lys Asp Thr Asp Cys
            180                 185                 190

Pro Pro Ile Glu Leu Lys Thr Thr Ser Ile Glu Asp Gly Asp Met Val
        195                 200                 205

Asp Ile Gly Phe Gly Ala Met Asp Phe Asn Asp Leu Gln Gln Asp Lys
    210                 215                 220

Thr Ser Val Pro Leu Asp Ile Tyr Lys Ser Lys Cys Lys Tyr Pro Asp
225                 230                 235                 240

Tyr Ile Lys Met Ala Asn Asp Pro Tyr Gly Asp Phe Cys Phe Phe Tyr
                245                 250                 255

Val Arg Arg Glu Gln Met Tyr Ala Arg His Tyr Phe Thr Arg Tyr Gly
            260                 265                 270

Lys Ile Ser Glu Lys Glu Gln Gly Asp Thr Leu Glu Asp Asp Asn Pro
        275                 280                 285

Pro Leu Ser Thr Asn Asn Tyr Phe Thr Ser Pro Ser Gly Ser Leu Val
        290                 295                 300

Ser Ser Glu Gly Gln Leu Phe Asn Arg Pro Tyr Trp Ile Gln Arg Ser
305                 310                 315                 320

Gln Gly Gln Asn Asn Gly Ile Ala Trp Asn Asn Gln Leu Phe Leu Thr
                325                 330                 335

Val Val Asp Asn Thr Arg Gly Thr Ala Leu Asn Ile Ile Val Gly Gln
            340                 345                 350

Asn Gly Thr Pro Asn Gln Gly Ala Phe Lys Ala Asn Glu Tyr Tyr Thr
        355                 360                 365

Tyr Leu Arg His Val Glu Glu Phe Asp Ile Ser Val Ile Leu Gln Leu
    370                 375                 380

Cys Lys Val Arg Leu Thr Pro Glu Asn Leu Ala Ile Ile His Thr Met
385                 390                 395                 400

Asp Pro Asn Ile Ile Glu Ala Trp His Leu Asn Val Asn Pro Pro Ser
                405                 410                 415

Gly Ile Leu Asp Glu Thr Tyr Arg Tyr Ile His Ser Met Ala Thr Lys
            420                 425                 430

Cys Pro Ser Asn Val Pro Pro Ser Glu Lys Glu Asp Pro Tyr Ser Lys
        435                 440                 445

Leu Lys Phe Trp Glu Val Asp Leu Arg Asp Arg Leu Thr Glu Gln Leu
    450                 455                 460

Asp Gln Thr Pro Leu Gly Arg Lys Phe Leu Phe Gln Thr Asn Val Ile
465                 470                 475                 480
```

Arg Gly Gly Val Lys Arg Pro Arg Val Val Thr Thr Ser Ser Lys Ala
              485                 490                 495

Lys Pro Val Lys Arg Arg Gly Asn Lys
            500                 505

<210> SEQ ID NO 24
<211> LENGTH: 534
<212> TYPE: PRT
<213> ORGANISM: Artificial Sequence
<220> FEATURE:
<223> OTHER INFORMATION: CcrPV1_L2

<400> SEQUENCE: 24

Met His Ala Arg Arg Lys Arg Ala Ala Pro Lys Asp Ile Tyr Pro Ser
1               5                   10                  15

Cys Lys Ile Ser Asn Asn Cys Pro Asp Asp Ile Arg Asn Lys Ile Glu
            20                  25                  30

His Asn Thr Leu Ala Asp Lys Ile Leu Lys Trp Gly Ser Ala Gly Val
        35                  40                  45

Phe Phe Gly Ser Leu Gly Ile Gly Thr Gly Arg Gly Thr Gly Ser Tyr
    50                  55                  60

Val Pro Leu Gly Ser Gly Val Asn Val Gly Thr Arg Val Ser Thr Val
65                  70                  75                  80

Lys Pro Ser Ile Pro Ile Ser Ser Val Gly Thr Ala Asp Val Ile Pro
                85                  90                  95

Val Asp Ala Met Asn Pro Leu Gly Pro Ala Leu Ala Pro Lys Phe
            100                 105                 110

Pro Thr Ala Val Glu Asp Pro Val Ile Ile Arg Pro Pro Lys Phe Pro
        115                 120                 125

Ser Ile Val Glu Asp Pro Val Ile Val His Ser Ala Ala Glu His Pro
    130                 135                 140

Ala Val Leu Asp Pro Asp His Ile Ala Val Asp Ile Ser Gly Glu
145                 150                 155                 160

Thr Val Gln Glu Ile Pro Tyr Thr Thr Ser Asn Val Val Thr Glu Glu
                165                 170                 175

Gln Pro Ala Val Leu Asp Val Ser Thr Glu Thr Arg Ala Pro Lys Ile
            180                 185                 190

Ile Ser Arg Thr Gln Tyr Glu Asn Pro Ser Phe Glu Val Ala Ile Thr
        195                 200                 205

Ser Asn Ala Thr Ala Gly Glu Thr Ser Ala Thr Asp His Ile Leu Val
    210                 215                 220

Asp Gly Tyr Ser Gly Gly Gln His Ile Gly Glu Gln Ile Glu Leu Gln
225                 230                 235                 240

Glu Leu Ala Arg Arg Ser Phe Ser Thr Thr Ile Glu Glu Thr Ser
                245                 250                 255

Phe Leu Thr Ser Thr Pro Asn Glu Ala Val Val Arg Pro Lys Thr Arg
            260                 265                 270

Asn Leu Asn Ser Arg Arg Tyr Leu Gln Thr Gln Val Thr Asp Pro Ala
        275                 280                 285

Phe Val Thr Gln Pro Arg Ser Leu Val Thr Phe Gln Asn Pro Ala Phe
    290                 295                 300

Asp Glu Ser Val Asp Leu Ile Phe Glu Lys Asp Val Ala Asp Phe Pro
305                 310                 315                 320

Leu Ala Ala Pro Asn Glu Asp Phe Arg Asp Leu Ile Ser Leu Ser Lys
                325                 330                 335

```
Pro Ile Tyr His Arg Ser Asn Glu Asn Thr Val Arg Val Ser Arg Phe
            340                 345                 350

Gly Thr Lys Ala Ser Val Lys Thr Arg Ser Gly Val Ile Ala Gly Pro
        355                 360                 365

Gln Ile His Tyr Phe Tyr Asp Leu Ser Glu Ile Ala Pro Ala Asp Asn
    370                 375                 380

Ile Glu Leu Ala Thr Leu Gly Ser Ser Pro Val Gly Glu Gln Ser Gly
385                 390                 395                 400

Glu Ser Val Ile Ser Ser Gly Thr Thr Asp Met Glu Ile Ile Ser Leu
                405                 410                 415

Thr Gly Ser Thr Leu Glu Ser Tyr Ser Asp Glu Ser Leu Leu Asp Ile
            420                 425                 430

Tyr Glu Pro Ile Ala Asn Asp Leu Gln Leu Val Ile Gly Ile Gly Arg
        435                 440                 445

Arg Val Arg Pro Ile Ser Val Pro Asp Leu Leu Thr Thr Lys Phe Gln
    450                 455                 460

Ile Phe Pro Gly Phe Glu Gly Val His Val His Thr Ser Ser Ser Asn
465                 470                 475                 480

Glu Thr Pro Lys Ile Pro Ile Asn Pro Leu Glu Thr Pro Ala Val Val
                485                 490                 495

Ile Asp Leu Leu Gly Gly Thr Asp Phe Tyr Leu His Pro Ala Leu Phe
            500                 505                 510

Lys Lys Lys Lys Lys Arg Leu Phe Cys Asp Phe Phe Ala Asp Gly Gly
        515                 520                 525

Val Ala Ser Cys Thr Glu
    530

<210> SEQ ID NO 25
<211> LENGTH: 506
<212> TYPE: PRT
<213> ORGANISM: Artificial Sequence
<220> FEATURE:
<223> OTHER INFORMATION: CgPV1_L1

<400> SEQUENCE: 25

Met Ala Met Trp Arg Pro Ser Asp Asn Lys Val Phe Leu Pro Pro Ala
1               5                   10                  15

Thr Pro Val Ser Lys Val Leu Ser Thr Asp Asp Tyr Val Ser Arg Thr
            20                  25                  30

Thr Ile Tyr Tyr Tyr Ala Gly Ser Ser Arg Leu Leu Thr Val Gly His
        35                  40                  45

Pro Tyr Phe Pro Ile Lys Lys Ser Gly Gly Arg Asn Ser Leu Leu Val
    50                  55                  60

Pro Lys Val Ser Gly Tyr Gln Tyr Arg Val Phe Arg Val Arg Leu Pro
65                  70                  75                  80

Asp Pro Asn Lys Phe Gly Leu Pro Glu Gly Ser Leu Tyr Asn Pro Glu
                85                  90                  95

Thr Gln Arg Leu Val Trp Ala Cys Arg Gly Val Glu Val Gly Arg Gly
            100                 105                 110

Gln Pro Leu Gly Val Gly Thr Ser Gly His Pro Leu Ser Ile Asp Leu
        115                 120                 125

Glu Asp Thr Lys Asn Ser Thr Leu Phe Asp Gly Ala Pro Gly Asn Asp
    130                 135                 140

Ser Arg Asp Asn Val Ser Met Asp Tyr Lys Gln Thr Gln Leu Phe Ile
145                 150                 155                 160
```

Ile Gly Cys Lys Pro Leu Gly Glu His Trp Ala Lys Gly Thr Pro
         165                 170                 175

Cys Asn Ser Ser Thr Val Asn Ala Gly Asp Cys Pro Pro Leu Glu Leu
         180                 185                 190

Ala Ser Thr Thr Ile Gln Asp Gly Asp Met Val Asp Thr Gly Phe Gly
         195                 200                 205

Ala Met Asp Phe Ala Ala Leu Gln Ser Asn Lys Ser Asp Val Pro Leu
    210                 215                 220

Asp Ile Leu Asn Ala Thr Cys Lys Tyr Pro Asp Tyr Leu Gln Met Ala
225                 230                 235                 240

Ala Glu Pro Tyr Gly Asp Lys Met Phe Phe Ser Leu Arg Arg Glu Gln
                245                 250                 255

Met Phe Val Arg His Phe Tyr Asn Arg Ala Gly Thr Met Gly Glu Ser
            260                 265                 270

Val Pro Glu Glu Leu Ile Leu Lys Gly Ala Pro Ser Ser Arg Ala
        275                 280                 285

Thr Pro Gly Ser Ser Ile Tyr Ala Ser Thr Pro Ser Gly Ser Met Val
    290                 295                 300

Ser Ser Glu Ser Gln Leu Phe Asn Lys Pro Tyr Trp Leu Gln Arg Ala
305                 310                 315                 320

Gln Gly Arg Asn Asn Gly Ile Cys Trp Gly Asn Gln Val Phe Leu Thr
                325                 330                 335

Val Val Asp Thr Thr Arg Ser Thr Asn Leu Thr Val Cys Ala Thr Ala
            340                 345                 350

Thr Ser Glu Thr Thr Tyr Lys Ala Ser Asn Phe Lys Glu Tyr Leu Arg
        355                 360                 365

His Gly Glu Glu Phe Asp Leu Gln Phe Ile Phe Gln Leu Cys Val Val
    370                 375                 380

Asn Leu Thr Ala Glu Val Met Thr Tyr Ile His Gly Met Asp Pro Ser
385                 390                 395                 400

Leu Leu Glu Asp Trp Asn Phe Gly Thr Leu Pro Pro Ser Ala Ser
                405                 410                 415

Leu Gly Asp Thr Tyr Arg Phe Leu Gln Ser Gln Ala Ile Thr Cys Gln
            420                 425                 430

Arg Pro Pro Ala Pro Glu Lys Asp Lys Gln Asp Pro Tyr Ala Gly Leu
        435                 440                 445

Thr Phe Trp Glu Val Asp Leu Thr Glu Arg Phe Ser Val Asp Leu Asp
    450                 455                 460

Gln Phe Pro Leu Gly Arg Lys Phe Leu Leu Gln Thr Gly Gly Arg Pro
465                 470                 475                 480

Arg Ala Ala Ala Ser Arg Lys Arg Thr Ala Pro Ala Ala
                485                 490                 495

Pro Ala His Lys Arg Lys Lys Thr Lys Arg
            500                 505

<210> SEQ ID NO 26
<211> LENGTH: 466
<212> TYPE: PRT
<213> ORGANISM: Artificial Sequence
<220> FEATURE:
<223> OTHER INFORMATION: CgPV1_L2

<400> SEQUENCE: 26

Met Val Ala Arg Ala Arg Arg Lys Arg Ala Ser Ala Thr Gln Leu
1               5                  10                  15

```
Tyr Gln Thr Cys Lys Ala Ala Gly Thr Cys Pro Pro Asp Ile Ile Pro
             20                  25                  30
Lys Ile Glu His Ser Thr Val Ala Asp Asn Ile Leu Lys Tyr Gly Ser
             35                  40                  45
Leu Gly Ile Phe Leu Gly Gly Leu Gly Ile Gly Thr Gly Ser Gly Thr
         50                  55                  60
Gly Gly Arg Thr Gly Tyr Ile Pro Val Gly Ser Arg Pro Pro Thr Val
65                  70                  75                  80
Val Asp Val Gly Pro Val Ala Arg Pro Pro Val Val Ile Glu Pro Val
                 85                  90                  95
Gly Ala Ser Asp Pro Ser Ile Val Thr Leu Val Glu Ser Ser Ile
                100                 105                 110
Ile Gln Ala Gly Ala Ala His Pro Asn Phe Thr Gly Ser Gly Gly Phe
            115                 120                 125
Glu Val Thr Thr Ser Gly Thr Thr Thr Pro Ala Val Leu Asp Ile Thr
130                 135                 140
Pro Ala Gly Gly Gly Val Gln Ile Ser Ser Ser Ser Phe Ser Asn Pro
145                 150                 155                 160
Leu Phe Thr Glu Pro Gln Phe Val Glu Ala Pro Gln Thr Gly Glu Val
                165                 170                 175
Ser Gly His Ile Leu Ile Ser Thr Pro Thr Ser Gly Ala His Gly Tyr
            180                 185                 190
Glu Glu Ile Pro Met Val Thr Phe Ala Gln Glu Gly Ser Gly Leu Glu
        195                 200                 205
Pro Ile Ser Ser Thr Pro Leu Pro Gly Val Arg Arg Leu Ala Gly Pro
    210                 215                 220
Arg Leu Tyr Ser Arg Ala Tyr Gln Gln Val Arg Val Asp Asp Pro Gln
225                 230                 235                 240
Phe Val Ser Gln Pro Ala Thr Phe Val Thr Tyr Asp Asn Pro Val Tyr
                245                 250                 255
Asp Pro Glu Glu Thr Ile Leu Phe Asp Arg Thr Gly Leu His Asp Pro
            260                 265                 270
Pro Asp Pro Asp Phe Leu Asp Ile Val Ala Leu His Arg Pro Ala Leu
        275                 280                 285
Arg Ala Thr Arg Gln Gly Ser Val Arg Phe Ser Arg Leu Gly Arg Arg
    290                 295                 300
Ala Thr Leu Arg Thr Arg Ser Gly Lys Thr Ile Gly Ala Arg Val His
305                 310                 315                 320
Phe Tyr His Asp Leu Ser Pro Ile Ser Ala Ala Asp Asn Ile Glu Leu
                325                 330                 335
Gln Pro Leu Leu Pro Val Asp Pro Ser Gly Val Thr Pro Asp Glu Pro
            340                 345                 350
Val Tyr Asp Ile Phe Ala Asp Pro Asp Ala Leu Gln Gln Ala Ala Pro
        355                 360                 365
Ser Gln Arg Ser Ser Leu Ser Val Tyr Arg Pro Ser Val Val Ala Leu
    370                 375                 380
Ser Ala Thr Ser Ser His Pro Ser Thr Val Pro Leu Ser Ala Gly Val
385                 390                 395                 400
Asp Ala Pro Val Phe Ser Gly Pro Asp Val Asp Ile Pro Gly Ala Ser
                405                 410                 415
Pro Trp Pro Gln Pro Val Pro His Thr Thr Pro Gln His Ser Ile
            420                 425                 430
```

```
Tyr Val His Gly Thr Asp Phe Tyr Leu Pro Gly Tyr Leu Phe Val
            435                 440                 445

Pro Lys Arg Arg Lys Arg Phe Ile Tyr Ser Phe Ala Asp Gly Tyr Val
    450                 455                 460

Ala Ala
465

<210> SEQ ID NO 27
<211> LENGTH: 496
<212> TYPE: PRT
<213> ORGANISM: Artificial Sequence
<220> FEATURE:
<223> OTHER INFORMATION: MfPV6_L1

<400> SEQUENCE: 27

Met Ser Leu Trp Arg Pro Ser Asp Ser Lys Val Tyr Leu Pro Pro Ala
1               5                   10                  15

Pro Val Ser Lys Val Val Ser Thr Asp Glu Tyr Val Thr Arg Thr Ser
            20                  25                  30

Ile Tyr Tyr His Ala Ala Ser Ser Arg Leu Leu Ala Val Gly His Pro
        35                  40                  45

Tyr Tyr Ala Val Lys Lys Gly Asn Lys Val Thr Val Pro Lys Val Ser
    50                  55                  60

Gly Leu Gln Tyr Arg Val Phe Arg Val Arg Leu Pro Asp Pro Asn Lys
65                  70                  75                  80

Phe Gly Leu Pro Asp Ala Asn Phe Tyr Asp Pro Asn Thr Gln Arg Leu
                85                  90                  95

Val Trp Ala Cys Ile Gly Leu Glu Val Gly Arg Gly Gln Pro Leu Gly
            100                 105                 110

Val Gly Thr Ser Gly His Pro Leu Leu Asn Lys Leu Asp Asp Thr Glu
        115                 120                 125

Asn Gly Pro Lys Val Ala Ala Gly Gln Gly Val Asp Asn Arg Glu Cys
130                 135                 140

Val Ser Met Asp Tyr Lys Gln Thr Gln Leu Cys Leu Leu Gly Cys Lys
145                 150                 155                 160

Pro Pro Val Gly Glu His Trp Gly Lys Gly Asn Pro Cys Ser Ala Gly
                165                 170                 175

Asn Ala Gly Asp Cys Pro Pro Leu Glu Leu Gln Asn Ser Val Ile Gln
            180                 185                 190

Asp Gly Asp Met Val Asp Thr Gly Tyr Gly Ala Met Asp Phe Ser Val
        195                 200                 205

Leu Gln Ala Asn Lys Cys Asp Val Pro Leu Asp Ile Cys Asn Ser Val
    210                 215                 220

Cys Lys Tyr Pro Asp Tyr Leu Lys Met Ala Ala Glu Pro Tyr Gly Asp
225                 230                 235                 240

Ser Leu Phe Phe Tyr Leu Arg Arg Glu Gln Met Phe Ala Arg His Met
                245                 250                 255

Phe Asn Arg Ala Gly Asn Ile Gly Asp Ala Val Pro Asp Glu Leu Tyr
            260                 265                 270

Ile Lys Gly Ser Gly Gln Lys Ala Ala Leu Pro Ser His Ile Phe Phe
        275                 280                 285

Pro Thr Pro Ser Gly Ser Met Val Thr Ser Glu Ala Gln Leu Phe Asn
    290                 295                 300

Lys Pro Tyr Trp Leu Gln Arg Ala Gln Gly His Asn Asn Gly Ile Cys
305                 310                 315                 320
```

```
Trp Gly Asn Gln Val Phe Leu Thr Val Val Asp Thr Thr Arg Ser Thr
                            325                 330                 335

Asn Met Thr Leu Cys Ala Ala Thr Gly Thr Asp Ser Thr Tyr Lys Asn
            340                 345                 350

Glu Asn Phe Lys Glu Tyr Met Arg His Val Glu Glu Tyr Asp Leu Gln
        355                 360                 365

Phe Ile Phe Gln Leu Cys Lys Ile Thr Leu Thr Thr Glu Val Met Ala
370                 375                 380

Tyr Ile His Asn Met Asp Ala Ser Ile Leu Glu Asp Trp Asn Phe Gly
385                 390                 395                 400

Leu Gln Ala Pro Pro Ser Gly Ser Leu Gln Asp Thr Tyr Arg Phe Val
                405                 410                 415

Thr Ser Ser Ala Ile Thr Cys Gln Lys Pro Ala Pro Lys Glu Lys
            420                 425                 430

Glu Asp Pro Leu Ala Lys Tyr Ala Phe Trp Asp Val Asn Leu Lys Glu
        435                 440                 445

Lys Phe Ser Ala Asp Leu Asp Gln Phe Pro Leu Gly Arg Lys Phe Leu
450                 455                 460

Leu Gln Ala Gly Met Arg Ala Arg Pro Thr Leu Lys Lys Arg Ser Ala
465                 470                 475                 480

Pro Ser Thr Ser Ser Thr Pro Ala Lys Arg Lys Arg Val Lys Arg
                485                 490                 495
```

<210> SEQ ID NO 28
<211> LENGTH: 477
<212> TYPE: PRT
<213> ORGANISM: Artificial Sequence
<220> FEATURE:
<223> OTHER INFORMATION: MfPV6_L2

<400> SEQUENCE: 28

```
Met Lys His Ala Arg Leu Ser Arg Arg Lys Arg Ala Thr Gln Gln Ser
1               5                   10                  15

Pro Pro Arg Ala Arg Arg Lys Arg Ala Ser Ala Thr Gln Leu Tyr Gln
                20                  25                  30

Thr Cys Lys Ala Ala Gly Thr Cys Pro Pro Asp Val Ile Pro Lys Val
            35                  40                  45

Glu Gly Ser Thr Val Ala Asp Gln Ile Leu Lys Tyr Gly Ser Met Gly
        50                  55                  60

Val Phe Phe Gly Gly Leu Gly Ile Gly Thr Gly Ser Gly Thr Gly Gly
65                  70                  75                  80

Arg Thr Gly Tyr Val Pro Leu Gly Ala Arg Pro Ser Val Val Pro Glu
                85                  90                  95

Val Leu Pro Arg Pro Pro Val Thr Val Glu Pro Val Ala Pro Thr Asp
                100                 105                 110

Pro Ser Ile Val Ser Leu Leu Glu Glu Ser Ser Leu Ile Glu Ala Gly
            115                 120                 125

Val Pro Ala Pro Ile Val Pro Thr His Gly Gly Phe Glu Val Thr Thr
        130                 135                 140

Ser Glu Thr Ser Thr Pro Ala Ile Leu Asp Val Ser Gln Gly Ser Ser
145                 150                 155                 160

Asn Val His Ile Ser Val Asn Thr Phe Asn Asn Pro Ala Phe Thr Glu
                165                 170                 175

Pro Ser Val Leu His Pro Pro Pro Val Glu Ala Ser Gly Arg Leu
            180                 185                 190
```

```
Val Ile Ser Ser Ser Thr Val Ser Thr Gln Asn Tyr Glu Glu Ile Pro
        195                 200                 205

Met Asp Thr Phe Val Ile Thr Gly Asp His Arg Phe Asn Thr Thr Ser
210                 215                 220

Thr Pro Ile Pro Gly Ser Arg Pro Ala Arg Leu Gly Leu Tyr Gly
225                 230                 235                 240

Arg Ala Leu Gln Gln Val Arg Val Asp Pro Ala Phe Leu Thr Thr
            245                 250                 255

Pro Ala Arg Leu Ile Thr Tyr Asp Asn Pro Val Tyr Glu Gly Val Asp
            260                 265                 270

Asp Ala Thr Leu Gln Phe Ser His Pro Thr Ile His Glu Pro Pro Asp
        275                 280                 285

Pro Asp Phe Leu Asp Ile Val Ala Leu His Arg Pro Ala Leu Thr Ser
290                 295                 300

Arg Arg Gly Thr Val Arg Phe Ser Arg Val Gly Gln Arg Ala Ser Met
305                 310                 315                 320

His Thr Arg Ser Gly Ala Arg Ile Gly Ala Arg Val His Tyr Phe Gln
                325                 330                 335

Asp Leu Ser Ser Ile Ala Pro Ala Glu Ala Thr Thr Glu Ser Ile Glu
            340                 345                 350

Met Gln Pro Leu Leu Pro Ala Ala Thr Gln Asp Ile Asp Leu Tyr Asp
        355                 360                 365

Ile Tyr Ala Val Asp Glu Asp Val Thr Ser Pro Ala Gln Pro Thr Leu
    370                 375                 380

Pro Phe Pro Ser Ser Thr Ala Ser Ala Val Asp Ala Thr Leu Pro Trp
385                 390                 395                 400

Thr Ser Thr Val Pro Leu Ser Thr Gly Leu Asp Ile Thr Leu Gln Pro
                405                 410                 415

Gly Pro Asp Ile Pro Leu Gln Phe Pro Leu Ala Glu Ser Pro Leu His
            420                 425                 430

Pro Val Thr Pro Leu Thr Pro Ile Gly His Val Val His Gly Gly
        435                 440                 445

Asp Phe Tyr Leu His Pro Ser Tyr Tyr Thr Leu His Lys Arg Arg Lys
450                 455                 460

Arg Met Pro Arg Phe Leu Ala Asp Val Ser Val Ala Ala
465                 470                 475

<210> SEQ ID NO 29
<211> LENGTH: 499
<212> TYPE: PRT
<213> ORGANISM: Artificial Sequence
<220> FEATURE:
<223> OTHER INFORMATION: MfPV11_L1

<400> SEQUENCE: 29

Met Ser Leu Trp Arg Pro Ser Asp Ala Lys Val Tyr Leu Pro Pro Ala
1               5                   10                  15

Pro Val Ser Lys Ala Ile Ser Thr Asp Glu Tyr Val Thr Arg Thr Ser
            20                  25                  30

Thr Tyr Tyr His Ala Gly Ser Ser Arg Leu Leu Ala Val Gly His Pro
        35                  40                  45

Tyr Tyr Pro Val Lys Lys Ser Asn Gly Lys Ile Ala Val Pro Lys Val
    50                  55                  60

Ser Gly Leu Gln Tyr Arg Val Phe Arg Val Lys Leu Pro Asp Pro Asn
65                  70                  75                  80
```

-continued

```
Lys Phe Gly Leu Pro Asp Ala Asn Phe Tyr Asp Pro Asn Thr Gln Arg
                 85                  90                  95

Leu Val Trp Ala Cys Ile Gly Met Glu Val Gly Arg Gly Gln Pro Leu
            100                 105                 110

Gly Val Gly Thr Ser Gly His Pro Leu Leu Asn Lys Leu Asp Asp Thr
        115                 120                 125

Glu Asn Ser His Asn Asn Gly Ala Asn Gln Gly Thr Asp Asn Arg Glu
    130                 135                 140

Cys Val Ser Met Asp Tyr Lys Gln Thr Gln Leu Cys Leu Leu Gly Cys
145                 150                 155                 160

Lys Pro Pro Thr Gly Glu His Trp Gly Lys Gly Thr Pro Cys Thr Ser
                165                 170                 175

Gly Ala Asp Gly Asp Cys Pro Pro Leu Glu Leu Ile Asn Ser Val Ile
            180                 185                 190

Gln Asp Gly Asp Met Val Asp Ala Gly Tyr Gly Cys Leu Asp Phe Gln
        195                 200                 205

Ala Leu Gln Thr Asn Lys Ser Asp Val Pro Leu Asp Ile Cys Met Ser
    210                 215                 220

Thr Cys Lys Tyr Pro Asp Tyr Leu Lys Met Ala Ser Glu Pro Tyr Gly
225                 230                 235                 240

Asp Arg Leu Phe Phe Phe Leu Arg Arg Glu Gln Met Phe Val Arg His
                245                 250                 255

Met Phe Asn Arg Ala Gly Thr Met Gly Glu Thr Leu Pro Ser Asp Leu
            260                 265                 270

Tyr Ile Lys Gly Thr Gly Asn Arg Ser Ser Leu Ala Ser His Ile Phe
        275                 280                 285

Ser Ser Thr Pro Ser Gly Ser Met Val Thr Ser Glu Ser Gln Leu Phe
    290                 295                 300

Asn Lys Pro Tyr Trp Leu Gln Arg Ala Gln Gly His Asn Asn Gly Ile
305                 310                 315                 320

Cys Trp Gly Asn Gln Val Phe Leu Thr Val Val Asp Thr Thr Arg Ser
                325                 330                 335

Thr Asn Val Thr Leu Cys Ala Thr Lys Thr Ser Glu Asp Thr Tyr Lys
            340                 345                 350

Asn Asp Asn Phe Arg Glu Tyr Leu Arg His Met Glu Glu Phe Asp Leu
        355                 360                 365

Gln Phe Val Phe Gln Leu Cys Lys Ile Thr Leu Thr Thr Glu Val Met
    370                 375                 380

Ala Tyr Ile His Asn Met Asp Pro Ser Ile Leu Glu Asp Trp Asn Phe
385                 390                 395                 400

Gly Val Gln Pro Pro Pro Ala Gly Thr Leu Gln Asp Thr Tyr Arg Phe
                405                 410                 415

Val Gln Ser Glu Ala Ile Arg Cys Gln Lys Thr Ala Ala Pro Lys Val
            420                 425                 430

Lys Glu Asp Pro Leu Ser Lys Tyr Thr Phe Trp Asp Val Asp Leu Arg
        435                 440                 445

Asp Lys Phe Ser Ala Asp Leu Asp Gln Phe Pro Leu Gly Arg Lys Phe
    450                 455                 460

Leu Leu Gln Ala Gly Met Arg Ala Arg Ser Thr Leu Arg Ala Pro Lys
465                 470                 475                 480

Arg Pro Ala Pro Thr Thr Ser Ser Gly Ser Ser Lys Lys Arg Lys Thr
                485                 490                 495

Thr Arg Arg
```

<210> SEQ ID NO 30
<211> LENGTH: 475
<212> TYPE: PRT
<213> ORGANISM: Artificial Sequence
<220> FEATURE:
<223> OTHER INFORMATION: MfPV11_L2

<400> SEQUENCE: 30

```
Lys Leu Ala Thr Met Lys Gln Pro Ala Arg Ala Ser Arg Arg Arg
1               5                   10                  15

Asn Ala Asn Gly His Val His Arg Pro Arg Arg Lys Arg Ala Ser Ala
            20                  25                  30

Thr Gln Leu Tyr Gln Thr Cys Lys Ala Ala Gly Thr Cys Pro Pro Asp
                35                  40                  45

Val Ile Pro Lys Val Glu Gly Thr Thr Val Ala Asp Gln Ile Leu Arg
        50                  55                  60

Tyr Gly Ser Met Gly Val Tyr Phe Gly Gly Leu Gly Ile Gly Thr Ala
65                  70                  75                  80

Pro Gly Ser Gly Gly Arg Ser Gly Tyr Val Pro Leu Gly Ser Arg Pro
                85                  90                  95

Ala Thr Val Pro Glu Val Leu Pro Arg Pro Val Leu Val Glu Pro
                100                 105                 110

Val Ala Pro Ser Asp Pro Ser Ile Val Ser Leu Val Glu Glu Ala Asn
            115                 120                 125

Leu Ile Asp Ala Gly Leu Pro Ala Pro Ser Val Pro Thr Gly Gly Gly
        130                 135                 140

Phe Thr Val Thr Thr Ser Asp Val Ser Thr Pro Ala Ile Leu Pro Val
145                 150                 155                 160

Thr Pro Ala Glu Thr Ser Val His Val Thr Val Asp Thr Phe Thr Asn
                165                 170                 175

Pro Leu Phe Thr Glu Pro Ser Val Phe Thr Pro Pro Pro Met Glu
                180                 185                 190

Ala Thr Gly His Ile Val Leu Ser Ser Asp Thr Val Ser Ala His Ser
            195                 200                 205

Tyr Glu Glu Ile Pro Met Asp Thr Phe Val Val Thr Gly Asp Asn Ala
        210                 215                 220

Tyr Asn Pro Thr Ser Thr Pro Ile Pro Thr Pro Arg Pro Arg Ala Arg
225                 230                 235                 240

Leu Gly Leu Tyr Gly Arg Gly Met Gln Gln Val Arg Val Ser Asp Pro
                245                 250                 255

Ala Phe Leu Ser Ser Pro Ala Arg Leu Ile Thr Phe Asp Asn Pro Ala
            260                 265                 270

Tyr Glu Gly Leu Pro Glu Asp Ser Leu Gln Phe Glu His Ser Ser Ile
        275                 280                 285

His Gln Pro Pro Asp Pro Asp Phe Leu Asp Ile Val Ala Leu His Arg
    290                 295                 300

Pro Ala Leu Thr Ser Arg Gln Gly Thr Val Arg Tyr Ser Arg Val Gly
305                 310                 315                 320

Asn Arg Ala Thr Ile Arg Thr Arg Ser Gly Lys Gln Ile Gly Ala Arg
                325                 330                 335

Val His Phe Phe Gln Asp Ile Ser Ala Ile Pro His Pro Glu Glu Ile
            340                 345                 350

Glu Met Gln Pro Leu Val Ser Ala Gln Glu Pro Leu Phe Asp Val Tyr
        355                 360                 365
```

```
Ala Asp Leu Glu Asp Ala Pro Glu Val Glu Gly Thr Gly Ser Ala
    370                 375                 380

Thr Ser Ser Ser Val Pro Leu Gln Gly Ser Ala Thr Trp Asn Thr
385                 390                 395                 400

Thr Val Pro Leu Asn Thr Gly Leu Asp Ile Leu Val Gln Pro Gly Pro
                405                 410                 415

Asp Val Ala Gln Gln Phe Pro Val Ala Glu Ser Pro Tyr Trp Pro Ala
                420                 425                 430

Met Pro Val Phe Pro Gln Gly His Val Tyr Val Ser Gly Gly Asp Phe
            435                 440                 445

Leu Trp His Pro Ser Leu Tyr Thr Pro Arg Arg Lys Arg Lys Arg Val
    450                 455                 460

His Thr Phe Phe Ala Asp Val Ser Val Ala Ala
465                 470                 475

<210> SEQ ID NO 31
<211> LENGTH: 501
<212> TYPE: PRT
<213> ORGANISM: Artificial Sequence
<220> FEATURE:
<223> OTHER INFORMATION: MmPv1_L1

<400> SEQUENCE: 31

Met Ser Met Trp Arg Pro Ser Asp Ser Lys Val Tyr Leu Pro Pro Val
1               5                   10                  15

Pro Val Ser Lys Val Val Ser Thr Asp Glu Tyr Val Ser Arg Thr Ser
                20                  25                  30

Ile Tyr Tyr His Ala Gly Ser Ser Arg Leu Leu Ala Val Gly His Pro
            35                  40                  45

Tyr Tyr Ala Val Lys Lys Gly Asn Asn Lys Val Ser Val Pro Lys Val
        50                  55                  60

Ser Gly Leu Gln Tyr Arg Val Phe Arg Val Arg Leu Pro Asp Pro Asn
65                  70                  75                  80

Lys Phe Gly Leu Pro Asp Ala Asn Phe Tyr Asp Pro Asn Thr Gln Arg
                85                  90                  95

Leu Val Trp Ala Cys Leu Gly Val Glu Val Gly Arg Gly Gln Pro Leu
            100                 105                 110

Gly Val Gly Thr Ser Gly His Pro Leu Leu Asn Lys Leu Asp Asp Thr
        115                 120                 125

Glu Asn Gly Pro Lys Leu Ala Gly Gly Gln Ala Asp Asn Arg Glu
    130                 135                 140

Cys Val Ser Met Asp Tyr Lys Gln Thr Gln Leu Cys Met Leu Gly Cys
145                 150                 155                 160

Lys Pro Pro Val Gly Glu His Trp Gly Lys Gly Asn Pro Cys Thr Thr
                165                 170                 175

Ala Ala Ala Gly Asp Cys Pro Ala Leu Glu Leu Val Asn Ser Val Ile
            180                 185                 190

Gln Asp Gly Asp Met Val Asp Thr Gly Tyr Gly Ala Met Asp Phe Asn
        195                 200                 205

Ala Leu Gln Ala Asn Lys Ser Asp Val Pro Ile Asp Ile Cys Thr Ser
    210                 215                 220

Val Cys Lys Tyr Pro Asp Tyr Leu Lys Met Ala Ser Asp Pro Tyr Gly
225                 230                 235                 240

Asp Ser Leu Phe Phe Tyr Leu Arg Arg Glu Gln Met Phe Val Arg His
                245                 250                 255
```

-continued

Leu Phe Asn Arg Ala Gly Thr Met Gly Asp Ser Val Pro Asp Asp Leu
            260                 265                 270

Tyr Ile Lys Gly Ser Gly Ser Asn Val Lys Leu Ala Ser His Val Phe
            275                 280                 285

Tyr Pro Thr Pro Ser Gly Ser Met Val Thr Ser Asp Ala Gln Leu Phe
            290                 295                 300

Asn Lys Pro Tyr Trp Leu Gln Lys Ala Gln Gly His Asn Asn Gly Ile
305                 310                 315                 320

Cys Trp Gly Asn Gln Val Phe Leu Thr Val Val Asp Thr Thr Arg Ser
            325                 330                 335

Thr Asn Met Thr Leu Cys Ala Ser Thr Ala Ser Thr Val Thr Thr Pro
            340                 345                 350

Tyr Asn Asn Glu Ser Phe Lys Glu Tyr Leu Arg His Val Glu Glu Phe
            355                 360                 365

Asp Leu Gln Phe Ile Phe Gln Leu Cys Lys Val Thr Leu Asn Thr Glu
            370                 375                 380

Val Met Ala Tyr Ile His Ser Met Asp Ala Ser Ile Leu Glu Asp Trp
385                 390                 395                 400

Asn Phe Gly Leu Gln Pro Pro Ser Gly Ser Leu Gln Asp Thr Tyr
            405                 410                 415

Arg Phe Val Thr Ser Ala Ala Ile Thr Cys Gln Lys Pro Ala Pro Pro
            420                 425                 430

Lys Glu Lys Glu Asp Pro Leu Ala Lys Tyr Thr Phe Trp Glu Val Asp
            435                 440                 445

Leu Lys Glu Lys Phe Ser Ala Asp Leu Asp Gln Phe Pro Leu Gly Arg
450                 455                 460

Lys Phe Leu Leu Gln Ala Gly Met Arg Ala Arg Pro Thr Leu Arg Ala
465                 470                 475                 480

Pro Lys Arg Thr Ala Ser Ser Thr Ser Ser Ser Pro Arg Lys Arg
            485                 490                 495

Lys Arg Thr Lys Arg
            500

<210> SEQ ID NO 32
<211> LENGTH: 466
<212> TYPE: PRT
<213> ORGANISM: Artificial Sequence
<220> FEATURE:
<223> OTHER INFORMATION: MmPV1_L2

<400> SEQUENCE: 32

Met Lys His Ala His Val Ser Arg Arg Lys Arg Ala Ala Pro Arg Pro
1               5                   10                  15

Pro Gly Gly Arg Gln Lys Arg Ala Ser Ala Thr Gln Leu Tyr Gln Thr
            20                  25                  30

Cys Lys Ala Ala Gly Thr Cys Pro Pro Asp Val Ile Pro Lys Val Glu
            35                  40                  45

Gly Thr Thr Val Ala Asp Gln Ile Leu Lys Tyr Gly Ser Met Gly Val
        50                  55                  60

Tyr Phe Gly Gly Leu Gly Ile Gly Ser Gly Ala Gly Thr Gly Gly Arg
65                  70                  75                  80

Ser Gly Tyr Val Pro Leu Gly Ser Arg Pro Ala Ser Ile Pro Glu Pro
            85                  90                  95

Leu Pro Arg Pro Pro Val Thr Ile Glu Pro Val Gly Pro Ser Asp Pro
            100                 105                 110

```
Ser Ile Val Ser Leu Leu Glu Glu Ser Arg Leu Ile Glu Ala Gly Val
        115                 120                 125

Pro Ala Pro Thr Phe Pro Thr His Gly Gly Phe Glu Ile Ser Thr Ser
130                 135                 140

Glu Val Ser Thr Pro Ala Ile Leu Asp Val Ser Ser Gly Ser Asn
145                 150                 155                 160

Val His Val Ser Val Thr Thr Phe Thr Asn Pro Thr Phe Thr Glu Pro
                165                 170                 175

Ser Val Leu Arg Pro Pro Pro Val Glu Ala Ser Gly Arg Leu Val
                180                 185                 190

Ile Ser Ala Ser Ser Val Ser Thr His Ser Tyr Glu Glu Ile Pro Met
        195                 200                 205

Asp Thr Phe Val Ile Thr Gly Asp His Asn Tyr Asn Thr Thr Ser Thr
        210                 215                 220

Pro Ile Pro Gly Ser Arg Ala Pro Ala Arg Leu Gly Leu Tyr Gly Arg
225                 230                 235                 240

Ala Thr Gln Gln Val Arg Val Val Asp Pro Ala Phe Ile Thr Thr Pro
                245                 250                 255

Ala Arg Leu Val Thr Tyr Asp Asn Pro Ala Tyr Glu Gly Val Asp Asp
                260                 265                 270

Ala Thr Leu Gln Phe Ser His Ser Asp Ile His Gln Pro Pro Asp Pro
        275                 280                 285

Asp Phe Leu Asp Ile Val Ala Leu His Arg Pro Ala Leu Thr Ser Arg
        290                 295                 300

Lys Gly Thr Val Arg Phe Ser Arg Leu Gly Gln Arg Ala Thr Leu Thr
305                 310                 315                 320

Thr Arg Ser Gly Lys Arg Ile Gly Ala Lys Val His Phe Tyr His Asp
                325                 330                 335

Leu Ser Pro Ile Ala Pro Ala Glu Ser Ile Glu Leu Gln Pro Leu Ser
                340                 345                 350

Ser Gln Gly Glu Leu Tyr Asp Ile Tyr Ala Asp Val Asp Gly Gln Glu
        355                 360                 365

Asp Val Ala Ala Met Ala Asp Thr Pro Leu Asn Ser Asn Ser Ser Gly
370                 375                 380

Thr Ala Ser Pro Trp Asn Thr Thr Val Pro Leu Ser Ala Gly Ala Asp
385                 390                 395                 400

Val Thr Leu Gln Ser Gly Pro Asp Val Ser Leu Asp Ala Pro Val Ala
                405                 410                 415

Glu Ser Pro Val His Pro Gly Val Pro Leu Arg Pro Ser Ala His Ile
                420                 425                 430

Ile Leu Tyr Gly Gly Asp Phe Tyr Leu His Pro Ser Tyr Leu Gly Ile
        435                 440                 445

Arg Arg Lys Arg Lys Arg Met His Asn Phe Phe Ser Asp Val Tyr Val
        450                 455                 460

Ala Ala
465

<210> SEQ ID NO 33
<211> LENGTH: 500
<212> TYPE: PRT
<213> ORGANISM: Artificial Sequence
<220> FEATURE:
<223> OTHER INFORMATION: PcPV1_L1
```

<400> SEQUENCE: 33

```
Met Ala Val Trp Leu Pro Ala Gln Asn Lys Phe Tyr Leu Pro Pro Gln
1               5                   10                  15

Pro Thr Thr Arg Val Leu His Thr Asp Glu Tyr Val Thr Arg Thr Arg
            20                  25                  30

Ile Phe Tyr His Ala Ser Ser Asp Arg Leu Leu Thr Val Gly His Pro
        35                  40                  45

Phe Phe Asp Ile Tyr Lys Asn Gln Glu Ile Ile Val Pro Lys Val Ser
    50                  55                  60

Pro Asn Gln Tyr Arg Val Phe Arg Leu Arg Leu Pro Asp Pro Asn Asn
65                  70                  75                  80

Phe Ala Phe Gly Asp Lys Ser Leu Phe Asn Pro Glu Lys Glu Arg Leu
                85                  90                  95

Val Trp Ala Leu Arg Gly Leu Glu Ile Gly Arg Gly Gln Pro Leu Gly
            100                 105                 110

Val Gly Val Ser Gly Asn Pro Thr Phe Asp Arg Tyr Ser Asp Val Glu
        115                 120                 125

Asn Ala Asn Lys Asn Pro Thr Gly His Ala Asp Asn Ala Pro Asp Pro
130                 135                 140

Arg Val Asn Met Ala Val Asp Pro Lys Gln Thr Gln Met Phe Met Val
145                 150                 155                 160

Gly Cys Lys Pro Ala Leu Gly Glu His Trp Val Lys Ala Arg Trp Cys
                165                 170                 175

Asn Gly Ala Ala His Glu Ser Gln Gln Cys Pro Pro Ile Glu Leu Lys
            180                 185                 190

Asn Thr Pro Ile Glu Asp Gly Asp Met Val Asp Ile Gly Phe Gly Ala
        195                 200                 205

Met Asp Phe Lys Asn Leu Gln Gln Asn Arg Ser Ala Val Pro Leu Asp
    210                 215                 220

Ile Ile Asp Thr His Cys Lys Tyr Pro Asp Tyr Ile Lys Met Ala Asn
225                 230                 235                 240

Asp Pro Tyr Gly Asp Thr Cys Phe Phe Val Arg Arg Glu Gln Leu
                245                 250                 255

Tyr Ala Arg His Leu Leu Ala Arg Ser Gly Gln Val Gly Glu Pro Glu
            260                 265                 270

Pro Glu Arg Thr Val Ala Thr Arg Ser Thr Tyr Pro Thr Leu Asn Tyr
        275                 280                 285

Phe Ser Ser Pro Ser Gly Ser Leu Val Ser Ser Glu Ala Gln Leu Phe
    290                 295                 300

Asn Arg Pro Tyr Trp Ile Gln Arg Ser Gln Gly Gln Asn Asn Gly Ile
305                 310                 315                 320

Ala Trp Glu Asn Gln Leu Phe Leu Thr Val Ala Asp Asn Thr Arg Gly
                325                 330                 335

Thr Pro Leu Thr Ile Asn Val Gly Pro Asn Asp Arg Ala Glu Asp Gly
            340                 345                 350

Glu Tyr Lys Ala Gly Ser Tyr Lys Thr Tyr Leu Arg His Val Glu Glu
        355                 360                 365

Phe Asp Ile Ser Val Ile Leu Gln Leu Cys Lys Val Gln Leu Thr Pro
    370                 375                 380

Glu Asn Leu Ala Thr Ile His Thr Met Asn Pro Asp Ile Ile Glu Ser
385                 390                 395                 400
```

```
Trp His Leu Asn Val Asn Pro Pro Ser Gly Ala Leu Asp Asp Thr Tyr
                405                 410                 415

Arg Tyr Ile Thr Ser Leu Ala Thr Lys Cys Pro Thr Asn Val Pro Pro
            420                 425                 430

Lys Glu Arg Glu Asp Pro Tyr Ala His Leu Lys Phe Trp Glu Val Asp
        435                 440                 445

Leu Arg Asp Lys Leu Thr Glu Gln Leu Asp Gln Thr Pro Leu Gly Arg
    450                 455                 460

Lys Phe Leu Phe Gln Thr Asn Val Leu Gln Gly Gly Ser Lys Arg
465                 470                 475                 480

Ala Arg Val Thr Thr Ser Val Ser Lys Asp Lys Pro Val Lys Arg Arg
                485                 490                 495

Arg Gly Gln Lys
            500

<210> SEQ ID NO 34
<211> LENGTH: 515
<212> TYPE: PRT
<213> ORGANISM: Artificial Sequence
<220> FEATURE:
<223> OTHER INFORMATION: PcPV1_L2

<400> SEQUENCE: 34

Met Leu Leu Lys Arg Arg Lys Arg Ala Ala Pro Lys Asp Ile Tyr Pro
1               5                   10                  15

Gln Cys Lys Ile Ser Asn Thr Cys Pro Pro Asp Val Leu Asn Lys Ala
            20                  25                  30

Glu Gln Ser Thr Leu Ala Asp Lys Ile Leu Lys Tyr Gly Ser Ala Gly
        35                  40                  45

Val Phe Leu Gly Ser Leu Gly Ile Gly Thr Gly Arg Gly Ser Gly Gly
    50                  55                  60

Thr Leu Gly Tyr Val Pro Val Gly Thr Gly Gln Gly Val Arg Leu Gly
65                  70                  75                  80

Thr Arg Val Ser Thr Val Arg Pro Ser Leu Pro Ile Ser Ser Val Gly
                85                  90                  95

Thr Ala Asp Val Ile Pro Ile Asp Ala Val Asp Pro Leu Gly Pro Ala
            100                 105                 110

Val Leu Pro Gly Asn Val Phe Pro Thr Ala Val Glu Asp Pro Phe Thr
        115                 120                 125

Ile Gln Pro Pro Arg Phe Pro Ser Ile Val Glu Glu Pro Val Ser Val
    130                 135                 140

His Ser Glu Ser Ile Val Thr Glu Ser Val Thr Glu Val Pro Val Asn
145                 150                 155                 160

Thr Pro Lys Val Thr Ile Asp Gly Gln Pro Ala Val Leu Glu Val Val
                165                 170                 175

Pro Glu Thr Arg Glu Pro Arg Ile Leu Ser Arg Ser Gln Tyr Gly Asn
            180                 185                 190

Ser Ala Phe Glu Val Ser Leu Thr Ala Ser Ala Gly Ser Gly Glu Thr
        195                 200                 205

Ser Ser Ser Asp His Ile Leu Val His Gly Phe Thr Gly Gly His Val
    210                 215                 220

Ile Gly Glu Gln Ile Pro Leu Gln Glu Leu Gly Gly Arg Ser Phe Ser
225                 230                 235                 240

Ser Thr Leu Glu Ala Glu Thr Thr Phe Thr Thr Ser Thr Pro Lys Ala
                245                 250                 255
```

```
Asp Ala Val Ala Glu Pro Arg Arg Val Phe Thr Ser Arg Arg Leu Glu
        260                 265                 270

Gln Ile Pro Val Arg Asp Pro Gly Phe Ile Ser Arg Pro Arg Ser Leu
    275                 280                 285

Val Thr Phe Gln Asn Pro Thr Phe Asp Glu Ser Val Asp Leu Phe Phe
290                 295                 300

Glu Arg Asp Val Ala Glu Leu Ala Leu Ala Ala Pro Asn Glu Asp Phe
305                 310                 315                 320

Arg Asp Leu Val Ser Leu Ser Lys Pro Thr Phe Ser Arg Thr Leu Glu
                325                 330                 335

Gly Arg Val Arg Val Ser Arg Leu Gly Thr Lys Ala Thr Met Arg Thr
                340                 345                 350

Arg Ser Gly Leu Val Ile Gly Pro Gln Ser His Tyr Tyr Tyr Asp Leu
                355                 360                 365

Ser Asp Ile Ala Pro Ala Glu Asn Leu Glu Leu Thr Pro Ile Gly Asn
    370                 375                 380

Met Ser Leu Gly Glu Gln Ser Gly Gln Ala Val Ile Ser Ser Gly Thr
385                 390                 395                 400

Ser Asp Leu Glu Ile Ile Ser Leu Glu Ser Ser Thr Ile Asp Ser Tyr
                405                 410                 415

Pro Glu Glu Phe Leu Leu Ala Glu Ile Glu Ser Val Ala Asn Asp Leu
                420                 425                 430

Gln Leu Val Phe Gly Asp Arg Arg Ala Gln Pro Ile Ser Val Pro
                435                 440                 445

His Ile Gln Arg Pro Ser Pro Gln Val Phe Pro Gln Phe Glu Gly Val
    450                 455                 460

Tyr Val Ser Gln Gly Thr Gly Ser Val Pro Pro Thr Ile Pro Thr Asp
465                 470                 475                 480

Pro Asn Lys Thr Pro Ala Ile Ile Leu Glu Ile Trp Gly Ser Gly Glu
                485                 490                 495

Asn Tyr Ser Leu His Pro Ser Leu Leu Lys Arg Arg Lys Arg Lys Arg
                500                 505                 510

Leu Ile Leu
        515

<210> SEQ ID NO 35
<211> LENGTH: 502
<212> TYPE: PRT
<213> ORGANISM: Artificial Sequence
<220> FEATURE:
<223> OTHER INFORMATION: P1PV1_L1

<400> SEQUENCE: 35

Met Ala Val Trp Leu Pro Ala Gln Asn Arg Phe Tyr Leu Pro Pro Gln
1               5                   10                  15

Pro Ser Thr Lys Val Leu Asn Thr Asp Asp Tyr Val Thr Arg Thr Ser
                20                  25                  30

Ile Phe Tyr His Ala Gly Ser Glu Arg Leu Leu Thr Val Gly His Pro
            35                  40                  45

Leu Tyr Asp Ile Tyr Asp Ala Glu Asn Glu His Val Ile Val Pro Lys
        50                  55                  60

Val Ser Ala Asn Gln Tyr Arg Val Phe Arg Ile Arg Leu Pro Asp Pro
65                  70                  75                  80

Asn Asn Phe Ala Phe Gly Asp Lys Ala Ile Phe Asp Pro Glu Lys Glu
                85                  90                  95
```

```
Arg Leu Val Trp Ala Val Arg Gly Leu Glu Ile Gly Arg Gly Gln Pro
                100                 105                 110

Leu Gly Val Cys Val Ser Gly Asn Pro Leu Phe Asp Lys Asn Asn Asp
            115                 120                 125

Val Glu Asn Pro Thr Lys Tyr Phe Ala Asn His Glu Gln Ala Asp Asn
130                 135                 140

Arg Val Asn Val Ala Phe Asp Pro Lys Gln Thr Gln Leu Phe Met Ile
145                 150                 155                 160

Gly Cys Lys Pro Ala Ile Gly Glu His Trp Gly Gln Ala Arg Arg Cys
                165                 170                 175

Val Gly Glu Gly His Thr Pro Gly His Cys Pro Pro Ile Glu Leu Lys
            180                 185                 190

Asn Thr Thr Ile Glu Asp Gly Asp Met Ile Asp Ile Gly Leu Gly Ala
                195                 200                 205

Met Asp Phe Arg Val Leu Gln Gln Asn Lys Ala Gly Val Pro Leu Asp
        210                 215                 220

Ile Ser Asn Ser Glu Cys Lys Tyr Pro Asp Tyr Ile Lys Met Ala Asn
225                 230                 235                 240

Asp Pro Tyr Gly Asp Asn Leu Phe Phe Tyr Val Arg Arg Glu Gln Leu
                245                 250                 255

Tyr Ala Arg His Met Phe Thr Arg Ser Gly Asn Leu Gly Asn Glu Thr
            260                 265                 270

Val Pro Thr Asp Arg Tyr Val Asn Arg Ala Asp Asn Thr Ile Pro Thr
        275                 280                 285

Ser Asn Tyr Phe Ser Thr Pro Ser Gly Ser Leu Val Ser Ser Glu Ala
        290                 295                 300

Gln Leu Phe Asn Arg Pro Tyr Trp Ile Gln Arg Ser Gln Gly Gln Asn
305                 310                 315                 320

Asn Gly Ile Ala Trp Gln Asn Gln Leu Phe Ile Thr Val Val Asp Asn
            325                 330                 335

Thr Arg Gly Thr Ser Leu Asn Ile Ile Met Gly Lys Asp Asp Lys Thr
                340                 345                 350

Ala Thr Gly Asp Phe Asn Pro Ala Asp Tyr Arg Cys Tyr Met Arg His
            355                 360                 365

Val Glu Glu Tyr Glu Ile Ser Leu Ile Leu Gln Leu Cys Lys Val Lys
        370                 375                 380

Leu Thr Pro Glu Asn Leu Ala Phe Ile His Thr Met Asn Pro Asp Ile
385                 390                 395                 400

Ile Glu Asp Trp His Leu Asn Val Asn Pro Pro Ala Gly Ala Ile Asp
                405                 410                 415

Asp Val Tyr Arg Phe Ile Asn Ser Leu Ala Thr Lys Cys Pro Asp Asn
            420                 425                 430

Val Pro Pro Lys Thr Arg Glu Asp Pro Tyr Gly Leu Tyr Arg Phe Trp
        435                 440                 445

Glu Val Asp Leu Lys Asp Lys Met Thr Glu Gln Leu Asp Gln Thr Pro
            450                 455                 460

Leu Gly Arg Lys Phe Leu Phe Gln Thr Gly Val Leu Gln Arg Arg Ala
465                 470                 475                 480

Arg Pro Ala Asn Arg Val Ser Thr Ser Thr Arg Arg Ala Val Lys
                485                 490                 495

Arg Lys Arg Ala Ser Lys
                500
```

<210> SEQ ID NO 36
<211> LENGTH: 515
<212> TYPE: PRT
<213> ORGANISM: Artificial Sequence
<220> FEATURE:
<223> OTHER INFORMATION: P1PV1_L2

<400> SEQUENCE: 36

```
Met Thr Thr Arg Ser Arg Lys Arg Arg Ala Ala Pro Arg Asp Ile Tyr
1               5                   10                  15

Pro Ser Cys Lys Leu Ala Asn Thr Cys Pro Pro Asp Ile Val Asp Ser
            20                  25                  30

Ile Glu Asn Asn Thr Leu Ala Asp Lys Ile Leu Lys Tyr Gly Ser Ala
        35                  40                  45

Gly Val Phe Phe Gly Ser Leu Gly Ile Gly Thr Gly Arg Gly Thr Gly
    50                  55                  60

Gly Ser Thr Gly Tyr Ile Pro Leu Gly Glu Gly Ala Gly Val Arg Leu
65                  70                  75                  80

Asn Thr Arg Val Ser Thr Val Arg Pro Ser Leu Pro Ile Ser Ser Val
                85                  90                  95

His Pro Thr Asp Val Ile Pro Val Asp Ala Val Asp Pro Leu Gly Pro
            100                 105                 110

Ala Ile Val Pro Leu Ser Glu Leu Pro Ser Ile Val Glu Asp Pro Asp
        115                 120                 125

Pro Ile Leu Pro Pro Arg Phe Pro Thr Ala Val Glu Glu Ser Val Ile
    130                 135                 140

Asp Phe Ser Pro Ala Gly Pro Gly Gly Asp Leu Pro Ile Gln Ser Pro
145                 150                 155                 160

Lys Val Thr Thr Thr Asp Thr Ser Ala Leu Ile Glu Val Thr Pro Glu
                165                 170                 175

Thr Arg Pro Pro Arg Ile Ile Ser Arg Ser Gln Tyr Ser Asn Pro Ser
            180                 185                 190

Phe Glu Val His Ile Thr Ser Thr Ser Gly Ser Gly Glu Ser Ser Ala
        195                 200                 205

Val Asp His Val Leu Ile Asp Gly Tyr Ser Gly Gly Glu Val Ile Gly
    210                 215                 220

Glu Glu Ile Pro Leu Ile Asp Leu Gln Ser Thr Arg Ser Ser Asn Thr
225                 230                 235                 240

Phe Ser Thr Thr Glu Val Arg Glu Thr Ser Phe Phe Thr Ser Thr Pro
                245                 250                 255

Arg Gly Glu Leu Pro Ser Ala Arg Pro Arg Thr Leu Tyr Asn Arg Arg
            260                 265                 270

Val Gln Gln Val Gln Val Val Asp Pro Ala Phe Leu Ser Arg Pro Gly
        275                 280                 285

Ala Leu Val Thr Phe Asp Asn Pro Ala Tyr Thr Asp Asp Val Glu Leu
    290                 295                 300

Ile Phe Glu Gln Asp Leu Asp Asp Leu Ala Arg Ala Ala Pro His Glu
305                 310                 315                 320

Asp Phe Arg Asp Ile Val Ser Leu Gly Arg Pro Val Tyr Gly Arg Asn
                325                 330                 335

Pro Gln Gly Gly Val Arg Ile Ser Arg Leu Gly Gln Lys Ala Thr Met
            340                 345                 350

Arg Thr Arg Ser Gly Leu Arg Ile Gly Pro Gln Ser His Phe Phe Tyr
        355                 360                 365
```

```
Asp Ile Ser Glu Ile Ala Glu Pro Glu Leu Glu Leu Val Pro Leu Glu
    370                 375                 380

Pro Pro Phe Val Gly Glu Gln Thr Gly Glu Ser Val Val Gly Ser Ala
385                 390                 395                 400

Leu Gly Glu Phe Glu Thr Ile Ser Leu Ser Asn Glu Pro Ala Ile Tyr
                405                 410                 415

Pro Glu Asp Thr Leu Ile Asp Glu Tyr Glu Val Val Gly Ser Asp Leu
                420                 425                 430

Gln Leu Ile Ile Gly Asp Ser Gly Gly Glu Arg Pro Ile Pro Val Ala
                435                 440                 445

Asp Phe Ala Arg Pro Pro Ala Lys Leu Phe Pro Glu Leu Asp Gly Val
    450                 455                 460

Gln Val Ile Asn Gly Arg Asp Val Ser Arg Ser Ala Thr Val Pro Val
465                 470                 475                 480

Ile Pro Glu Asp Thr Pro Leu Ile Ile Glu Val Leu Asp Gly Ser
                485                 490                 495

Gly Asp Tyr Phe Leu His Pro Ser Leu Phe Arg Lys Arg Lys Arg
                500                 505                 510

Pro Phe Phe
    515

<210> SEQ ID NO 37
<211> LENGTH: 501
<212> TYPE: PRT
<213> ORGANISM: Artificial Sequence
<220> FEATURE:
<223> OTHER INFORMATION: PtPV1_L1

<400> SEQUENCE: 37

Met Trp Arg Pro Ser Asp Asn Lys Leu Tyr Val Pro Pro Ala Pro
1               5                   10                  15

Val Ser Lys Val Leu Thr Thr Asp Ala Tyr Val Thr Arg Thr Lys Ile
                20                  25                  30

Phe Tyr His Ala Ser Ser Arg Leu Leu Ala Val Gly Asn Pro Tyr
                35                  40                  45

Phe Pro Ile Arg Lys Ala Asn Lys Thr Ile Val Pro Lys Val Ser Gly
            50                  55                  60

Phe Gln Phe Arg Val Phe Lys Ile Val Leu Pro Asp Pro Asn Lys Phe
65                  70                  75                  80

Ala Leu Pro Asp Thr Ser Ile Phe Asp Ser Thr Ser Gln Arg Leu Val
                85                  90                  95

Trp Ala Cys Ile Gly Leu Glu Val Gly Arg Gly Gln Pro Leu Gly Val
                100                 105                 110

Gly Tyr Cys Gly His Pro Cys Leu Asn Lys Phe Asp Asp Val Glu Asn
            115                 120                 125

Ser Ala Ser Tyr Ala Val Asn Pro Gly Gln Asp Asn Arg Val Asn Val
        130                 135                 140

Ala Met Asp Tyr Lys Gln Thr Gln Leu Cys Leu Val Gly Cys Ala Pro
145                 150                 155                 160

Pro Leu Gly Glu His Trp Gly Lys Gly Lys Gln Cys Ser Gly Val Ser
                165                 170                 175

Val Gln Asp Gly Asp Cys Pro Pro Leu Glu Leu Val Thr Ser Val Ile
            180                 185                 190

Gln Asp Gly Asp Met Val Asp Thr Gly Phe Gly Ala Met Asp Phe Ala
        195                 200                 205
```

-continued

Glu Leu Gln Ser Asn Lys Ser Asp Val Pro Leu Asp Ile Cys Thr Ser
210                 215                 220

Thr Cys Lys Tyr Pro Asp Tyr Leu Gln Met Ala Ala Asp Pro Tyr Gly
225                 230                 235                 240

Asp Arg Leu Phe Phe Tyr Leu Arg Lys Glu Gln Met Phe Ala Arg His
            245                 250                 255

Phe Phe Asn Arg Ala Gly Thr Val Gly Glu Gln Ile Pro Asp Glu Leu
        260                 265                 270

Phe Val Lys Gly Thr Thr Ser Arg Ala Thr Val Ser Ser Asn Ile Tyr
    275                 280                 285

Phe Asn Thr Pro Ser Gly Ser Leu Val Ser Ser Glu Ala Gln Leu Phe
290                 295                 300

Asn Lys Pro Tyr Trp Leu His Lys Ala Gln Gly His Asn Asn Gly Ile
305                 310                 315                 320

Cys Trp Gly Asn Thr Leu Phe Val Thr Val Val Asp Thr Thr Arg Ser
                325                 330                 335

Thr Asn Met Thr Val Cys Ala Ser Thr Thr Ser Ser Pro Ser Ala Thr
            340                 345                 350

Tyr Thr Ala Ser Glu Tyr Lys Gln Tyr Met Arg His Val Glu Glu Phe
        355                 360                 365

Asp Leu Gln Phe Ile Phe Gln Leu Cys Thr Ile Lys Leu Thr Ala Glu
    370                 375                 380

Leu Met Ala Tyr Ile His Thr Met Asn Pro Thr Val Leu Glu Glu Trp
385                 390                 395                 400

Asn Phe Gly Leu Ser Pro Pro Asn Gly Thr Leu Glu Asp Thr Tyr
                405                 410                 415

Arg Tyr Val Gln Ser Gln Ala Ile Thr Cys Gln Lys Pro Thr Pro Asp
            420                 425                 430

Lys Glu Lys Gln Asp Pro Tyr Ala Gly Leu Ser Phe Trp Glu Val Asn
        435                 440                 445

Leu Lys Glu Lys Phe Ser Ser Glu Leu Gln Tyr Pro Leu Gly Arg
    450                 455                 460

Lys Phe Leu Leu Gln Thr Gly Val Gln Ser Thr Ser Leu Ala Arg Ala
465                 470                 475                 480

Gly Thr Lys Arg Ala Ala Ser Thr Ser Thr Ala Thr Pro Thr Arg Lys
                485                 490                 495

Lys Val Lys Arg Lys
            500

<210> SEQ ID NO 38
<211> LENGTH: 462
<212> TYPE: PRT
<213> ORGANISM: Artificial Sequence
<220> FEATURE:
<223> OTHER INFORMATION: PtPV1_L2

<400> SEQUENCE: 38

Met Ala His Ser Arg Pro Arg Arg Arg Lys Arg Ala Ser Ala Thr Gln
1               5                   10                  15

Leu Tyr Gln Thr Cys Lys Ala Ser Gly Thr Cys Pro Asp Ile Ile Pro
            20                  25                  30

Lys Val Glu Gln Asn Thr Leu Ala Asp Lys Ile Leu Lys Trp Gly Ser
        35                  40                  45

Leu Gly Val Phe Phe Gly Gly Leu Gly Ile Gly Thr Gly Ser Gly Thr
    50                  55                  60

Gly Gly Arg Thr Gly Tyr Val Pro Leu Glu Ser Ala Pro Arg Pro Ala
 65                  70                  75                  80

Ile Pro Phe Gly Pro Thr Ala Arg Pro Ile Val Val Asp Thr Val
             85                  90                  95

Gly Pro Thr Asp Ser Ser Ile Val Ser Leu Val Glu Asp Ser Ala Ile
            100                 105                 110

Ile Asn Ser Gly Ala Ser Asp Leu Val Pro Ser Ile His Gly Gly Phe
            115                 120                 125

Glu Ile Ser Thr Ser Glu Ser Thr Thr Pro Ala Ile Leu Asp Val Ser
130                 135                 140

Ile Thr Thr His Asn Thr Thr Ser Thr Ser Ile Phe Arg Asn Pro Ala
145                 150                 155                 160

Phe Ala Glu Pro Ser Ile Val Gln Ser Gln Pro Ser Val Glu Ala Gly
                165                 170                 175

Gly His Leu Leu Thr Ser Thr Phe Thr Ser Thr Ile Ser Pro His Ser
            180                 185                 190

Val Glu Glu Ile Pro Leu Asp Thr Phe Ile Val Ser Ser Asn Ser
            195                 200                 205

Asn Pro Ala Ser Ser Thr Pro Val Pro Thr Thr Val Ala Arg Pro Arg
210                 215                 220

Leu Gly Leu Tyr Ser Lys Ala Leu His Gln Val Gln Val Thr Asp Pro
225                 230                 235                 240

Ala Phe Leu Ser Ser Pro Gln Arg Leu Ile Thr Phe Asp Asn Pro Val
                245                 250                 255

Tyr Glu Gly Glu Asp Ile Ser Leu His Phe Glu His Asn Ser Ile His
            260                 265                 270

Glu Pro Pro Asn Glu Ala Phe Met Asp Ile Ile Arg Leu His Arg Pro
            275                 280                 285

Ala Ile Thr Ser Arg Arg Gly Val Val Arg Phe Ser Arg Ile Gly Gln
            290                 295                 300

Arg Gly Ser Met Tyr Thr Arg Ser Gly Lys His Ile Gly Gly Arg Val
305                 310                 315                 320

His Phe Phe Thr Asp Ile Ser Pro Ile Ser Ala Asp Ala Gln Asp Ile
                325                 330                 335

Glu Leu Gln Pro Leu Val Ala Ala Gln Asp Asp Ser Asp Leu Phe
            340                 345                 350

Asp Ile Tyr Val Asp Pro Asp Thr Pro Val Ala Val Asp Asn Ile
            355                 360                 365

Pro Ser Ala Asn Ser Thr Leu Phe Ile Lys Ser Ser Ile Phe Asp Thr
            370                 375                 380

Ser Trp Gly Asn Thr Thr Ile Pro Leu Ser Leu Pro Asn Asn Ile Phe
385                 390                 395                 400

Val Gln Pro Gly Pro Asp Ile Leu Phe Pro Thr Thr Pro Ala Val Pro
                405                 410                 415

Pro Tyr Gly Pro Val Ile Ser Pro Leu Pro Val Gly Val Phe Ile
            420                 425                 430

Ser Gly Ser Glu Phe Tyr Leu His Pro Ser Leu Tyr Phe Ala Arg Lys
            435                 440                 445

Arg Arg Lys Arg Val Ser Leu Phe Phe Ser Asp Val Ala Ala
450                 455                 460

<210> SEQ ID NO 39
<211> LENGTH: 553
<212> TYPE: PRT

<213> ORGANISM: Artificial Sequence
<220> FEATURE:
<223> OTHER INFORMATION: RaPV_L1

<400> SEQUENCE: 39

```
Met Thr Gln Leu His Met Thr Thr Gly Leu Ile Tyr Thr Cys Thr Cys
1               5                   10                  15

Leu Gly Lys Ser Ala Asn Gly Val Pro Ser Ala Leu Leu Gln Met Ala
            20                  25                  30

Leu Trp Ile Pro Ser Pro Gln Ala Val Tyr Val Ala Pro Ala Pro Val
        35                  40                  45

Thr Thr Ile Pro Ser Thr Glu Asp Phe Ile Thr Arg Thr Pro Tyr Phe
    50                  55                  60

Tyr His Ala Asn Ser Asp Arg Leu Leu Thr Val Gly Asn Pro Phe Tyr
65                  70                  75                  80

Ala Ile Lys Asp Pro Gly Thr Gln Lys Ile Leu Val Pro Lys Val Ser
                85                  90                  95

Gly Asn Gln Tyr Arg Val Phe Arg Ile Arg Phe Pro Asp Pro Asn Lys
            100                 105                 110

Phe Ala Leu Pro Asp Pro Asn Val Phe Asn Pro Asp Thr Glu Arg Leu
        115                 120                 125

Val Trp Gly Leu Arg Gly Ile Glu Val Gly Arg Gly Gly Pro Leu Gly
    130                 135                 140

Met Glu Val Thr Gly Asn Leu Gly Phe Gly Arg Asn Ala Asp Val Glu
145                 150                 155                 160

Asn Pro Asn Gln Ala Glu Arg Glu His Gly Ala Val Gly Thr Lys Arg
                165                 170                 175

Phe Asn Val Gly Met Glu Pro Lys Gln Asn Gln Leu Leu Ile Val Gly
            180                 185                 190

Cys Ser Pro Ala Trp Gly Glu Phe Trp Asp Ser Thr Pro Ala Cys Thr
        195                 200                 205

Glu Gly Asp Thr Pro Val Asp Pro Gly Ala Gly Asp Cys Pro Ala Leu
    210                 215                 220

Glu Leu Lys Ser Thr Arg Leu Gln Asp Gly Thr Met Thr Asp Ile Gly
225                 230                 235                 240

Phe Gly His Met Asn Phe Lys Ser Leu Gln Asp Asp Lys Ser Gly Val
                245                 250                 255

Pro Leu Glu Ile Val Asn Ser Val Cys Val Tyr Pro Asp Phe Tyr Lys
            260                 265                 270

Met Ser Lys Asp Pro Tyr Gly Asn Ser Cys Phe Phe Ser Val Arg Lys
        275                 280                 285

Glu Gln Met Tyr Ile Arg His Tyr Phe Ser Arg Val Gly Ala Tyr Gly
    290                 295                 300

Asp Thr Val Pro Thr Asp Met Tyr Leu Lys Asp Lys Thr Asn Gly Gly
305                 310                 315                 320

Ala Asn Trp Thr Gly Pro Val Tyr Met Gly Thr Pro Ser Gly Ser Ile
                325                 330                 335

Val Ser Thr Glu Gly Gln Val Leu Asn Arg Pro Tyr Trp Leu Leu Lys
            340                 345                 350

Ala Gln Gly Arg Asn Asn Gly Met Leu Trp Gly Asn Gln Cys Phe Val
        355                 360                 365

Thr Val Val Asp Asn Thr Arg Ser Leu Asn Phe Leu Ile Asn Val Lys
    370                 375                 380
```

```
Asn Asp Ala Gly Thr Ser Phe Gln Ala Asp Glu Phe Ala Asn Tyr Leu
385                 390                 395                 400

Arg His Thr Glu Glu Tyr Glu Ile Ala Cys Ile Val Gln Leu Cys Lys
            405                 410                 415

Val Arg Leu Asp Pro Glu Thr Leu Ser Ile Leu Asn Thr Met Asp Pro
        420                 425                 430

Glu Ile Leu Glu Glu Trp Gln Ile Gly Val Asn Pro Pro Val Ser Ser
    435                 440                 445

Gln Val Asn Asp Arg Tyr Arg Phe Val His Ser Leu Ala Thr His Cys
450                 455                 460

Pro Asp Lys Glu Lys Ala Lys Glu Lys Glu Asp Pro Tyr Ala Gly Leu
465                 470                 475                 480

Ala Phe Trp Asn Leu Asp Phe Thr Glu Ser Leu Ser Pro Asp Leu Asp
                485                 490                 495

Gln Phe Pro Leu Gly Arg Arg Phe Leu Thr Gln Ala Gly Arg Ala Gly
            500                 505                 510

Arg Thr Ser Gly Thr Arg Ser Thr Ala Arg Thr Gly Arg Thr Gly Thr
        515                 520                 525

Val Val Lys Arg Ser Ile Val Ser Thr Thr Val Ala Gly Lys Pro Arg
    530                 535                 540

Ser Val Pro Ala Lys Arg Arg Arg
545                 550

<210> SEQ ID NO 40
<211> LENGTH: 556
<212> TYPE: PRT
<213> ORGANISM: Artificial Sequence
<220> FEATURE:
<223> OTHER INFORMATION: RaPV1_L2

<400> SEQUENCE: 40

Met Ala Pro Arg Lys Arg Ala Thr Arg Val Pro Arg Asp Ser Ala
1               5                   10                  15

Thr Asn Leu Tyr Arg Gln Pro Gly Cys Arg Val Asp Gly Asn Cys Pro
                20                  25                  30

Trp Gly Val Lys Glu Gln Ile Glu Asn Lys Thr Pro Ala Asp Arg Ile
            35                  40                  45

Leu Gln Tyr Gly Ser Ala Val Ile Asn Leu Gly Leu Gly Ile Gly
        50                  55                  60

Thr Gly Ala Gly Ser Gly Gly Arg Gly Gly Tyr Ile Pro Met Gly Ala
65                  70                  75                  80

Asp Arg Gly Ile Gly Val Gly Ala Trp Pro Arg Pro Ala Tyr Pro Ala
                85                  90                  95

Arg Pro Val Val Pro Ala Ile Glu Thr Val Gly Pro Thr Ile Ser Ile
            100                 105                 110

Pro Glu Val Val Ala Thr Asp Val Ile Glu Met Glu Pro Ile Val Thr
        115                 120                 125

Ala Val Asp Pro Ser Val Ile Asp Thr His Pro Pro Ile Asp Pro Thr
130                 135                 140

Asp Pro Ala Ile Val Glu Asp Phe Gly Ser Tyr Pro Arg Pro Ala
145                 150                 155                 160

Ile Ile Asp Glu Ser Val Pro Thr Gln Gly Gly Asn Arg Ile Gln Val
                165                 170                 175

Val Ala Glu Val His His Pro Ala Asp Leu Phe Pro Ser Thr Thr Ile
            180                 185                 190
```

```
Ser Ser Gly Gly Ser Thr Thr Ser Ala Val Leu Glu Val Gly Glu Gln
        195                 200                 205
Ile Pro Leu Met Pro Arg Ser Asn Pro Pro His Ile His Glu Pro Ser
    210                 215                 220
Leu Leu Thr Thr Thr Thr Ser Phe Gly Thr Asn Ala Asp Val Val Gly
225                 230                 235                 240
Ser Arg Ala Ser Ile Ile Asp Phe Asp Ala Val Asp Glu Ala Val Gly
                245                 250                 255
Asp Asp Ile Pro Leu Leu Asp Arg Thr Tyr Asp Arg Asn Ala Asn Leu
            260                 265                 270
Glu Phe Arg Thr Ser Thr Pro Gln Ser Gly Arg Arg Pro Asn Pro Val
        275                 280                 285
Lys Ala Leu Lys Ser Leu Tyr Asn Lys Tyr Val Arg Gln Val Pro Val
        290                 295                 300
Glu Asp Pro Leu Phe Met Glu Ala Pro Gly His Leu Ile Glu Phe Gly
305                 310                 315                 320
Asn Pro Val Phe Gln Pro Glu Glu Ser Leu Glu Tyr Pro Leu Gln Asp
                325                 330                 335
Asn Pro Leu Ala Ser Pro Asp Glu Arg Leu Gln Gly Thr His Arg Leu
            340                 345                 350
His Arg Pro Ile Leu Ser Glu Val Pro Gly Gly Arg Gly Ile Arg Leu
        355                 360                 365
Ser Arg Leu Gly Ala Ile Gly Ala Met Arg Met Arg Ser Gly Leu Thr
    370                 375                 380
Val Gly Pro Arg Val His Val Tyr His Asp Ile Ser Ser Ile Glu Glu
385                 390                 395                 400
Ala Ile Glu Leu Gln Pro Leu Gly Val Glu Pro His Ser Val Thr Gly
                405                 410                 415
Glu Ala Val Met Gln Asp Thr Ser Val Asp Ala Leu Thr Glu Glu Asp
            420                 425                 430
Ile Thr Glu Gln Gly Phe Glu Asp Val Pro Leu Leu Ser Pro His Ala
        435                 440                 445
Gly Gln Gln Val Arg Leu Gln Val Gly Pro Gly Gly Arg Asn Asn Arg
    450                 455                 460
Asn Val Val Ser Leu Glu Ile Pro Thr Thr Asn Arg Ala Asp Thr Phe
465                 470                 475                 480
Gly Ile Asn Ile Gly Glu Ala Ser Asp Ile Tyr Val His Tyr Ala Asp
                485                 490                 495
Glu Lys His Thr Ile Pro Gly Phe Val Pro Gly Ile Pro Leu Gly Pro
            500                 505                 510
Ala Val Pro Pro Val Ile Val Glu Asp Thr Ala Ala Tyr Asp Tyr
        515                 520                 525
Trp Phe Asp Leu Tyr Leu His Leu Pro Arg Lys Lys Arg Lys Trp Cys
    530                 535                 540
Ser Phe Cys Ser Leu Thr Asp Gly Ile Val Asp Thr
545                 550                 555
```

NON-HUMAN PAPILLOMAVIRUSES FOR GENE DELIVERY IN VITRO AND IN VIVO

PRIORITY AND CROSS REFERENCE TO RELATED APPLICATIONS

This application is the U.S. National Phase Application under 35 U.S.C. § 371 of International Application No. PCT/EP2018/081102, filed Nov. 13, 2018, designating the U.S. and published in English as WO 2019/096796 A1 on May 23, 2019, which claims the benefit of German Application No. DE 10 2017 220 276.9, filed Nov. 14, 2017. Any and all applications for which a foreign or a domestic priority is claimed is/are identified in the Application Data Sheet filed herewith and is/are hereby incorporated by reference in their entireties under 37 C.F.R. § 1.57.

SEQUENCE LISTING IN ELECTRONIC FORMAT

The present application is being filed along with an Electronic Sequence Listing as an ASCII text file via EFS-Web. The Electronic Sequence Listing is provided as a file entitled HRZG001010APCSEQLIST.txt, created and last saved on May 13, 2020, which is 126,406 bytes in size. The information in the Electronic Sequence Listing is incorporated herein by reference in its entirety.

FIELD

The present invention relates to non-human papillomaviruses for in vitro and in vivo gene delivery.

SUMMARY

The present invention relates to a non-human papilloma pseudovirus or virus like particle comprising at least one papilloma capsid protein codon-optimized for expression in eukaryotic cells or cell lines, and to a pharmaceutical composition comprising the non-human papilloma pseudovirus or virus like particle of the invention, and an agent selected from the group consisting of: a diagnostic agent, an imaging agent, and a therapeutic agent. Moreover, the invention pertains to a non-human papilloma pseudovirus or virus like particle of the invention for use as a medicament. Further encompassed by the invention is a method for producing a non-human papilloma pseudovirus or virus like particle, comprising the steps of: a) codon-optimizing of capsid proteins of non-human papillomaviruses for expression in eukaryotic cells; b) synthesizing of the sequences and cloning of the synthesized sequences into expression vectors; and c) producing non-human papilloma pseudovirus or virus like particles. Finally, the invention relates to the use of ι-carrageenan as transduction enhancer for non-human papilloma pseudovirus or virus like particles in vitro.

DETAILED DESCRIPTION

Figure 1:
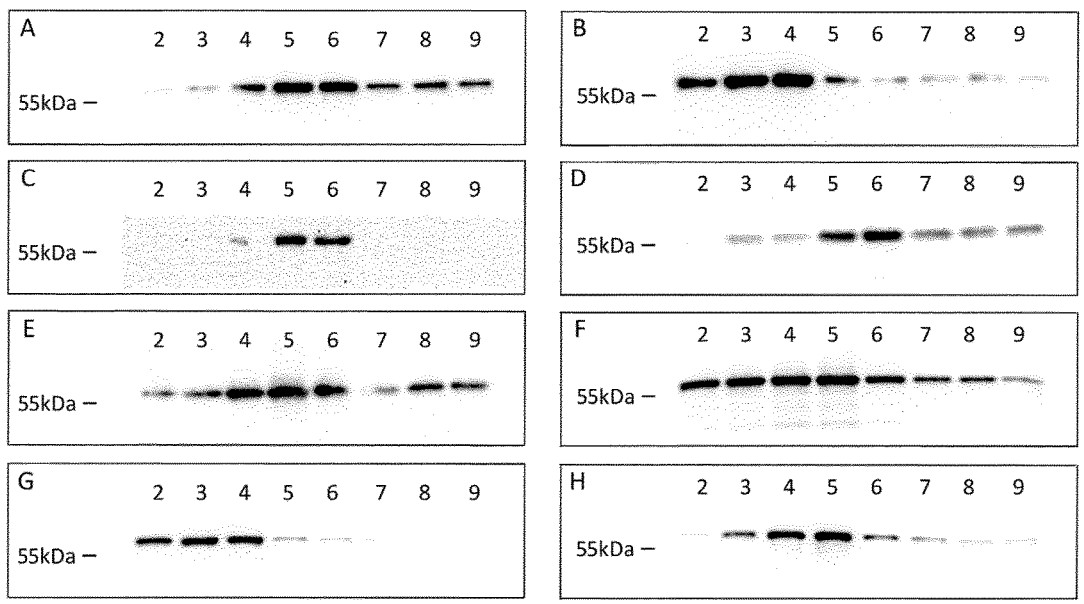
FIG. 1 shows Western Blots of fractions after purification by ultracentrifugation. All produced non-human papilloma PsVs were purified by density gradient ultracentrifugation. Subsequently, the collected fractions were separated by SDS-PAGE, blotted onto a nitrocellulose membrane and probed for L1. (A) MfPV6, (B) CcrPV1, (C) CcPV1, (D) CgPV1, (E) MmPV1, (F) MfPV11, (G) PcPV1, (H) PlPV1.

The use of nucleic acids as genetic vaccines has several advantages, most importantly the rapid production, simple adaptation and high stability at ambient temperature. Additionally, the vaccinee's cells themselves express the encoded antigens, which guarantees correct post-translational modifications and folding of the protein. Immunization with a DNA vaccine activates both the humoral and cellular immune response, making genetic vaccines a powerful platform. While intramuscular injection of naked DNA leads to a reasonable cellular uptake and subsequent expression in rodents, larger animals, especially non-human primates, require additional stimuli to enhance the uptake of the plasmid DNA.

One of the most powerful methods to enhance the uptake of DNA is the use of electroporation. Although quite effective, electroporation is an invasive and painful procedure, requiring local anesthesia and the presence of special equipment.

Other delivery methods include physical devices such as pressure injector, gene gun, and chemical formulations like block copolymers, cationic liposome and polyethyleneimine.

Furthermore, the application of bacteria and viruses as gene carriers has been explored, human papillomaviruses being one of them. Gene delivery using papillomaviruses does face the same issues as other more commonly used viruses, which is the problem of vector immunity. Human papillomaviruses (HPV), especially type 16, work quite well as gene delivery vehicles, however, more and more virus like particles (VLPs) of different papilloma types are being added to vaccines against HPV. Merck's "Gardasil 9", approved by the FDA in December 2014, includes VLPs of HPV types 6, 11, 16, 18, 31, 33, 45, 52, and 58. It would consequently not be possible to apply these papillomavirus types as gene carriers in Gardasil 9 vaccinated individuals. In addition to vaccine-induced immunity against HPV, natural infection occurs quite frequently, making it difficult to reliably apply HPV for the delivery of genetic vaccines in the general population.

In view of the above, an ongoing demand exists for the development of efficient and safe means and methods for the transfer of nucleic acids by papillomaviruses.

The technical problem underlying the present invention can be seen as the provision of means and methods for complying with the aforementioned needs. The technical problem is solved by the embodiments characterized in the claims and herein below.

The present invention pertains to a non-human papilloma pseudovirus or virus-like particle comprising at least one papilloma capsid protein codon-optimized for expression in eukaryotic cells or cell lines.

The inventors explored the in vitro production of non-human papilloma virus-like particles (VLPs) and pseudovirions (PsVs) and their ability to deliver reporter plasmids in vitro and in vivo, as shown in the following Examples. Published sequences for capsid proteins L1 and L2 of ten non-human papilloma viruses indicated in the following Table 3 were codon-optimized for expression in human cell lines, synthesized and cloned into expression vectors. VLPs and PsVs were produced following the protocol by Buck et. al (C. Buck, D. Pastrana, D. Lowy, J. Schiller, in Human Papillomaviruses, C. Davy, J. Doorbar, Eds. (Humana Press, 2006), vol. 119, pp. 445-462), with slight modifications. VLPs and PsVs from *Puma concolor* papillomavirus 1 (PcPV1) and *Macaca fascicularis* papillomavirus type 11, isolate Mac1637 (MfPV11), could be identified as efficient gene vectors in vitro. Further, PsVs from *Puma concolor* papillomavirus 1 (PcPV1) could be found as efficient delivery vector in vivo. These findings demonstrate that it is worth exploring the wide range of non-human papilloma viruses for gene delivery, gene therapy, therapeutic, diagnostic and vaccination approaches.

Several characteristics of non-human papilloma viruses make them interesting candidates as DNA delivery vectors, such as their stability due to being non-enveloped, their ability to package foreign DNA without the need of a specific packaging sequence and—depending on the type of papillomavirus—their capability to infect mucosal tissue. Additionally, the viral capsid might provide some adjuvant effect by stimulating the innate immune system. Papillomaviruses as non-enveloped viruses are also more stable than enveloped viruses.

In 2013,260 different papillomavirus types were identified, among those 148 human (A. Rector and M. van Ranst, Animal papillomaviruses, Virology. 445, 213-223 (2013), doi:10.1016/j.virol.2013.05.007).

To date, 112 distinct non-human papillomavirus types have been genomically characterized and are available on GenBank and listed in the following Table 1 which corresponds to Table 1 of the mentioned publication by A. Rector and M. van Ranst (2013). The 112 distinct non-human papillomavirus types are distributed over 32 different genera, leaving only the genus Gammapapillomavirus, Mupapillomavirus and Nupapillomavirus to contain exclusively HPV types (see FIG. 1 of the publication by A. Rector and M. van Ranst (2013)). Within some well-studied vertebrate species, such as cynomolgus macaques, domestic cows and dogs, a multitude of different papillomavirus types have already been discovered (MfPV1 to MfPV11, BPV1 to BPV13 and CPV1 to CPV15, respectively; see Table 1 of the publication by A. Rector and M. van Ranst (2013)), indicating that also non-human vertebrate species could carry their own sets of species-specific papillomavirus types.

The term "non-human papilloma virus" as used herein refers to one of the 112 distinct non-human papillomavirus types indicated in the following Tables 1, preferably to the non-human papillomaviruses of Table 2, more preferably to the non-human papillomaviruses of Table 3.

The term "virus-like particle" (VLP) as referred to herein means a self-assembling supra-molecular structure formed by (a) viral structural protein(s). Many VLPs share the physicochemical characteristics of their parental viruses, they do not, however, carry any genetic information, including genetic information for replication. These properties can be harnessed for targeted delivery of genetic information or active drug substances to specified cell types as well as for delivery of an antigen of interest to B cells for induction of effective antibody responses. For example, VLPs can be produced experimentally by expression of capsid proteins of a virus, as detailed elsewhere herein. VLPs can be used, e.g., for gene delivery in vitro or in vivo, or for the development of pharmaceutical compositions, e.g., for diagnosis, imaging, therapy or vaccination, as set forth herein below.

The term "non-human papilloma pseudovirion or pseudovirus (PsV)" or "non-human papilloma pseudovirion or pseudovirus (PsV) particle" as used herein denotes a virus-like particle, which additionally contains plasmid-DNA packaged inside the capsid. This plasmid-DNA may code for any protein of interest, which is meant to be expressed by the target cell upon delivery by the PsV, e.g., an antigen for vaccination.

A "peptide or protein" as referred to herein relates to a molecule consisting of amino-acid residues joined by peptide bonds. Peptides, consisting of several, typically, at least 20, at least 30, at least 40, at least 50 or at least 60 amino acids that are covalently linked to each other by peptide bonds, are commonly referred to as polypeptides. Molecules consisting less than 20 amino acids covalently linked by peptide bonds are typically considered to be peptides.

The term "capsid protein" as used herein refers to the capsid protein L1 and/or L2. The papillomavirus genome is divided into an early region (E), encoding six open reading frames (ORFs) E1, E2, E4, E5, E6, and E7, that are expressed immediately after initial infection of a host cell, and a late region (L) encoding a major capsid protein L1 and a minor capsid protein L2. All viral ORFs are encoded on one DNA strand. Expression of the capsid protein L1 and/or L2 in appropriate cells allow for the formation of virus-like particles (VLPs) or non-human papilloma pseudovirions (PsVs) as defined herein. The capsid proteins L1 and/or L2 are codon-optimized for expression in eukaryotic cells or cell lines, such as human cells or cell lines, as explained elsewhere herein. The wild-type sequences for many L1 and L2 capsid proteins of non-human papilloma viruses are described in the art and available, e.g., in GenBank. For instance, Tables 1, 2 and 3 of this application provide the corresponding accession numbers of genomes of preferred non-human papilloma viruses, including the sequences coding for L1 and L2 capsid proteins. In the following Examples, capsid proteins L1 and L2 of ten non-human papilloma viruses indicated in Table 3 were codon-optimized for expression in human cell lines, synthesized and cloned into expression vectors.

The term "codon-optimized papilloma capsid protein" as used herein denotes a non-human papilloma capsid gene L1 or L2 which has been converted to a sequence having an identical translated sequence but with alternative codon usage, for expression in eukaryotic cells or cell lines, e.g., human cells or cell lines, as defined by Lathe, 1985, J. Mol. Biol. 183: p. 1-12.

Gene or codon-optimization takes advantage of the degeneracy of the genetic code. Because of degeneracy, one protein can be encoded by many alternative nucleic acid sequences. Codon preference (codon usage bias) differs in each organism, and it can create challenges for expressing recombinant proteins in heterologous expression systems, resulting in low and unreliable expression.

The methodology of codon-optimization for expression in human cells may be summarized as follows:
 (i) Identify placement of codons for proper open reading frame.
 (ii) Compare wild type codon for observed frequency of use by human genes.
 (iii) If codon is not the most commonly employed, replace it with an optimal codon for high expression in human cells.
 (iv) Repeat this procedure until the entire gene segment has been replaced.
 (v) Inspect new gene sequence for undesired sequences generated by these codon replacements (e.g. "ATTTA" sequences, inadvertent creation of intron splice recognition sites, unwanted restriction sites, etc.) and substitute codons that eliminate these sequences.
 (vi) Assemble synthetic gene segments and test for improved expression.

Methods and tools for codon-optimization of sequences are well described in the art; see, e.g., U.S. Pat. No. 8,326,547; Ternette N., et al., Virology Journal 2007, Expression of RNA virus proteins by RNA polymerase II dependent expression plasmids is hindered at multiple steps. https://doi.org/10.1186/1743-422X-4-51; Haas J, Park E C, Seed B: Codon usage limitation in the expression of HIV-1 envelope glycoprotein. Curr Biol 1996, 6: 315-324. 10.1016/50960-9822(02)00482-7; Wagner R, Graf M, Bieler K, Wolf H, Grunwald T, Foley P, Uberla K: Rev-independent expression of synthetic gag-pol genes of human immunodeficiency virus type 1 and simian immunodeficiency virus: implications for the safety of lentiviral vectors. Hum Gene Ther 2000, 11: 2403-2413. 10.1089/104303400750038507; or Morton C J, Cameron R, Lawrence L J, Lin B, Lowe M, Luttick A, Mason A, Kimm-Breschkin J, Parker M W, Ryan J, Smout M, Sullivan J, Tucker S P, Young P R: Structural characterization of respiratory syncytial virus fusion inhibitor escape mutants: homology model of the F protein and a syncytium formation assay. Virology 2003, 311: 275-288. 10.1016/S0042-6822 (03)00115-6.

As appreciated by those skilled in the art, the use of alternative codons encoding the same protein sequence removes the constraints on expression of non-human papilloma virus capsid proteins L1 and/or L2 by eukaryotic cells or cell lines, such as human cells or cell lines.

The term "vector" as used herein encompasses preferably phage, plasmid, viral vectors such as non-human papilloma viral vectors or retroviral vectors as well as artificial chromosomes, such as bacterial or yeast artificial chromosomes. Moreover, the term also relates to targeting constructs which allow for random or site-directed integration of the targeting construct into genomic DNA. Such target constructs, in an aspect, comprise a DNA of interest of sufficient length for either homologous or heterologous recombination as known in the art. The vector, in an aspect, further comprises selectable markers for propagation and/or selection in a host cell. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerens. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells.

The term "eukaryotic cell or cell line" as referred to herein means a eukaryotic cell or cell from a eukaryotic cell line susceptible to transduction or infection by non-human papilloma viruses, such as yeast (e.g., *S. cerevisiae*), insect cells (e.g., Sf9 or Sf21), mammalian cells (e.g., P19, NIH 3T3 or CHO cells), or human cells (e.g. HEK293, HT-1080 or HeLa cells). Eukaryotic cells or cell lines and conditions for their cultivation are well described in the art.

The term "human cell or cell line" as referred to herein means a human cell or cell from a human cell line susceptible to transduction or infection by non-human papilloma viruses. As known in the art, transduction is the process by which foreign DNA is introduced into a cell by a virus or viral vector. The term "cell" encompasses cells from human, from a variety of cell types such as, e.g., mucosal or cutaneous cells, and can be isolated from or part of a heterogeneous cell population, human tissue or organism. It is to be understood that human embryonic cells are excluded from the scope of the invention. Aspects of the present disclosure comprise, in part, a cell from an established cell line. As used herein, the term "established cell line" is synonymous with "immortal cell line," or "transformed cell line" and refers to a cell culture of cells selected for indefinite propagation from a cell population derived from a human organism, tissue, or organ source. By definition, an established cell line excludes a cell culture of primary cells. As used herein, the term "primary cells" are cells harvested directly from fresh human tissues or organs and do not have the potential to propagate indefinitely. An established cell line can comprise a heterogeneous population of cells or a uniform population of cells. An established cell line derived from a single cell is referred to as a clonal cell line. The papilloma capsid protein referred to herein is codon-optimized for expression in eukaryotic cells or cell lines, for instance, yeast (e.g., *S. cerevisiae*), insect cells (e.g., Sf9 or Sf21), mammalian cells (e.g., P19, NIH 3T3 or CHO cells), or human cells (e.g. human kidney epithelial cells, HEK293, HT-1080 or HeLa cells). The human cell line can be, for example, HEK293T or HEK293FT.

The terms "comprising", "comprises" and "comprised of" as used herein are synonymous with "including", "includes" or "containing", "contains", and are inclusive or open-ended and do not exclude additional, non-recited members, elements or method steps. Evidently, the term "comprising" encompasses the term "consisting of". More specifically, the term "comprise" as used herein means that the claim encompasses all the listed elements or method steps, but may also include additional, unnamed elements or method steps. For example, a method comprising steps a), b) and c) encompasses, in its narrowest sense, a method which consists of steps a), b) and c). The phrase "consisting of" means that the composition (or device, or method) has the recited elements (or steps) and no more. In contrast, the term "comprises" can encompass also a method including further steps, e.g., steps d) and e), in addition to steps a), b) and c).

The term "in vitro" as used herein denotes outside, or external to, the animal or human body. The term "in vitro" as used herein should be understood to include "ex vivo". The term "ex vivo" typically refers to tissues or cells removed from an animal or human body and maintained or propagated outside the body, e.g., in a culture vessel. The term "in vivo" as used herein denotes inside, or internal to, the animal or human body. Preferably, the methods of the invention are in vitro methods.

As used herein, the term "about" when qualifying a value of a stated item, number, percentage, or term refers to a range of plus or minus 10 percent, 9 percent, 8 percent, 7 percent, 6 percent, percent, 4 percent, 3 percent, 2 percent or 1 percent of the value of the stated item, number, percentage, or term. Preferred is a range of plus or minus 10 percent.

Whether a value or number or amount or portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.001. Preferably, the probability envisaged by the present invention allows that the assessment will be correct for at least 60%, at least 70%, at least 80%, at least 85%, at least 90%, at least 95% or at least 97% of the subjects of a given cohort.

Non-human papillomavirus capsid structures, VLPs and PsVs of the invention can be produced by methods described in the art (see, e.g., C. Cerqueira et al., Efficient Production of Papillomavirus Gene Delivery Vectors in Defined In Vitro Reactions, Molecular therapy. Methods & clinical development. 5, 165-179 (2017), doi:10.1016/j.omtm.2017.04.005; Q. Zhao et al., Disassembly and reassembly of human papillomavirus virus-like particles produces more virion-like antibody reactivity, Virology journal. 9, 52 (2012), doi:10.1186/1743-422X-9-52; Buck, C., et al (2006a). Generation of HPV Pseudovirions Using Transfection and Their Use in Neutralization Assays. In Human Papillomaviruses, C. Davy and J. Doorbar, eds. (Humana Press), pp. 445-462, doi: 10.1385/1-59259-982-6:445; WO 2011/039646; U.S. Pat. Nos. 6,416,945; 6,991,795 and 7,205,126) or as demonstrated in the following Examples.

Briefly, DNA-sequences coding for non-human papillomavirus capsid proteins such as L1 and/or L2 are first codon-optimized for expression in a cell or cell line of choice such as a eukaryotic cell or cell line, and synthesized.

The codon-optimized L1 and/or L2 DNA sequences are then cloned into the multiple cloning site of an appropriate mammalian expression vector, such as the pIRES and pBApo vectors (Clontech), pVITRO and pVIVO vectors (Invivogen), the pcDNA vectors (Invitrogen), or other commercially available mammalian expression vectors well known in the art. The codon-optimized non-human papilloma L1 and/or L2 capsid DNA sequences are operatively linked to expression control sequences allowing expression in prokaryotic or eukaryotic host cells or isolated fractions thereof in the said vector. Expression of the polynucleotide encoding the mentioned codon-optimized non-human papilloma L1 and/or L2 capsid DNA sequences comprises transcription of the DNA sequences into a translatable mRNA. Regulatory elements ensuring expression in host cells are well known in the art. In an aspect, they comprise regulatory sequences ensuring initiation of transcription and/or poly-A signals ensuring termination of transcription and stabilization of the transcript. Additional regulatory elements may include transcriptional as well as translational enhancers. Possible regulatory elements permitting expression in prokaryotic host cells comprise, e.g., the lac-, trp- or tac-promoter in *E. coli*, and examples for regulatory elements permitting expression in eukaryotic host cells are the AOX1- or the GAL1-promoter in yeast or the CMV-, SV40-, RSV-promoter (Rous sarcoma virus), CMV-enhancer, SV40-enhancer or a globin intron in mammalian and other animal cells. Moreover, inducible expression control sequences may be used in an expression vector referred to herein. Such inducible vectors may comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. As mentioned above, suitable expression vectors are known in the art such as Okayama-Berg cDNA expression vector pcDV1 (Pharmacia), pBluescript (Stratagene), pCDM8, pRc/CMV, pcDNA1, pcDNA3 (Invitrogen) or pSPORT1 (Invitrogen). Methods which are well known to those skilled in the art can be used to construct and express the codon-optimized non-human papilloma L1 and/or L2 capsid proteins referred to herein; see, for example, the techniques described in Sambrook, Molecular Cloning A Laboratory Manual, Cold Spring Harbor Laboratory (2001) N.Y. and Ausubel, Current Protocols in Molecular Biology, Green Publishing Associates and Wiley Interscience, N.Y. (1994).

For non-human papilloma virus-like particle—(VLP) or pseudovirion—(PsV) production, appropriate eukaryotic cells or cell lines as defined herein are transfected with an expression vector which allows for expression of the codon-optimized non-human papilloma L1 and/or L2 DNA sequences. For transfection, polyethyleneimine, lipofectamine, DEAE-dextran, dendrimer, polybrene, calcium phosphate, lipofectin, DOTAP, lipofectamine, CTAB/DOPE, DOTMA, electroporation or other transfection methods described in the art can be used. A reporter gene or reporter plasmid can be used for measuring transduction efficiency. Transfection efficiency can be assessed, e.g., by various PCR methods, Western blot analysis, reporter gene assays or further methods known in the art (Molecular Cloning: A Laboratory Manual, 3rd ed., Volumes 1, 2 and 3; J. F. Sambrook and D. W. Russell, ed., Cold Spring Harbor Laboratory Press, 2001).

Harvesting of VLPs and PsVs can be performed after transfection following the standard protocol of Buck et. al (C. Buck, D. Pastrana, D. Lowy, J. Schiller, in Human Papillomaviruses, C. Davy, J. Doorbar, Eds. (Humana Press, 2006), vol. 119, pp. 445-462), optionally with modifications, as described in the following Examples. For instance, polyethyleneimine can be used for transfection, instead of lipofectamine. Moreover, Percoll can be used as ultracentrifugation medium for purification, instead of OptiPrep.

The formation of non-human papillomavirus capsid structures, VLPs and PsVs can be tested by methods known in the art (C. Cerqueira et al., Efficient Production of Papillomavirus Gene Delivery Vectors in Defined In Vitro Reactions, Molecular therapy. Methods & clinical development. 5, 165-179 (2017), doi:10.1016/j.omtm.2017.04.005; Q. Zhao et al., Disassembly and reassembly of human papillomavirus virus-like particles produces more virion-like antibody reactivity, Virology journal. 9, 52 (2012), doi:10.1186/1743-422X-9-52). For example, the produced non-human papillomavirus VLPs or PsVs can be isolated and purified by density gradient ultracentrifugation and subsequently analyzed by electron microscopy. Reporter plasmids can be used as indirect evidence for transduction efficacy, as described in the following Examples.

In some embodiments, the non-human papilloma virus-like particle of the invention may be labelled or contain other modifications which allow a detection and/or analysis of a hybridization product and/or the binding to a carrier. Labelling can be done by various techniques well known in the art and depending of the label to be used. Particularly, the non-human papilloma virus-like particle of the invention may be biotinylated in order to enable binding to a streptavidin surface or fluorescent conjugate. Exemplary labels to be used in the context of the present invention are, but are not limited to, fluorescent labels comprising, inter alia, fluorochromes such as R-phycoerythrin, Cy3, Cy5, fluorescein, rhodamin, Alexa, or Texas Red. However, the label may also be an enzyme or an antibody. It is envisaged that an enzyme to be used as a label will generate a detectable signal by reacting with a substrate. Suitable enzymes, substrates and techniques are well known in the art. An antibody to be used as label may specifically recognize a target molecule which can be detected directly (e.g., a target molecule which is itself fluorescent) or indirectly (e.g., a target molecule which generates a detectable signal, such as an enzyme). The non-human papilloma virus-like particle or pseudovirus particle of the invention may also contain 5' restriction sites, locked nucleic acid molecules (LNA) or be part of a peptide nucleotide acid molecule (PNA). Such PNA can be, in principle, detected via the peptide part by, e. g., antibodies. It is further evident that the non-human papilloma virus-like particle of the invention can comprise an affinity tag used for purification purposes, like a His tag or FLAG tag or the like, well known in the art.

Preferred non-human papillomavirus types are listed in Tables 1, 2 and 3 below. Preferably, the non-human papilloma pseudovirus or virus-like particle of the invention is from *Puma concolor* papillomavirus 1 (PcPV1) or *Macaca fascicularis* papillomavirus type 11, isolate Mac1637 (MfPV11).

In a preferred embodiment of the non-human papilloma pseudovirus or virus-like particle of the invention, the papilloma capsid protein codon optimized for expression in eukaryotic cells or cell lines is L1 and/or L2. The non-human papilloma pseudovirus or virus-like particle of the invention can comprise the capsid protein L1, the capsid protein L2, or both the capsid protein L1 and the capsid protein L2. In a still further preferred embodiment, the non-human papilloma virus-like particle of the invention comprises the capsid protein L1; or the non-human papilloma virus-like particle or pseudovirus of the invention comprises the capsid proteins L1 and L2.

In another preferred embodiment of the non-human papilloma pseudovirus or virus-like particle of the invention, the papilloma capsid protein is from *Caretta caretta* papillomavirus 1, *Colobus guereza* papillomavirus 1, Common chimpanzee papillomavirus 1, *Crocuta crocuta* papillomavirus 1, *Macaca fascicularis* papillomavirus type 11, isolate Mac1637, *Macaca fascicularis* papillomavirus type 6, isolate Mac39, *Procyon lotor* papillomavirus 1, *Puma concolor* papillomavirus 1, *Rhesus* papillomavirus type 1b isolate Mac170 or *Rousettus aegyptiacus* papillomavirus type 1.

In a further preferred embodiment of the non-human papilloma virus-like particle of the invention, the codon-optimized L1 or L2 papilloma capsid protein is encoded by a nucleic acid sequence selected from the group consisting of:
  a) a nucleic acid sequence as shown in SEQ ID Nos. 1 to 20;
  b) a nucleic acid sequence encoding the amino acid sequence shown in SEQ ID Nos. 21 to 40; and
  c) a nucleic acid sequence at least 40% identical to a nucleic acid sequence in a) or b).

The term "nucleic acid" or "nucleic acid sequence" as used herein refers to a single- or double-stranded DNA molecule as well as to a RNA molecule. Encompassed by the said term is genomic DNA, cDNA, hnRNA, mRNA as well as all naturally occurring or artificially modified derivatives of such molecular species. The nucleic acid may be in an aspect a linear or circular molecule. Moreover, a nucleic acid as referred to herein may comprise additional sequences required for proper transcription and/or translation such as 5'- or 3'-UTR sequences. In light of the degeneracy of the genetic code, optimized codons are used in the nucleic acid sequences referred to in this application, as described elsewhere herein. Thereby, optimal expression in, e.g., a eukaryotic cell or cell line such as a human cell or cell line can be achieved.

In addition to the aforementioned specific nucleic acid sequences SEQ ID Nos. 1 to 20 encoding the codon-optimized non-human papilloma capsid proteins L1 and L2 depicted in SEQ ID Nos. 21 to 40, the present application provides also variants of nucleic acid sequences coding for codon-optimized non-human papilloma capsid proteins L1 and L2. A variant as referred to in accordance with the present invention shall have a nucleic acid sequence which differs due to at least one amino acid substitution, deletion and/or addition wherein the amino acid sequence of the variant is still, preferably, at least 40%, 50%, 60%, 70%, 75%, 80%, 85%, 90%, 95%, 96%, 97%, 98%, or 99% identical with the nucleic acid sequence coding for the specific codon-optimized capsid proteins mentioned above. The degree of identity between two nucleic acid or amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. Preferably, the alignment is over the entire nucleic acid sequences to be compared, or over the entire amino acid sequences to be compared. The percentage is calculated by determining the number of positions at which the identical nucleotides or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman, by the homology alignment algorithm of Needleman and Wunsch, by the search for similarity method of Pearson and Lipman, by computerized implementations of these algorithms GAP, BESTFIT, BLAST, PASTA, and TFASTA in the Wisconsin Genetics Software Package, Genetics Computer Group (GCG), 575 Science Dr., Madison, WI, or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Moreover, the variants referred to herein include fragments of the nucleic acid sequences coding for the codon-optimized capsid proteins or the aforementioned types of variants as long as these fragments have the essential immunological and biological properties as referred to herein. The variant shall be capable of forming a non-human papilloma virus-like particle or PsV as defined herein.

In a preferred embodiment, the non-human papilloma pseudovirus or virus-like particle of the invention is for gene transfer or gene delivery in vitro or in vivo.

Means and methods for adapting non-human papilloma pseudovirus or virus-like particles of the invention for gene delivery in vitro and/or in vivo are well described in the art (see, e.g., Sambrook, Molecular Cloning A Laboratory Manual, Cold Spring Harbor Laboratory (2001) N.Y. and Ausubel, Current Protocols in Molecular Biology, Green Publishing Associates and Wiley Interscience, N.Y. (1994).

Briefly, the non-human papilloma pseudovirus or virus-like particle of the invention is loaded with a nucleic acid or gene of interest for gene delivery in vitro or in vivo. For instance, the gene of interest can be a reporter gene. In other cases, it can be a nucleic acid sequence to be transfected to a cell. In still further cases, it can be a nucleic acid used for gene therapy or vaccination in subjects, as defined elsewhere herein. Optimization of the transfection efficiency and optimization of the harvesting of VLPs and PsVs is within the skills of the practitioners in the field. For analysis, the VLPs and PsVs are preferably transferred to new cells. As evident to those skilled in the art, if the non-human papilloma pseudovirus or virus-like particle of the invention is loaded with a plasmid, the plasmid shall contain an eukaryotic origin of replication (SV40 origin).

Non-human papilloma pseudovirus or virus-like particles of the invention are interesting candidates as DNA delivery vectors in vitro and/or in vivo, because of their stability due to being non-enveloped, their ability to package foreign DNA without the need of a specific packaging sequence and—depending on the type of papillomavirus—their capability to infect mucosal tissue. Additionally, the viral capsid might provide some adjuvant effect by stimulating the innate immune system.

For example, human kidney epithelial cells, HEK293T or HeLa cells can be used for in vitro gene delivery. Preferably, the human cell line is HEK293T. HEK-293 cells were originally generated by treating a human embryonic kidney homogenate with sheared adenovirus DNA. The HEK293T line can also be used for production of recombinant proteins of interest. Recombinant protein production can be achieved, e.g., by placing the gene of interest under control of an appropriate promoter, such as the human elongation factor 1 alpha (EF1) housekeeping promoter.

Gene transfer in vivo can be utilized, e.g., for gene therapy or vaccination in animals, preferably mammals, even more preferred humans, as set forth elsewhere herein. Importantly, it has been found in the following Examples that mice never showed any signs of adverse reaction or inflammation at the site of infection of the non-human papilloma pseudovirus or virus-like particle of the invention.

In another preferred embodiment, the non-human papilloma pseudovirus or virus-like particle further comprises a targeting peptide. The term "targeting peptide" means a peptide sequence that serves to target or direct the non-human papilloma pseudovirus or virus-like particle to a particular location, cell type, diseased cell or tissue, or cell association. The targeting peptide is directed against a specific target molecule and allows concentration of the non-human papilloma pseudovirus or virus-like particle carrying a gene or nucleic acid of interest, or loaded with an agent such as a diagnostic agent, imaging agent or therapeutic agent as defined herein, in a particular localization within a subject. Accordingly, the targeting peptide targets the non-human papilloma pseudovirus or virus-like particle to specific tissues and/or cells in vitro and/or in vivo. Preferably, said target peptide is capable of directing the non-human papilloma pseudovirus or virus-like particle of the invention to one or more specific sites of the animal organism, mammal organism or preferably human organism, in vivo. Suitable targeting peptides and appropriate positions for including said target peptides into the codon-optimized non-human papilloma L1 or L2 capsid protein are well described in the art (see, e.g., WO 2011/039646 and references cited therein).

Preferably, the targeting peptide is capable of directing the non-human papilloma pseudovirus or virus-like particle to human cells selected from the group consisting of: liver cells, lung cells, heart cells, kidney cells, blood cells, brain cells, gut cells, stem cells, cells of the mucosa of the throat or the nose, or cancer cells.

The invention further relates to a pharmaceutical composition comprising the non-human papilloma pseudovirus or virus-like particle of the invention, and an agent selected from the group consisting of: a diagnostic agent, an imaging agent, and a therapeutic agent.

The term "pharmaceutical composition" as used herein refers to mixture comprising the non-human papilloma pseudovirus or virus-like particle of the invention, and an agent selected from the group consisting of: a diagnostic agent, an imaging agent, and a therapeutic agent. Moreover, the pharmaceutical composition of the invention may comprise further components as well such as further therapeutic or auxiliary ingredients and/or pharmaceutically acceptable carriers and/or diluents. Preferably, such further ingredients of the pharmaceutical composition of the invention can be buffers, diluents, stabilizing agents, wetting agents, pharmaceutical carriers, additional pharmaceutically active agents, release controlling agents and the like.

Preferably, the pharmaceutical composition of the present invention is to be used as a medicament. Said medicament is applied to treat and/or prevent a disease or disorder selected from the group consisting of: neurological diseases, stroke, ischemia, cancer, age-related disease, genetic disorder, allergy, auto-immune disease, an infection by bacteria, virus, fungus or parasite.

Pharmaceutical compositions comprising papilloma virus like particles are well described in the art (see, e.g., WO 2011/039646; U.S. Pat. Nos. 6,416,945; 6,991,795 and 7,205,126).

The term "diagnostic agent" as referred to herein means a compound used to detect the impaired function of a cell, tissue or body organ, or to detect abnormalities in a cell, tissue or body organ tissue structure. Diagnostic agents are well described in the literature. The term "diagnosing" as used herein refers to assessing the probability according to which a subject, preferably a human subject, is suffering or will suffer from a disease or condition referred to in this specification. As will be understood by those skilled in the art, such an assessment is usually not intended to be correct for 100% of the subjects to be diagnosed. The term, however, requires that a statistically significant portion of subjects can be correctly diagnosed to suffer from the disease or condition. Whether a portion is statistically significant can be determined by the methods described herein above. Preferably, one or more symptoms associated with a disease as referred to herein can be diagnosed by the administration of a non-human papilloma pseudovirus or virus-like particle of the invention comprising a diagnosing agent. For example, a diagnostic agent can be a labelled antibody, labeled nucleic acid such as siRNA, luciferase or other chemoluminescent agents, a biomarker or radionuclide or the like.

The term "imaging agent" as used herein denotes biomarkers for diagnosing a disease, monitoring disease progression, tracking a therapeutic response, and enhancing the knowledge of physiology and pathophysiology. For example, imaging agents include positron emission tomography and single-photon emission computed tomography tracers. Preferably, one or more symptoms associated with a disease as referred to herein can be imaged by the administration of a non-human papilloma pseudovirus or virus-like particle of the invention comprising an imaging agent.

The pharmaceutical composition comprising a non-human papilloma pseudovirus or virus-like particle of the invention and an imaging agent or a diagnostic agent can be used for imaging or diagnosing diseases or disorders in a subject as defined herein.

The term "therapeutic agent" as referred to herein is a gene, substance or compound capable of producing a curative effect in a disease state. The term "treatment or treating" as used herein denotes the improvement or even elimination of one or more symptoms associated with a disease as referred to herein, by the administration of a non-human papilloma pseudovirus or virus-like particle of the invention comprising a therapeutic agent. An improvement may also be seen as a slowing or stopping of the progression of a disease as set forth herein. The pharmaceutical composition comprising a non-human papilloma pseudovirus or virus-like particle of the invention and a therapeutic agent can be utilized for prevention or therapy of various diseases or disorders in a subject as specified elsewhere herein. The term "preventing" as used herein refers to avoiding the onset of a disease or at least one symptom thereof. The term "therapeutic agent" as used herein comprises a vaccine. A vaccine is a biological preparation that provides active acquired immunity to a particular disease. A vaccine typically contains an agent that resembles a disease-causing microorganism or virus and is often made from weakened or killed forms of the microbe or virus, its toxins or one of its surface proteins. The agent stimulates the body's immune system to recognize the agent as a threat, destroy it, and recognize and destroy any of these microorganisms or viruses that it later encounters. Vaccines can be prophylactic, i.e. they prevent or ameliorate the effects of a future infection by a natural or "wild" pathogen, or therapeutic, e.g., vaccines against cancer. The effectiveness of vaccination has been widely studied and verified; for example, the influenza vaccine, the HPV vaccine, and the chicken pox vaccine. The World Health Organization (WHO) reports that licensed vaccines are currently available for twenty-five different preventable infections, in its global vaccine action plan 2011 to 2020. The administration of vaccines is called "vaccination". Vaccination is the most effective method of preventing infectious diseases; widespread immunity due to vaccination is largely responsible for the worldwide eradication of smallpox and the restriction of diseases such as polio, measles, and tetanus from much of the world.

According to the present invention, the pharmaceutical composition shall, preferably, comprise the non-human papilloma pseudovirus or virus-like particle of the invention, and a therapeutic agent in a therapeutically effective dose. Therapeutic efficacy and toxicity of the pharmaceutical composition of the invention can be determined by standard pharmaceutical procedures as describe elsewhere herein. The pharmaceutical composition shall further be adapted for use in treating and/or preventing a disease or disorder as described elsewhere herein. The desired mode of administration is set forth below. Formulations and preparations methods for formulating a composition as a medicament are well known in the art and include, for example, mixing, granulating, compression or dissolving the ingredients as appropriate to form the desired composition. Typically, the therapeutically active ingredients will be mixed and, preferably, combined them with a pharmaceutically acceptable carrier and/or diluent. Moreover, it is known by those skilled in the art that the formulation of a pharmaceutical composition to be used as a medicament shall take place under GMP conditions that will ensure quality, pharmaceutical security, and effectiveness of the medicament.

The term "reporter gene" as used herein means a gene that is attached to a regulatory sequence of another gene of interest in bacteria, yeast, insects, cell culture, animals, plants or human. Certain genes are chosen as reporters because the characteristics they confer on organisms expressing them are easily identified and measured, or because they are selectable markers. Reporter genes are often used as an indication of whether a certain gene has been taken up by or expressed in the cell or organism population. Commonly used reporter genes that induce visually identifiable characteristics usually involve fluorescent and luminescent proteins. Examples include the gene that encodes jellyfish green fluorescent protein (GFP), which causes cells that express it to glow green under blue light, the enzyme luciferase, which catalyzes a reaction with luciferin to produce light, and the red fluorescent protein from the gene dsRed. A common reporter in bacteria is the *E. coli* lacZ gene, which encodes the protein beta-galactosidase. This enzyme causes bacteria expressing the gene to appear blue when grown on a medium that contains the substrate analog X-gal. An example of a selectable-marker which is also a reporter in bacteria is the chloramphenicol acetyltransferase (CAT) gene, which confers resistance to the antibiotic chloramphenicol.

Methods for producing a non-human papilloma pseudovirus or virus-like particle of the invention, packaging it with a diagnostic agent, imaging agent, or therapeutic agent, optionally in combination with a reporter gene, and targeted delivery thereof to a subject are well described in the literature (see, e.g., Buck, C., et al (2006a). Generation of HPV Pseudovirions Using Transfection and Their Use in Neutralization Assays. In Human Papillomaviruses, C. Davy and J. Doorbar, eds. (Humana Press), pp. 445-462, doi: 10.1385/1-59259-982-6:445; U.S. Pat. Nos. 6,416,945; 6,991,795 and 7,205,126). Preferably, the non-human papilloma pseudovirus or virus-like particle of the invention, comprising a diagnostic agent, imaging agent, or therapeutic agent, optionally in combination with a reporter gene, is formulated as a pharmaceutical composition or medicament.

The term "subject" as used herein relates to insects (e.g. bees), an animal such as a rodent (mouse or rat), pet (cat, hamster, rabbit, dog), farming animal (sheep, poultry, goat, cow, horse) preferably mammal such as a non-human primate (macaque, marmoset, tamarin, spider monkey, owl monkey, vervet monkey, squirrel monkey, and baboon), and, more preferably, human.

Preferably, the therapeutic agent is selected from the group consisting of: (i) a small molecule, preferably a cytotoxic drug; (ii) a RNAi nucleic acid; (iii) a microRNA; (iv) a ribozyme; (v) an antisense nucleic acid; (vi) a morpholino; (vii) an antibody; and (viii) CRISPR/Cas. The therapeutic agent can also be a combination of two or more of the mentioned compounds, e.g. a combination of at least two cytotoxic drugs, at least a small molecule and an antibody, at least a cytotoxic drug and an antibody, at least a microRNA and antisense nucleic acid, or any further suitable combination of (i) to (viii) listed above.

The non-human papilloma pseudovirus or virus-like particle of the invention can contain a small molecule as a therapeutic agent. The term "small molecule" as used herein relates to a molecule with a low molecular weight. Typically, a small molecule is an organic compound with a molecular weight of less than 900 daltons. Small molecules include, for example, small secondary metabolites such as alkaloids, lipids, glycosides, terpenes, tetrapyrroles, phenazines, oliogonucleotides and small peptides or peptide-like molecules.

The small molecule is preferably a cytotoxic drug. The term "cytotoxic drug" as referred to herein denotes cytotoxic drugs or cytostatics (also cytotoxic chemotherapy) are drugs used to destroy proliferating cells such as cancer cells. Cytotoxic drugs inhibit cell division and in this way cause cancer cells to die. Cytotoxic drugs are transported in the bloodstream throughout the body. Cytotoxic drugs can be used to destroy tumors, boost the outcomes of surgery or radiotherapy, reduce metastases and alleviate cancer symptoms. Cytostatics can be effective outside the primary tumour and also destroy small tumors that have not been detected in tests. Cytotoxic drugs affect all dividing cells, including those of healthy tissue. But because cancer cells often divide markedly faster than normal cells, they are particularly sensitive to cytostatics. The effects on normal cells are less pronounced and healthy cells also recover faster. The role of cytotoxic drugs in cancer therapy has decreased slightly with the development of drug therapy. However, they continue to be widely used. Several types of cytotoxic drugs are used in cancer therapy that together have different kinds of effect. The most usual method is to administer a combination of several different cytotoxic drugs. The effectiveness of chemotherapy depends on the type of tumor, its composition, rate of development and proportion of cells in the distribution stage. Cytotoxic drugs are well described in the literature.

The non-human papilloma pseudovirus or virus-like particle of the invention can contain a ribozyme, as a therapeutic agent. The term "ribozyme" as referred to herein relates to an RNA molecule that is capable of catalyzing specific biochemical reactions, including cleavage and/or ligation of RNA and DNA and peptide bond formation. Methods of designing and constructing ribozymes are known in the art and include, for example, de novo rational design, oligonucleotide synthesis and in vitro-transcription. It is also known in the art that ribozymes can be stably integrated or transiently introduced into cells as part of a recombinant DNA construct such as a plasmid or vector. It will be understood that such a DNA construct may contain additional regulatory elements such as an enhancer, a constitutive or inducible promoter or a terminator.

The non-human papilloma pseudovirus or virus-like particle of the invention can contain an antibody, as a therapeutic agent. The term "antibody" as used herein, also referred to as immunoglobulin, includes both polyclonal and monoclonal antibodies, as well as fragments thereof, such as Fv, Fab and F(ab)2 fragments that are capable of binding an antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art.

The non-human papilloma pseudovirus or virus-like particle of the invention can contain an inhibitory RNA molecule, as a therapeutic agent. The term "inhibitory RNA molecule" as used herein refers to an RNA molecule that inhibits gene expression in a sequence-specific manner. Inhibitory RNA molecules include, for example, small interfering RNA (siRNA), small hairpin RNAs (shRNA) and microRNA (miRNA). The inhibitory RNA molecule typically induces a process known as RNA interference (RNAi), leading to cleavage and/or translational inhibition of a target mRNA with a complementary sequence. It is known to those skilled in the art that the inhibitory RNA molecule can show perfect or imperfect base-pairing to a complementary target sequence. siRNA and shRNAs typically base-pair perfectly and induce mRNA cleavage only in a single, specific target. On the contrary, miRNAs usually have incomplete base pairing to a target and often inhibit the translation of many different mRNAs with similar sequences. An inhibitory RNA molecule may be chemically synthesized or expressed within the cell, for example by introduction of respective recombinant DNA construct. It will be understood that such a DNA construct may contain additional regulatory elements such as an enhancer, a constitutive or inducible promoter or a terminator.

The non-human papilloma pseudovirus or virus-like particle of the invention can contain an antisense oligonucleotide, as a therapeutic agent. An "antisense oligonucleotide" as used herein refers to a single strand DNA and/or RNA molecule that is capable of interfering with DNA and/or RNA processing. Antisense oligonucleotides comprise a nucleic acid sequence which is complementary to a specific RNA or DNA sequence. Typically, an antisense oligonucleotide will bind, in a sequence-specific manner, to their respective complementary oligonucleotides, DNA, or RNA, thereby interfering with DNA and/or RNA processing. It is known to those skilled in the art that antisense oligonucleotides may interfere with mRNA processing through RNase H-mediated degradation, translational arrest, modulation of splicing or they may act through steric hindrance of proteins. Means and methods for the design and synthesis of antisense oligonucleotides are well known in the art and include, for example, rational design, chemical modifications and design of antisense oligonucleotides containing locked nucleic acids (LNA) as well as solid-phase chemical synthesis. Antisense oligonucleotides can be chemically synthesized or expressed within the cell, for example by introduction of respective recombinant DNA construct. It will be understood by those skilled in the art that such a DNA construct may contain additional regulatory elements such as an enhancer, a constitutive or inducible promoter or a terminator. Preferably, the antisense oligonucleotide has a length of at least 8, at least 10, at least 12, at least 15, at least 20, at least 25, at least 30, at least 40, at least 45, at least 50 or more nucleotides. The antisense oligonucleotide may comprise deoxyribonucleotides, ribonucleotides, or a combination of both.

The non-human papilloma pseudovirus or virus-like particle of the invention can contain a morpholino, as a therapeutic agent. The term "morpholino" as used herein relates to a molecule that blocks access of other molecules to small, specific sequences of the base-pairing surfaces of a RNA. Typically, said small specific sequences have a length of about 25 nucleotides. In general, a morpholino comprises a backbone of methylenemorpholine rings and phosphorodiamidate linkages. Morpholinos are commonly also known as morpholino oligomers (MO nucleic acid analogs) and phosphorodiamidate morpholino oligomers (PMO). Morpholinos typically do not lead to degradation of their target RNA molecules, but rather act by sterical blocking, i.e. binding to a target sequence within an RNA and thereby getting in the way of molecules that may otherwise interact with said RNA.

The non-human papilloma pseudovirus or virus-like particle of the invention can contain the (CRISPR/Cas) system. The CRISPR/Cas system has been reviewed, e.g., by Horvath and Barrangou (Science. 2010 Jan. 8; 327(5962):167-70. doi: 10.1126/science.1179555). Engineered DNA-binding molecules such as the clustered regularly interspaced short palindromic repeats (CRISPR) and CRISPR-associated proteins (Cas) (CRISPR/Cas) system have been used extensively for genome editing in cells of various types and species. The sequence-specific DNA-binding activities of these engineered DNA-binding molecules can also be utilized for other purposes, such as transcriptional activation, transcriptional repression, chromatin modification, visualization of genomic regions, and isolation of chromatin in a locus-specific manner (Fujita and Fujii, Int J Mol Sci. 2015 October; 16(10): 23143-23164; Gaj et al., Trends in Biotechnology 2013, 31, p. 397-405). For example, the CRISPR/Cas system allows editing of the mouse genome much faster than the previously used techniques and more importantly multiple mutations can be created in a single experiment (Harms et al., Curr Protoc Hum Genet. 2014; 83: 15.7.1-15.7.27.).

The disease to be imaged, diagnosed or treated by the pharmaceutical composition is preferably neurological diseases, stroke, ischemia, cancer, an age-related disease, a genetic disorder, an allergy, an auto-immune disease, an infection by bacteria, virus, fungus or parasite.

The term "cancer" as used herein relates to a disease that is characterized by an uncontrolled growth of aberrant cells. Cancer includes pre-cancerous states well as a manifested or advanced disease states. The classification of a cancer or tumor stage as well as characteristics and symptoms are known in the art and can, for example, be found in the standard text books of medicine, such as Stedman or Pschyrembl. It is understood by those skilled in the art that cancer cells may migrate from the original tumor site and spread to distant site, also known as dissemination and metastasis formation. Examples of cancers include breast cancer, colorectal cancer, pancreatic cancer, prostate cancer, ovarian cancer, cervical cancer, skin cancer, renal cancer, liver cancer, brain cancer, lymphoma, leukemia and lung cancer.

Therapeutic efficacy and toxicity of the pharmaceutical composition according to the present invention can be determined by standard pharmaceutical procedures, e.g. in experimental animals. For example, the so-called ED50 describes the dose therapeutically effective in 50% of the population and the so-called LD50 describes the dose lethal to 50% of the population. The dose ratio between therapeutic and toxic effects is the therapeutic index, and it can be expressed as the ratio, LD50/ED50. The dosage regimen will be determined by the attending physician and by clinical factors. As is well known in the medical arts, dosages for any one patient depends upon many factors, including the patient's size, age, the particular formulation of the medicament to be administered, sex, time and route of administration, general health, and other drugs being administered concurrently. Progress can be monitored by periodic assessment. Dosage recommendations shall be indicated in the prescribers or users instructions in order to anticipate dose adjustments depending on the considered recipient.

In another preferred embodiment, the therapeutic agent is a nucleic acid. Preferably, the nucleic acid is a nucleic acid for gene therapy or vaccination.

The non-human papilloma pseudovirus or virus-like particle of the invention can comprise a gene for gene therapy, as a therapeutic agent. As well known in the art, gene therapy is the insertion of genes into an individual's cells and tissues to treat a disease, and hereditary diseases in which a defective mutant allele is replaced with a functional one.

In somatic cell gene therapy, the therapeutic genes are transferred into any cell other than a gamete, germ cell, gametocyte or undifferentiated stem cell. In germline gene therapy, germ cells (sperm or egg cells) are modified by the introduction of functional genes into their genomes. Modifying a germ cell causes all the organism's cells to contain the modified gene. The change is therefore heritable and passed on to later generations. It is envisaged that the defective gene is either replaced or disrupted. Gene therapeutic approaches using the pharmaceutical composition of the invention include but are not limited to the treatment of retinal diseases Leber's congenital amaurosis, choroideremia, X-linked SCID, ADA-SCID, adrenoleukodystrophy, chronic lymphocytic leukemia (CLL), acute lymphocytic leukemia (ALL), multiple myeloma, haemophilia, peripheral artery disease, including critical limb ischemia and Parkinson's disease.

Alternatively, the non-human papilloma pseudovirus or virus-like particle of the invention can include a DNA (or RNA) for vaccination. The term "vaccine" has been defined elsewhere herein. DNA vaccination is a technique for protecting against disease by injection with genetically engineered DNA so cells directly produce an antigen, producing a protective immunological response. DNA vaccines have potential advantages over conventional vaccines, including the ability to induce a wider range of immune response types. Preferably, vaccination is for Respiratory Syncytial Virus (Grunwald T. et al., 2014. Novel vaccine regimen elicits strong airway immune responses and control of respiratory syncytial virus in nonhuman primates. doi: 10.1128/JVI.02736-13; Kohlmann, R. et al., (2009). Protective efficacy and immunogenicity of an adenoviral vector vaccine encoding the codon-optimized F protein of respiratory syncytial virus. Journal of virology 83, 12601-12610; Ternette, N. et al., (2007). Immunogenicity and efficacy of codon optimized DNA vaccines encoding the F-protein of respiratory syncytial virus. Vaccine 25, 7271-7279; Grunwald T, Ulbert S. 2015 Improvement of DNA vaccination by adjuvants and sophisticated delivery devices: vaccine-platforms for the battle against infectious diseases. doi: 10.7774/cevr.2015.4.1.1.).

The pharmaceutical composition of the invention comprising a nucleic acid for vaccination is safe enough to be administered without danger of clinical infection, do not have toxic side effects, can be administered by an effective route, are stable, and are compatible with vaccine carriers. The vaccines may be administered by a variety of routes, such as orally, parenterally, subcutaneously, mucosally, intravenously or intramuscularly. The vaccine may be used in dosage forms such as capsules, suspensions, elixirs, or liquid solutions. The vaccine may be formulated with an immunologically acceptable carrier or adjuvant, or other excipients. The vaccines are administered in therapeutically effective amounts sufficient to generate an immunologically protective response. The vaccine may be administered in single or multiple doses.

The nucleic acid can be DNA or RNA which can be wildtype, recombinant or chemically synthesized.

Suitable formulations of pharmaceutical compositions comprising the non-human papilloma pseudovirus or virus-like particle of the invention, and nucleic acid as a therapeutic agent for gene therapy or vaccination are known in the art (see, e.g., WO 2011/039646; U.S. Pat. Nos. 6,416, 945; 6,991,795 and 7,205,126).

In a preferred embodiment of the pharmaceutical composition of the invention, the pharmaceutical composition further comprises a pharmaceutically acceptable carrier.

A pharmaceutically acceptable carrier according to the present invention must be acceptable in the sense of being compatible with the other ingredients of the formulation and not being deleterious to the recipient thereof. Pharmaceutical carriers may include solid, gel, or liquid carriers such as lactose, terra alba, sucrose, talc, gelatin, agar, pectin, acacia, magnesium stearate, stearic acid, glyceryl mono-stearate or glyceryl distearate. Moreover, further suitable carriers are known in the art and can be found for example in science text books such as Remington's Pharmaceutical Sciences, Mack Publishing Company, Easton, Pennsylvania.

In a still further preferred embodiment of the pharmaceutical composition of the invention, the pharmaceutical composition is to be administered by intramuscular injection or via the cutaneous route. Preferably, the pharmaceutical composition is to be administered via intramuscular injection.

As the preferred site of entry of different non-human papillomavirus genera can be either cutaneous or mucosal it is necessary to take this into account when choosing the route of administration for the pharmaceutical composition of the invention. Preferably, the pharmaceutical composition of the invention is to be administered by intramuscular injection or via the cutaneous route, even more preferred via intramuscular injection. It is known to the skilled artisan, that administration and dosage of a therapeutic agent depends on various factors such as the health state of the subject and the disease to be treated.

Moreover, the invention pertains to a non-human papilloma pseudovirus or virus-like particle of the invention for use as a medicament. Preferably, the medicament is for the treatment of a disease selected from the group consisting of Neurological diseases, stroke, ischemia, cancer, age-related disease, genetic disorder, allergy, auto-immune disease, infection by bacteria, virus, fungus or parasite.

The terms "medicament" and "pharmaceutical composition" are used interchangeably herein.

In another embodiment, the medicament is for gene therapy or vaccination.

The definition and explanations given herein above apply mutatis mutandis to the following methods and uses of the present invention.

The invention also relates to a method for treating and/or preventing a disease selected from the group consisting of: neurological diseases, stroke, ischemia, cancer, age-related disease, genetic disorder, allergy, auto-immune disease, infection by bacteria, virus, fungus or parasite in a subject in need thereof comprising administering to said subject a non-human papilloma pseudovirus or virus-like particle comprising a therapeutic agent described herein, in a therapeutically effective amount.

Furthermore, the invention relates to a method for producing a non-human papilloma pseudovirus or virus-like particle comprising the steps of:
  a) codon-optimizing of a DNA-sequence coding for a non-human papillomavirus capsid protein L1 and/or L2, for expression in eukaryotic cells or cell lines, preferably human cells or cell lines;
  b) synthesizing of the sequence of step a) and cloning of the synthesized sequence into an expression vector; and
  c) transfecting of the expression vector of step b) into a cell, thereby producing non-human papilloma pseudovirus or virus-like particles.

In this method of the invention, a non-human papilloma pseudovirus or virus-like particle of the invention is produced by first codon-optimizing a DNA sequence coding for the non-human papilloma L1 and/or L2 capsid protein as defined herein, for expression in eukaryotic cells or cell lines, preferably human cells or cell lines. Thereafter, the mentioned sequence is synthesized and cloned into an expression vector, preferably a mammalian expression vectors. The expression vector is then introduced into appropriate cells such as eukaryotic cells or cell lines, preferably human cells or cell lines, for expression of the codon-optimized non-human papilloma L1 and/or L2 capsid proteins and production of the non-human papilloma virus-like particles of the invention in the mentioned cells or cell lines. Preferred non-human papillomaviruses, capsid proteins L1 and/or L2, and cells are indicated elsewhere herein.

Moreover, the invention relates to the use of ι-carrageenan as transduction enhancer for non-human papilloma pseudovirus or virus-like particles in vitro.

Unexpectedly, it has been found by the inventors that ι-carrageenan induced an increase in transduction efficiency of cells when transduced with non-human papilloma virus-like particles from PcPV1, PlPV1, CcrPV1 and MmPV1. Therefore, ι-carrageenan can be utilized for improving transduction of non-human papilloma virus-like particles, preferably from PcPV1, PlPV1, CcrPV1 and MmPV1.

All references cited in this specification are herewith incorporated by reference with respect to their entire disclosure content and the disclosure content specifically mentioned in this specification.

Tables
Table 1: Corresponds to Table 1 of the publication by A. Rector and M. van Ranst (2013).

TABLE 1

Overview of genomically characterized non-human papillomaviruses.

| Host species taxonomic order | Host species | | Papillomavirus name | Abbreviation (previous) | Classification | # bp | Accession no. | Isolated from | Reference |
|---|---|---|---|---|---|---|---|---|---|
| Artiodactyla | European elk | *Alces alces* | Alces alces papillomavirus 1 | AaPV1 (EEPV) | Deltapapillomavirus 1 | 8095 | M15953 | Cutaneous fibroma | Ahola et al. (1986) |
| | Yak | *Bos grunniens* | Bos grunniens papillomavirus 1 | BgPV1 | Deltapapillomavirus 4$^n$ | 7946 | JX174437 | Cutaneous fibropapilloma | Zhu et al. (2013) |
| | Domestic cow | *Bos taurus* | Bos taurus papillomavirus 1 | BPV1 | Deltapapillomavirus 4 | 7945 | X02346$^{nn}$ | Cutaneous fibropapilloma | Chen et al. (1982) |
| | | | Bos taurus papillomavirus 2 | BPV2 | Deltapapillomavirus 4 | 7937 | M20219 | Cutaneous fibropapilloma | Groff and Lancaster (unpublished) |
| | | | Bos taurus papillomavirus 3 | BPV3 | Xipapillomavirus 1 | 7276 | AF486184 | Cutaneous papilloma | Terai et al. (2002) |
| | | | Bos taurus papillomavirus 4 | BPV4 | Xipapillomavirus 1 | 7265 | X05817 | Oral/esophageal papilloma | Patel et al. (1987) |
| | | | Bos taurus papillomavirus 5 | BPV5 | Epsilonpapillomavirus 1 | 7841 | AF457465 | Udder fibropapilloma | Terai et al. (2002) |
| | | | Bos taurus papillomavirus 6 | BPV6 | Xipapillomavirus 1 | 7296 | AJ620208 | Udder papilloma | Jarrett et al. (1984) |
| | | | Bos taurus papillomavirus 7 | BPV7 | Dyoxipapillomavirus 1$^n$ | 7412 | DQ217793 | Teat papilloma and healthy skin | Ogawa et al. (2007) |
| | | | Bos taurus papillomavirus 8 | BPV8 | Epsilonpapillomavirus 1 | 7791 | DQ098913 | Cutaneous papilloma | Tomita et al. (2007) |
| | | | Bos taurus papillomavirus 9 | BPV9 | Xipapillomavirus 1 | 7303 | AB331650 | Teat papilloma | Hatama et al. (2008) |
| | | | Bos taurus papillomavirus 10 | BPV10 | Xipapillomavirus 1 | 7399 | AB331651 | Teat papilloma | Hatama et al. (2008) |
| | | | Bos taurus papillomavirus 11 | BPV11 | Xipapillomavirus 1 | 7251 | AB543507 | Cutaneous papilloma | Hatama et al. (2011) |
| | | | Bos taurus papillomavirus 12 | BPV12 | Xipapillomavirus 2$^n$ | 7197 | JF834523 | Tongue epithelial papilloma | Zhu et al.) (2012 |
| | | | Bos taurus papillomavirus 13 | BPV13 | Deltapapillomavirus 4$^n$ | 7961 | JQ798171 | Ear cutaneous papilloma | Lunardi et al. (2013) |
| | Arabian camel | *Camelus dromedarius* | Camelus dromedarius papillomavirus 1 | CdPV1 | Deltapapillomavirus 6$^n$ | 7679 | HQ912790 | Cutaneous fibropapilloma | Ure et al. (2011) |
| | | | Camelus dromedarius papillomavirus 2 | CdPV2 | Deltapapillomavirus 6$^n$ | 7906 | HQ912791 | Cutaneous fibropapilloma | Ure et al. (2011) |
| | Domestic goat | *Capra hircus* | Capra hircus papillomavirus 1 | ChPV1 | Phipapillomavirus 1 | 7542 | DQ091200 | Healthy skin | Van Doorslaer et al. (2006) |
| | Western roe deer | *Capreolus capreolus* | Capreolus capreolus papillomavirus 1 | CcaPV1 (RdPV1, CcPV1) | Deltapapillomavirus 5 | 8032 | EF680235 | Cutaneous fibropapilloma | Erdelyi et al. (2008) |
| | White-tailed deer | *Odocoileus virginianus* | Odocoileus virginianus papillomavirus 1 | OvPV1 (DPV) | Deltapapillomavirus 2 | 8374 | M11910$^{nnn}$ | Cutaneous fibroma | Groff and Lancaster (1985) |
| | Domestic sheep | *Ovis aries* | Ovis aries papillomavirus 1 | DaPV1 (OvPV1) | Deltapapillomavirus 3 | 7761 | U83594 | Cutaneous fibropapilloma | Karlis et al. (unpublished) |
| | | | Ovis aries papillomavirus 2 | OaPV2 (OvPV2) | Deltapapillomavirus 3 | 7758 | U83595 | Cutaneous fibropapilloma | Karlis et al. (unpublished) |
| | | | Ovies aries papillomavirus 3 | OaPV3 | Dyolambdapapillomavirus 1 | 7334 | FJ796965 | Squamous carcinoma | Alberti et al. (2010) |
| | Reindeer | *Rangifer tarandus* | Rangifer tarandus papillomavirus 1 | RtPV1 (RPV) | Deltapapillomavirus 1 | 8090 | AF443292 | Cutaneous fibropapilloma | Terai et al. (2002) |

TABLE 1-continued

Overview of genomically characterized non-human papillomaviruses.

| Host species taxonomic order | Host species | Papillomavirus name | Abbreviation (previous) | Classification | # bp | Accession no. | Isolated from | Reference |
|---|---|---|---|---|---|---|---|---|
| | Domestic pig | Sus scrofa domesticus | Sus scrofa domesticus papillomavirus 1 | SsPV1 | Dyodeltapapillomavirus 1 | 7260 | EF395818 | Healthy skin | Stevens et al. (2008b) |
| Carnivora | Domestic dog (Shar Pei) | Canis lupus familiaris | Canis familiaris oral papillomavirus | CPV1 (COPV) | Lambdapapillomavirus 2 | 8607 | D55633 | Oral/cutaneous papilloma | Delius et al. (1994) |
| | Domestic dog (Golden retriever) | | Canis familiaris papillomavirus 2 | CPV2 (CfPV2) | Taupapillomavirus 1 | 8101 | AY722648 | Cutaneous papilloma on footpad | Yuan et al. (2007) |
| | Domestic dog (Rhodesian ridgeback) | | Canis familiaris papillomavirus 3 | CPV3 | Chipapillomavirus 1 | 7801 | DQ295066 | Malignant EV lesion | Tobler et al. (2006) |
| | Domestic dog (European pug) | | Canis familiaris papillomavirus 4 | CPV4 | Chipapillomavirus 2 | 7742 | EF584537 | Pigmented lesion | Tobler et al. (unpublished) |
| | Domestic dog | | Canis familiaris papillomavirus 5 | CPV5 | Chipapillomavirus 1 | 7810 | FJ492743 | Pigmented plaque | Lange et al. (2009a) |
| | Domestic dog | | Canis familiaris papillomavirus 6 | CPV6 | Lambdapapillomavirus 3 | 8242 | FJ492744 | Inverted papilloma | Lange et al. (2009a) |
| | Domestic dog | | Canis familiaris papillomavirus 7 | CPV7 | Taupapillomavirus 1 | 7955 | FJ492742 | In situ quamous cell carcinoma | Lange et al. (2009a) |
| | Domestic dog (Dachshund-mix) | | Canis familiaris papillomavirus 8 CPV8 | | Chipapillomavirus 3[n] | 7784 | HQ262536 | Pigmented plaque | Lange et al. (2012b) |
| | Domestic dog (mixed-breed blood hound) | | Canis familiaris papillomavirus 9 CPV9 | | Chipapillomavirus 1[n] | 7873 | JF800656 | Pigmented plaque | Yuan et al. (2012) |
| | Domestic dog | | Canis familiaris papillomavirus 10 | CPV10 | Chipapillomavirus 3[n] | 7774 | JF800657 | Pigmented plaque | Luff et al. (2012) |
| | Domestic dog | | Canis familiaris papillomavirus 11 | CPV11 | Chipapillomavirus 1[n] | 7828 | JF800658[nn] | Pigmented plaque | Yuan et al. (unpublished) |
| | Domestic dog | | Canis familiaris papillomavirus 12 | CPV12 | Chipapillomavirus 1[n] | 7890 | JQ754321 | Pigmented plaque | Yuan et al. (unpublished) |
| | Domestic dog (mixed-breed dog) | | Canis familiaris papillomavirus 13 | CPV13 | Taupapillomavirus 2[n] | 8228 | JX141478 | 7826 JQ701802 | Lange et al. (2012a) |
| | Domestic dog (Golden retriever) | | Canis familiaris papillomavirus 14 | CPV14 | Chipapillomavirus 3[n] | 7826 | JQ701802 | Pigmented plaque | Lange et al. (2013b) |
| | Domestic dog | | Canis familiaris papillomavirus 15 | CPV15 | Chipapillomavirus 3[n] | 7776 | JX899359 | NR | Yuan et al. (unpublished) CcrPV1 |
| | Spotted hyena | Crocuta crocuta | Crocuta crocuta papillomavirus 1 | | Lambdapapillomavirus [n] | 8344 | HQ585856 | Oral papilloma | Stevens et al. (2013) |
| | Domestic cat (short-haired Persian cat) | Felis catus | Felis catus papillomavirus 1 | FcaPV1 (FdPV1) | Lambdapapillomavirus 1 | 8300 | AF480454 | Cutaneous papilloma | Tachezy et al. (2002a) |
| | Domestic cat | | Felis catus papillomavirus 2 | FcaPV2 (FdPV2) | Dyothetapapillomavirus 1 | 7899 | EU796884 | Pigmented plaque | Lange et al. (2009b) |
| | Bobcat | Lynx rufus | Lynx rufus papillomavirus 1 | LrPV1 | Lambdapapillomavirus 1 | 8233 | AY904722 | Oral papilloma | Rector et al. (2007) |
| | Asiaticlion | Panthera leo persica | Panthera leo persica papillomavirus 1 | PlpPV1 | Lambdapapillomavirus 1 | 8103 | AY904724 | Oral papilloma | Rector et al. (2007) |
| | Raccoon | Procyon lotor | Procyon lotor papillomavirus 1 | PlPV1 | Lambdapapillomavirus 4 | 8170 | AY763115 | Cutaneous papilloma | Rector et al. (2005b) |

TABLE 1-continued

Overview of genomically characterized non-human papillomaviruses.

| Host species taxonomic order | Host species | Papillomavirus name | Abbreviation (previous) | Classification | # bp | Accession no. | Isolated from | Reference |
|---|---|---|---|---|---|---|---|---|
| | Cougar (Florida panther) | *Puma concolor* | Puma concolor papillomavirus 1 | PcPV1 | Lambdapapillomavirus 1 | 8321 | AY904723 | Oral papilloma | Rector et al. (2007) |
| | Snow leopard | *Uncia uncia* | Uncia uncia papillomavirus 1 | UuPV1 | Lambdapapillomavirus 1 | 8078 | DQ180494 | Papilloma lower lip | Rector et al. (2007) |
| | Polar bear | *Ursus maritimus* | Ursus maritimus papillomavirus 1 | UmPV1 | Omegapapillomavirus 1 | 7582 | EF536349 | Oral papilloma | Stevens et al. (2008a) |
| | California sealion | *Zalophus californianus* | Zalophus californianus papillomavirus 1 | ZcPV1 | Chipapillomavirus" | 7584 | HQ293213 | Skin carcinoma | Hoffman et al. (unpublished) |
| Cetacea | Short-beaked common dolphin | *Delphinus delphis* | Delphinus delphis papillomavirus 1 | DdPV1 | Upsilonpapillomavirus 1 | 7852 | GU117620 | Penile wart | Gottschling et al. (2011) |
| | Harbor porpoise | *Phocoena phocoena* | Phocoena phocoena papillomavirus 1 | PphPV1 | Omikronpapillomavirus 1 | 7596 | GU117621 | Penile papilloma | Gottschling et al. (2011) |
| | | | Phocoena phocoena papillomavirus 2 | PphPV2 | Upsilonpapillomavirus 3 | 7635 | GU117622 | Penile papilloma | Gottschling et al. (2011) |
| | | | Phocoena phocoena papillomavirus 4 | PphPV4 | Dyopipapillomavirus 1 | 7348 | GU117623 | Penile papilloma | Gottschling et al. (2011) |
| | Burmeister's porpoise | *Phocoena spinipinnis* | Phocoena spinipinnis papillomavirus 1 | PsPV1 | Omikronpapillomavirus 1 | 7879 | AJ238373 | Genital papilloma | Van Bressem et al. (2007) |
| | Bottlenose dolphin | *Tursiops truncatus* | papillomavirus 1 | TtPV1 | Upsilonpapillomavirus 1 | 8089 | EU240894 | Penilewart | Rector et al. (2008) |
| | | | papillomavirus 2 | TtPV2 | Upsilonpapillomavirus 2 | 7866 | AY956402 | Genital lesion | Rehtanz et al. (2006) |
| | | | Tursiops truncatus papillomavirus 3 | TtPV3 | Upsilonpapillomavirus 1 | 7915 | EU240895 | Penilewart | Rector et al. (2008) |
| | | | Tursiops truncatus papillomavirus 4 | TtPV4 | Upsilonpapillomavirus 1" | 7792 | JN709469 | Genital lesion | Robles-Sikisaka et al. (2012) |
| | | | Tursiops truncatus papillomavirus 5 | TtPV5 | Omikronpapillomavirus 1" | 7853 | JN709470 | Genital lesion | Robles-Sikisaka et al. (2012) |
| | | | Tursiops truncatus papillomavirus 6 | TtPV6 | Omikronpapillomavirus 1" | 7895 | JN709471 | Genital lesion | Robles-Sikisaka et al. (2012) |
| | | | Tursiops truncatus papillomavirus 7 | TtPV7 | Upsilonpapillomavirus 1" | 7783 | JN709472 | Normal genital mucosa | Robles-Sikisaka et al. (2012) |
| Chiroptera | Common bent-wingbat | *Miniopterus schreibersii* | Miniopterus schreibersii papillomavirus 1 | MscPV1 | unclassified | 7632 | JQ814848 | Pharyngeal swab or anal swab | Wu et al. (2012) |
| | | *Miniopterus schreibersii* | Miniopterus schreibersii papillomavirus 1 TT20F | MscPV1 TT20F | unclassified | 7531 | JQ692938 | Rectalswab | Tse et al. (2012) |
| | Rickett's big-footed Bat | *Myotis ricketti* | Myotis ricketti papillomavirus 1 | MrPV1 | unclassified | 7339 | JQ814847 | Pharyngeal swab or anal swab | Wu et al. (2012) |
| | Egyptian fruit bat | *Rousettus aegyptiacus* | Rousettus aegyptiacus papillomavirus 1 | RaPV1 | Psipapillomavirus 1 | 7970 | DQ366842 | Squamous carcinoma | Rector et al. (2006) |
| Diprotodontia | Brush-tailed bettong | *Bettongia penicillata* | Bettongia penicillata papillomavirus 1 | BpPV1 | Dyokappapapillomavirus 1 | 7743 | GU220391 | Cutaneous papilloma | Bennett et al. (2010) |
| Erinaceomorpha | European hedgehog | *Erinaceus europaeus* | Erinaceus europaeus papillomavirus 1 | EePV1 (EHPV) | Dyoetapapillomavirus 1 | 8256 | FJ379293 | Facial hair follicles | Schulz et al. (2009a) |
| Galliformes | Yellow-necked Frankolin | *Francolinus leucoscepus* | Francolinus leucoscepus papillomavirus 1 | FlPV1 (FLPV) | Dyoepsilonpapillomavirus 1 | 7498 | EU188799 | Healthy skin | Van Doorslaer et al. (2009) |

TABLE 1-continued

Overview of genomically characterized non-human papillomaviruses.

| Host species taxonomic order | Host species | Papillomavirus name | Abbreviation (previous) | Classification | # bp | Accession no. | Isolated from | Reference |
|---|---|---|---|---|---|---|---|---|
| agomorpha | New Zealand white rabbit | *Oryctolagus cuniculus* Oryctolagus cuniculus papillomavirus 1 | OcPV1 (ROPV) | Kappapapillomavirus 1 | 7565 | AF227240 | Oral papilloma | Christensen et al. (2000) |
| | Cottontail rabbit | *Sylvilagus floridanus* Sylvilagus floridanus papillomavirus 1 | SfPV1 (CRPV, SPV) | Kappapapillomavirus 2 | 7868 | K02708 | Cutaneous papilloma | Giri et al. (1985) |
| Passeriformes | Common chaffinch | *Fringilla coelebs* Fringilla coelebs papillomavirus 1 | FcPV1 (FPV) | Etapapillomavirus 1 | 7729 | AY057109 | Cutaneous papilloma | Terai et al. (2002) |
| Perissodactyla | Domestic horse | *Equus ferus caballus* Equus caballus papillomavirus 1 | EcPV1 (EQPV) | Zetapapillomavirus 1 | 7610 | AF498323 | Cutaneous papilloma | Ghim et al. (2004) |
| | | Equus caballus papillomavirus 2 | EcPV2 (EqPV2) | Dyoiotapapillomavirus 1 | 7802 | EU503122$^{nn}$ | Equine genital neoplasia | Scase et al. (unpublished) |
| | | Equus caballus papillomavirus 3 | EcPV3 | Dyorhopapillomavirus 1$^n$ | 7582 | GU384895 | Aural plaque | Lange et al. (2011b) |
| | | Equus caballus papillomavirus 4 | EcPV4 | Dyoiotapapillomavirus 2$^n$ | 7554 | JQ031032 | Vulval and inguinal plaques | (Lange et al. 2013a) |
| | | Equus caballus papillomavirus 5 | EcPV5 | Dyoiotapapillomavirus 3$^n$ | 7519 | JQ031033 | Aural plaque | Lange et al. (2013a) |
| | | Equus caballus papillomavirus 6 | EcPV6 | Dyorhopapillomavirus 1$^n$ | 7551 | JQ965698 | Aural plaque | Lange et al. (2013a) |
| | | Equus caballus papillomavirus 7 | EcPV7 | Dyorhopapillomavirus 1$^n$ | 7619 | JX035935 | Penile mass | Lange et al. (2013a) |
| Primates | Colobus monkey | *Colobus guereza* Colobus guereza papillomavirus 1 | CgPV1 | Alphapapillomavirus 14 | 8060 | GU014532$^{nn}$ | NR | Wood et al. (2011) |
| | | Colobus guereza papillomavirus 2 | CgPV2 | Betapapillomavirus 1 | 7686 | GU014533 | Cutaneous papilloma | Wood et al. 2011 |
| | Cynomolgus macaque | *Macaca fascicularis* Macaca fascicularis papillomavirus 1 | MfPV1 | Betapapillomavirus 1 | 7588 | EF028290 | Cutaneous papilloma | Joh et al. (2009) |
| | | Macaca fascicularis papillomavirus 2 | MfPV2 | Betapapillomavirus 6 | 7632 | GU014531 | Cutaneous papilloma | Wood et al. (2011) |
| | | Macaca fascicularis papillomavirus 3 | MfPV3 (RhPV-d) | Alphapapillomavirus 12 | 7935 | EF558839 | Cervical intra-epithelial neoplasia | Chen et al. (2009) |
| | | Macaca fascicularis papillomavirus 4 | MfPV4 | Alphapapillomavirus 12 | 7950 | EF558841 | Cervical intra-epithelial neoplasia | Chen et al. (2009) |
| | | Macaca fascicularis papillomavirus 5 | MfPV5 (MfPV-a) | Alphapapillomavirus 12 | 7990 | EF558843 | Cervical intra-epithelial neoplasia | Chen et al. (2009) |
| | | Macaca fascicularis papillomavirus 6 | MfPV6 | Alphapapillomavirus 12 | 7943 | EF558840 | NR | Chen et al. (2009) |
| | | Macaca fascicularis papillomavirus 7 | MfPV7 | Alphapapillomavirus 12 | 8063 | EF558838 | NR | Chen et al. (2009) |
| | | Macaca fascicularis papillomavirus 8 | MfPV8 (RhPV-a) | Alphapapillomavirus 12 | 8001 | EF558842 | Cervical intra-epithelial neoplasia | Chen et al. (2009) |
| | | Macaca fascicularis papillomavirus 9 | MfPV9 | Alphapapillomavirus 12 | 7988 | EU490516 | NR | Chen et al. (2009) |
| | | Macaca fascicularis papillomavirus 10 | MfPV10 | Alphapapillomavirus 12 | 7920 | EU490515 | NR | Chen et al. (2009) |
| | | Macaca fascicularis papillomavirus 11 | MfPV11 (RhPV-b) | Alphapapillomavirus 12 | 8014 | GQ227670 | NR | Chen et al. (2009) |

TABLE 1-continued

Overview of genomically characterized non-human papillomaviruses.

| Host species taxonomic order | Host species | Papillomavirus name | Abbreviation (previous) | Classification | # bp | Accession no. | Isolated from | Reference |
|---|---|---|---|---|---|---|---|---|
| | Rhesus macaque | *Macaca mulatta* | Macaca mulatta papillomavirus 1 | MmPV1 (RhPV1) | Alphapapillomavirus 12 | 8028 | M60184 | Mucosal genital carcinoma | Ostrow et al. (1991) |
| | Rickett's big-footed Bat | *Myotis ricketti* | Myotis ricketti papillomavirus 1 | MrPV1 | unclassified | 7339 | JQ814847 | Pharyngeal swab or anal swab | Wu et al. (2012) |
| | Egyptian fruit bat | *Rousettus aegyptiacus* | Rousettus aegyptiacus papillomavirus 1 | RaPV1 | Psipapillomavirus 1 | 7970 | DQ366842 | Squamous carcinoma | Rector et al. (2006) |
| Diprotodontia | Brush-tailed bettong | *Bettongia penicillata* | Bettongia penicillata papillomavirus 1 | BpPV1 | Dyokappapapillomavirus 1 | 7743 | GU220391 | Cutaneous papilloma | Bennett et al. (2010) |
| Erinaceomorpha | European hedgehog | *Erinaceus europaeus* | Erinaceus europaeus papillomavirus 1 | EePV1 (EHPV) | Dyoetapapillomavirus 1 | 8256 | FJ379293 | Facial hair follicles | Schulz et al. (2009a) |
| Galliformes | Yellow-necked Frankolin | *Francolinus leuscepus* | Francolinus leuscepus papillomavirus 1 | FlPV1 (FLPV) | Dyoepsilonpapillomavirus 1 | 7498 | EU188799 | Healthy skin | Van Doorslaer et al. (2009) |
| Lagomorpha | New Zealand white rabbit | *Oryctolagus cuniculus* | Oryctolagus cuniculus papillomavirus 1 | OcPV1 (ROPV) | Kappapapillomavirus 1 | 7565 | AF227240 | Oral papilloma | Christensen et al. (2000) |
| | Cottontail rabbit | *Sylvilagus sfloridanus* | Sylvilagus floridanus papillomavirus 1 | SfPV1 (CRPV, SPV) | Kappapapillomavirus 2 | 7868 | K02708 | Cutaneous papilloma | Giri et al. (1985) |
| Passeriformes | Common chaffinch | *Fringilla coelebs* | Fringilla coelebs papillomavirus 1 | FcPV1 (FPV) | Etapapillomavirus 1 | 7729 | AY057109 | Cutaneous papilloma | Terai et al. (2002) |
| Perissodactyla | Domestic horse | *Equus ferus caballus* | Equus caballus papillomavirus 1 | EcPV1 (EQPV) | Zetapapillomavirus 1 | 7610 | AF498323 | Cutaneous papilloma | Ghim et al. (2004) |
| | | | Equus caballus papillomavirus 2 | EcPV2 (EqPV2) | Dyoiotapapillomavirus 1 | 7802 | EU503122[nn] | Equine genital neoplasia | Scase et al. (unpublished) |
| | | | Equus caballus papillomavirus 3 | EcPV3 | Dyorhopapillomavirus 1[n] | 7582 | GU384895 | Aural plaque | Lange et al. (2011b) |
| | | | Equus caballus papillomavirus 4 | EcPV4 | Dyoiotapapillomavirus 2[n] | 7554 | JQ031032 | Vulval and inguinal plaques | (Lange et al. 2013a) |
| | | | Equus caballus papillomavirus 5 | EcPV5 | Dyoiotapapillomavirus 3[n] | 7519 | JQ031033 | Aural plaque | Lange et al. (2013a) |
| | | | Equus caballus papillomavirus 6 | EcPV6 | Dyorhopapillomavirus 1[n] | 7551 | JQ965698 | Aural plaque | Lange et al. (2013a) |
| | | | Equus caballus papillomavirus 7 | EcPV7 | Dyorhopapillomavirus 1[n] | 7619 | JX035935 | Penile mass | Lange et al. (2013a) |
| Primates | Colobus monkey | *Colobus guereza* | Colobus guereza papillomavirus 1 | CgPV1 | Alphapapillomavirus 14 | 8060 | GU014532[nn] | NR | Wood et al. (2011) |
| | | | Colobus guereza papillomavirus 2 | CgPV2 | Betapapillomavirus 1 | 7686 | GU014533 | Cutaneous papilloma | Wood et al. 2011 |
| | Cynomolgus macaque | *Macaca fascicularis* | Macaca fascicularis papillomavirus 1 | MfPV1 | Betapapillomavirus 1 | 7588 | EF028290 | Cutaneous papilloma | Joh et al. (2009) |
| | | | Macaca fascicularis papillomavirus 2 | MfPV2 | Betapapillomavirus 6 | 7632 | GU014531 | Cutaneous papilloma | Wood et al. (2011) |
| | | | Macaca fascicularis papillomavirus 3 | MfPV3 (RhPV-d) | Alphapapillomavirus 12 | 7935 | EF558839 | Cervical intra-epithelial neoplasia | Chen et al. (2009) |
| | | | Macaca fascicularis papillomavirus 4 | MfPV4 | Alphapapillomavirus 12 | 7950 | EF558841 | Cervical intra-epithelial neoplasia | Chen et al. (2009) |
| | | | Macaca fascicularis papillomavirus 5 | MfPV5 (MfPV-a) | Alphapapillomavirus 12 | 7990 | EF558843 | Cervical intra-epithelial neoplasia | Chen et al. (2009) |

TABLE 1-continued

Overview of genomically characterized non-human papillomaviruses.

| Host species taxonomic order | Host species | Papillomavirus name | Abbreviation (previous) | Classification | # bp | Accession no. | Isolated from | Reference |
|---|---|---|---|---|---|---|---|---|
| | | Macaca fascicularis papillomavirus 6 | MfPV6 | Alphapapillomavirus 12 | 7943 | EF558840 | NR | Chen et al. (2009) |
| | | Macaca fascicularis papillomavirus 7 | MfPV7 | Alphapapillomavirus 12 | 8063 | EF558838 | NR | Chen et al. (2009) |
| | | Macaca fascicularis papillomavirus 8 | MfPV8 (RhPV-a) | Alphapapillomavirus 12 | 8001 | EF558842 | Cervical intra-epithelial neoplasia | Chen et al. (2009) |
| | | Macaca fascicularis papillomavirus 9 | MfPV9 | Alphapapillomavirus 12 | 7988 | EU490516 | NR | Chen et al. (2009) |
| | | Macaca fascicularis papillomavirus 10 | MfPV10 | Alphapapillomavirus 12 | 7920 | EU490515 | NR | Chen et al. (2009) |
| | | Macaca fascicularis papillomavirus 11 | MfPV11 (RhPV-b) | Alphapapillomavirus 12 | 8014 | GQ227670 | NR | Chen et al. (2009) |
| | Rhesus macaque | Macaca mulatta | Macaca mulatta papillomavirus 1 | MmPV1 (RhPV1) | Alphapapillomavirus 12 | 8028 | M60184 | Mucosal genital carcinoma | Ostrow et al. (1991) |
| | Bonobo | Pan paniscus | Pan paniscus papillomavirus 1 | PpPV1 (PCPV) | Alphapapillomavirus 10 | 7902 | X62844 | Oral epithelial | Van Ranst et al. (1991) |
| | Common chimpanzee | Pant roglodytes | Pan troglodytes papillomavirus 1 | PtPV1 (CCPV) | Alphapapillomavirus 10 | 7889 | AF020905 | Oral epithelial hyperplasia | Scinicariello et al. (unpublished) |
| | Hamadryas baboon | Papio hamadryas Anubis | Papio hamadryas papillomavirus type 1 | PhPV1 | Alphapapillomavirus 12$^n$ | 8008 | JF304764 | Cervical samples (CIN1) | Bergin et al. (2013) |
| Psittaciformes | African gray Parrot | Psittacus erithacus | Psittacus erithacus papillomavirus 1 | PePV1 (PePV) | Thetapapillomavirus 1 | 7304 | AF502599 | Cutaneous papilloma | Tachezy et al. (2002b) |
| Rodentia | Woodmouse | Apodemus sylvaticus | Apodemus sylvaticus papillomavirus 1 | AsPV1 | Pipapillomavirus 2$^n$ | 7589 | HQ625440 | Normal skin (ear) | Schulz et al. (2012) |
| | North American porcupine | Erethizon dorsatum | Erethizon dorsatum papillomavirus 1 | EdPV1 | Sigmapapillomavirus 1 | 7428 | AY684126 | Cutaneous papilloma | Rector et al. (2005a) |
| | Natal multimammate mouse | Mastomys natalensis | Mastomys natalensis papillomavirus 1 | MnPV1 (MrPV, MmPV) | Iotapapillomavirus 1 | 7687 | U01834 | Cutaneous papilloma | Tan et al. (1994) |
| | Southern multimammate mouse | Mastomys coucha | Mastomys coucha papillomavirus 2 | McPV2 | Pipapillomavirus 2 | 7522 | DQ664501 | Skin carcinoma | Nafz et al. (2008) |
| | Syrian golden hamster | Mesocricetus auratus | Mesocricetus auratus papillomavirus 1 | MaPV1 (HaOPV) | Pipapillomavirus 1 | 7647 | E15111 | Oral papilloma | Iwasaki et al. (unpublished); patent JP 1998042875-A6 |
| | Eurasian harvest mouse | Micromys minutus | Micromys minutus papillomavirus 1 | MmiPV1 (MmPV1) | Pipapillomavirus 2 | 7393 | DQ269468 | Cutaneous papilloma | Van Doorslaer et al. (2007) |
| | Laboratory mouse | Mus musculus | Mus musculus papillomavirus 1 | MmuPV1 | Pipapillomavirus 2 | 7510 | GU808564 | Cutaneous papilloma | Joh et al. (2011) |
| | Deer mouse | Peromyscus maniculatus | Peromyscus maniculatus papillomavirus 1 | PmPV1 | unclassified | 7704 | JF755418 | Feces | Phan et al. (2011) |
| | Norway rat | Rattus norvegicus | Rattus norvegicus papillomavirus 1 | RnPV1 | Pipapillomavirus 2 | 7378 | GQ180114 | Normal oral mucosa | Schulz et al. (2009b) |
| | | | Rattus norvegicus papillomavirus 2 | RnPV2 | Iotapapillomavirus 2$^n$ | 7724 | HQ625441 | Rectal-smear | Schulz et al. (2012) |
| Sirenia | Florida manatee | Trichechus manatus latirostris | Trichechus manatus latirostris papillomavirus 1 | TmPV1 | Rhopapillomavirus 1 | 7722 | AY609301 | Cutaneous papilloma | Rector et al. (2004a) |
| | | | Trichechus manatus latirostris papillomavirus 2 | TmPV2 | Rhopapillomavirus 1$^n$ | 7855 | JN709473 | NR | Wellehan et al. (unpublished) |

TABLE 1-continued

Overview of genomically characterized non-human papillomaviruses.

| Host species taxonomic order | Host species | Papillomavirus name | Abbreviation (previous) | Classification | # bp | Accession no. | Isolated from | Reference |
|---|---|---|---|---|---|---|---|---|
| Squamata | Diamond python | *Morelia spilota spilota* | Morelia spilota papillomavirus 1 | MsPV1 | Dyomupa-pilloamvirus 1[n] | 7048 | HQ262535[mm] | Pigmented papilloma-like lesion | Lange et al. (2011a) |
| Testudines | Logger-head sea turtle | *Caretta caretta* | Caretta caretta papillomavirus 1 | CcPV1 | Dyozetapa-pilloma-virus 1 | 7020 | EU493092 | Cutaneous papilloma | Herbst et al. (2009) |
| | Green sea turtle | *Chelonia mydas* | Chelonia mydas papillomavirus 1 | CmPV1 | Dyozetapa-pilloma-virus 1 | 6953 | EU493091 | Cutaneous fibro-papilloma | Herbst et al. (2009) |

NR: Not reported.
[n]Classification not yet approved by ICTV.
[mm]A revised sequence is available on the PaVE website(http://pave.niaid.nih.gov).
[mmm]E2 was resequenced and is available under accession number AY8032

TABLE 2

Non-human papilloma viruses and accession numbers.
Non-human papillomaviruses (1) *Bettongia penicillata* papillomavirus 1 (NC_014143)
(2) Canine oral papillomavirus (NC_001619)
(3) *Capra hircus* papillomavirus type 1 (NC_008032)
(4) *Capreolus capreolus* papillomavirus 1 (NC_011051)
(5) *Caretta caretta* papillomavirus 1 (NC_011530)
(6) Cottontail Rabbit Papillomavirus (NC_001541.1)
(7) Cottontail Rabbit Papillomavirus Papillomavirus *sylvilagi* a4 (AJ404003.1)
(8) Cottontail Rabbit (Shope) Papillomavirus (K02708.1)
(9) Cottontail Rabbit Papillomavirus Strain Hershey (JF303889.1)
(10) Cottontail Rabbit Papillomavirus Subtype b (AJ243287.1)
(11) *Crocuta crocuta* papillomavirus 1 (NC_018575)
(12) Deer papillomavirus (NC_001523)
(13) Equine papillomavirus 2 (NC_012123)
(14) *Equus caballus* papillomavirus - 1 (NC_003748)
(15) *Erethizon dorsatum* papillomavirus type 1 (NC_006951)
(16) *Erinaceus europaeus* papillomavirus (NC_011765)
(17) European Elk Papillomavirus (NC_001524.1)
(18) European hedgehog papillomavirus (NC_011765.1)
(19) *Francolinus leucoscepus* papillomavirus 1 (NC_013117)
(20) *Mastomys natalensis* papillomavirus (NC_001605)
(21) Multimammate rat papillomavirus (U01834.1)
(22) *Mus musculus* papillomavirus type1 (NC_014326.1)
(23) Old World harvest mouse Papillomavirus (NC_008682.1)
(24) Ovine papillomavirus type 3 isolate Sar1 (FJ796965)
(25) *Phocoena spinipinnis* papillomavirus (AJ238373)
(26) *Phocoena spinipinnis* papillomavirus (NC_003348)
(27) *Phodopus sungorus* papillomavirus type 1 (HG939559.1)
(28) *Procyon lotor* papillomavirus 1 (PlPV-1) (NC_007150)
(29) *Psittacus erithacus timneh* papillomavirus (NC_003973)
(30) Rabbit Oral papillomavirus (NC_002232)
(31) Rhesus Papillopmavirus Type 1 (M60184.1)
(32) *Rousettus aegyptiacus* papillomavirus type 1 (NC_008298.1)
(33) *Rupicapra rupicapra* papillomavirus 1 (NC_023895)
(34) *Sus scrofa* papillomavirus type 1 (NC_011280)
(35) *Talpa europaea* papillomavirus isolate Bruges/2009/22 (KC460987)
(36) *Trichechus manatus latirostris* papillomavirus 1 (NC_006563)
(37) *Tursiops truncatus* papillomavirus 2 (NC_008184)
(38) *Ursus maritimus* papillomavirus 1 (NC_010739)
(39) Western roedeer papillomavirus 1 isolate CcPV-1 (EF680235.1)
(40) *Puma concolor* Papillomavirus 1 (PcPV1), (AY904723)
(41) *Colobus guereza* (Mantelaffe) papillomavirus type 1 isolate CgPV1 (GU014532.1)
(42) Rhesus papillomavirus type 1b isolate Mac170 (EF591300.1)
(43) *Macaca fascicularis* papillomavirus type 6, isolate Mac39 (EF558840.1)
(44) *Macaca fascicularis* papillomavirus type 11, isolate Mac1637 (GQ227670.1)
(45) Common chimpanzee papillomavirus 1 (AF020905.1)

TABLE 3

Non-human papilloma viruses used in the Examples of the present application.

| Papilloma virus | Abbreviation | GenBank-Nr. |
| --- | --- | --- |
| *Caretta caretta* papillomavirus 1 | CcPV1 | NC_011530 |
| *Colobus guereza* papillomavirus type 1 | CgPV1 | GU014532.1 |
| Common chimpanzee papillomavirus 1 | PtPV1 | AF020905.1 |
| *Crocuta crocuta* papillomavirus 1 | CcrPV1 | NC_018575 |
| *Macaca fascicularis* papillomavirus type 11, isolate Mac1637 | MfPV11 | GQ227670.1 |
| *Macaca fascicularis* papillomavirus type 6, isolate Mac39 | MfPV6 | EF558840.1 |
| *Procyon lotor* papillomavirus 1 | PlPV1 | NC_007150 |
| *Puma concolor* papillomavirus 1 | PcPV1 | AY904723 |
| Rhesus papillomavirus type 1b isolate Mac170 | MmPV1 | EF591300.1 |
| *Rousettus aegyptiacus* papillomavirus type 1 | RaPV1 | NC_008298.1 |

FIGURES

FIG. 1: Western Blots of fractions after purification by ultracentrifugation.

All produced non-human papilloma PsVs were purified by density gradient ultracentrifugation. Subsequently, the collected fractions were separated by SDS-PAGE, blotted onto a nitrocellulose membrane and probed for L1. (A) MfPV6, (B) CcrPV1, (C) CcPV1, (D) CgPV1, (E) MmPV1, (F) MfPV11, (G) PcPV1, (H) PlPV1.

Figure 2:
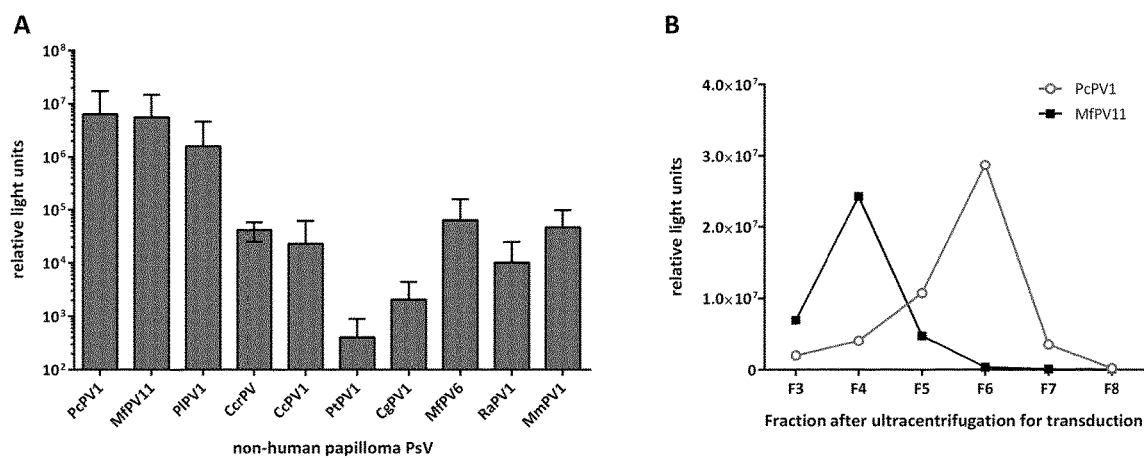
FIG. 2 shows Luciferase assay 72 h after transduction of HEK293TT cells with different non-human papilloma pseudovirions (PsVs). 50.000 HEK293TT cells were transduced by adding 10 µl of fractions 3 to 8 of ultracentrifugation-purified non-human papilloma PsVs. Cell culture supernatant was used for luciferase assay 72 h after transduction. (A) Relative light units (RLU) measured after transduction with at least two independent PsV preparations. Shown are mean RLU values of the fractions yielding the highest transduction of one preparation. (B) RLU for fractions 3-8 after transduction with PcPV1 and MfPV11 PsVs, showing the typical peak of transducing PsVs between OptiPrep fractions 4 and 6.

FIG. 2: Luciferase assay 72 h after transduction of HEK293TT cells with different non-human papilloma pseudovirions (PsVs).

50.000 HEK293TT cells were transduced by adding 10111 of fractions 3 to 8 of ultracentrifugation-purified non-human papilloma PsVs. Cell culture supernatant was used for luciferase assay 72 h after transduction. (A) Relative light units (RLU) measured after transduction with at least two independent PsV preparations. Shown are mean RLU values of the fractions yielding the highest transduction of one preparation. (B) RLU for fractions 3-8 after transduction with PcPV1 and MfPV11 PsVs, showing the typical peak of transducing PsVs between OptiPrep fractions 4 and 6.

Figure 3:
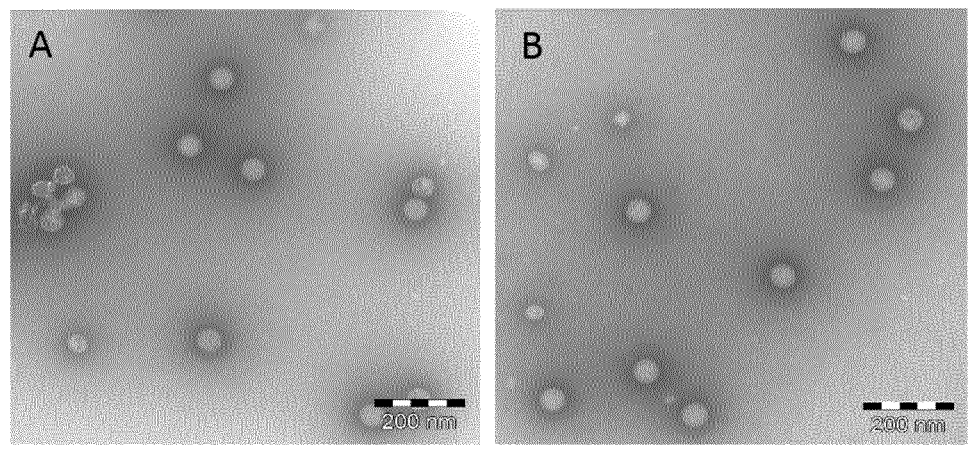
FIG. 3 shows transmission electron microscopy of MfPV11 and PcPV1 VLPs. Purified VLPs were fixed for 24 h at room temperature with formaldehyde, contrasted with phosphotungstic acid and analyzed by transmission electron microscopy. PcPV1 (A), MfPV11 (B).

FIG. 3: Transmission electron microscopy of MfPV11 and PcPV1 VLPs.

Purified VLPs were fixed for 24 h at room temperature with formaldehyde, contrasted with phosphotungstic acid and analyzed by transmission electron microscopy. PcPV1 (A), MfPV11 (B).

Figure 4:
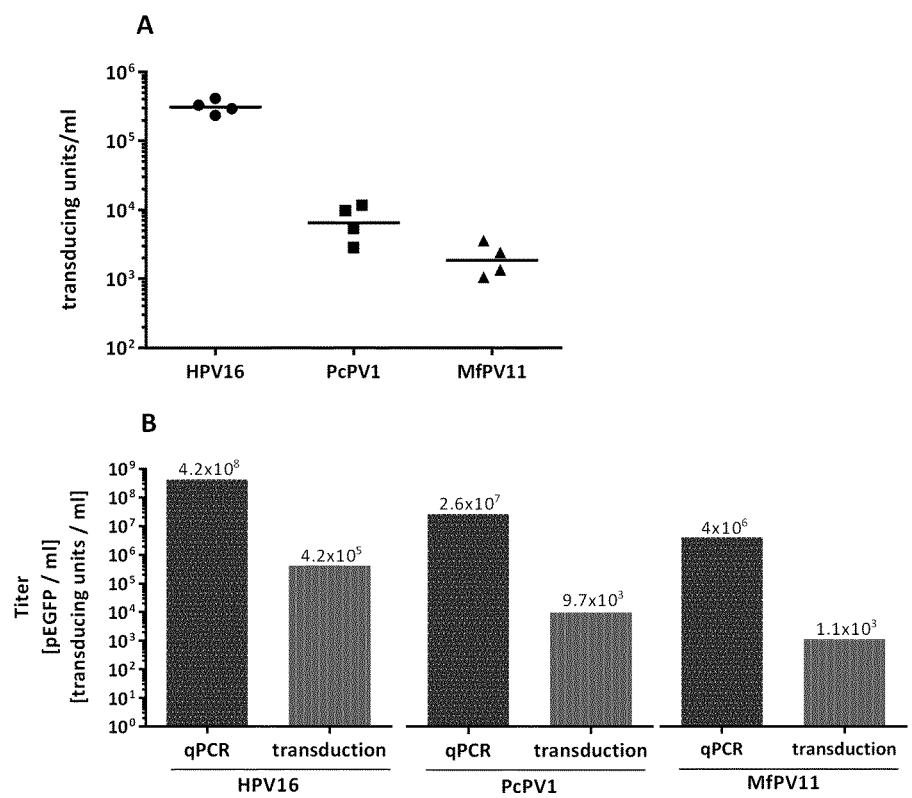
FIG. 4 shows titration of PsVs by transduction of HEK293TT cells. HEK293TT cells were transduced with indicated PsVs carrying pEGFP as reporter plasmid. 72 h after transduction, GFP-positive cells were counted and titer was calculated as transducing units per ml. PsVs. Each data point represents one PsV preparation (A). To compare the amount of transducing units with amount of particles carrying the pEGFP reporter plasmid, DNA was isolated from PsVs and quantified by qPCR. Titer is calculated as pEGFP plasmids per ml (B).

FIG. 4: Titration of PsVs by transduction of HEK293TT cells.

HEK293TT cells were transduced with indicated PsVs carrying pEGFP as reporter plasmid. 72 h after transduction, GFP-positive cells were counted and titer was calculated as transducing units per ml. PsVs. Each data point represents one PsV preparation (A). To compare the amount of transducing units with amount of particles carrying the pEGFP reporter plasmid, DNA was isolated from PsVs and quantified by qPCR. Titer is calculated as pEGFP plasmids per ml (B).

Figure 5:
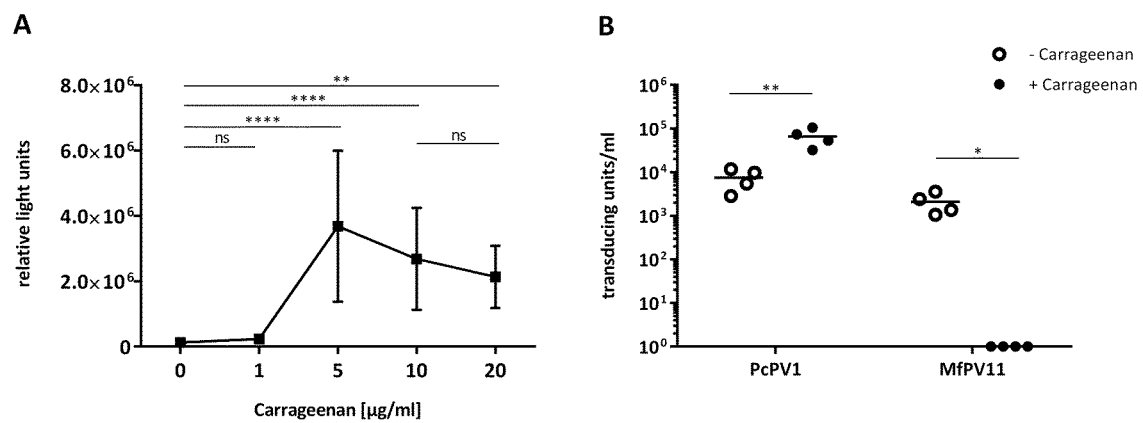
FIG. 5 shows effect of ι-carrageenan on transduction with PcPV1 and MfPV11. Different doses of ι-carrageenan were added to cell culture medium immediately before transduction of HEK293TT cells with PcPV1 PsVs carrying a G.Luc reporter plasmid. Luciferase assay was performed 72 h after transduction. Statistical analysis was performed by 2way ANOVA and Tukey's multiple comparison test (A). Additionally, HEK293TT cells were transduced with PcPV1 and MfPV11 PsVs carrying a pEGFP reporter plasmid with (+) and without (−) addition of 10 µg/ml ι-carrageenan. GFP-positive cells were counted 72 h after transduction and transducing units were calculated. Each data point represents one experiment with one PsV preparation. Statistical analysis was performed using t-test (B).

FIG. 5: Effect of ι-carrageenan on transduction with PcPV1 and MfPV11.

Different doses of ι-carrageenan were added to cell culture medium immediately before transduction of HEK293TT cells with PcPV1 PsVs carrying a G.Luc reporter plasmid. Luciferase assay was performed 72 h after transduction. Statistical analysis was performed by 2way ANOVA and Tukey's multiple comparison test (A). Additionally, HEK293TT cells were transduced with PcPV1 and MfPV11 PsVs carrying a pEGFP reporter plasmid with (+) and without (−) addition of 10 μg/ml ι-carrageenan. GFP-positive cells were counted 72 h after transduction and transducing units were calculated. Each data point represents one experiment with one PsV preparation. Statistical analysis was performed using t-test (B).

Figure 6:
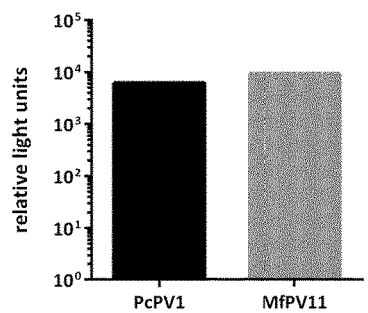
FIG. 6 shows bioluminescence imaging after intramuscular application. 0.24 of PcPV1 and MfPV11 PsVs carrying a firefly luciferase (F.Luc) reporter plasmid were added to 8000 HEK293TT cells for transduction. 72 h later, cells were lysed and lysate was used for F.Luc assay (A). 50 µl of the above analyzed PsV preparations were injected into the left thigh muscle. Bioluminescent imaging was performed approx. 3 h after injection (day 0) to test for any free F.Luc and subsequently in a weekly manner (B).
Figure 6:
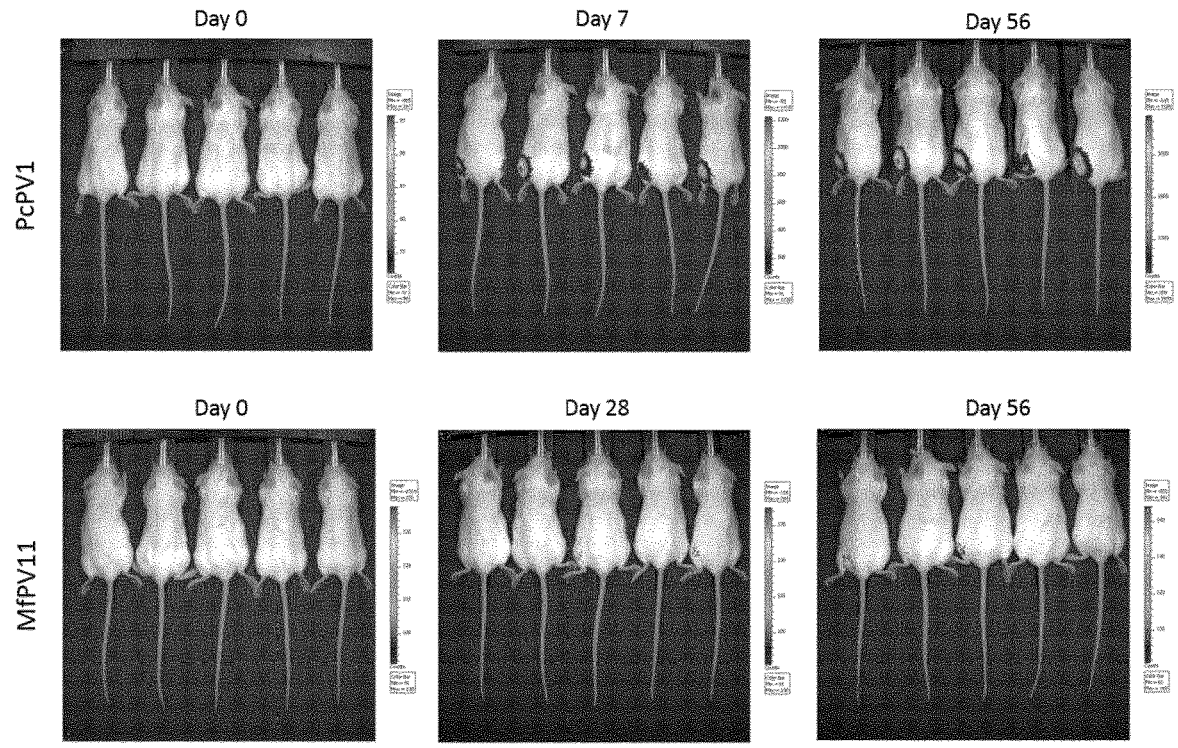

FIG. 6: Bioluminescence imaging after intramuscular application.

0.2 μL of PcPV1 and MfPV11 PsVs carrying a firefly luciferase (F.Luc) reporter plasmid were added to 8000 HEK293TT cells for transduction. 72 h later, cells were lysed and lysate was used for F.Luc assay (A). 50 μl of the above analyzed PsV preparations were injected into the left thigh muscle. Bioluminescent imaging was performed approx. 3 h after injection (day 0) to test for any free F.Luc and subsequently in a weekly manner (B).

EXAMPLES

The invention will be merely illustrated by the following Examples. The said Examples shall, whatsoever, not be construed in a manner limiting the scope of the invention.

Example 1: Materials and Methods

1.1 Cells

HEK293TT cells were maintained in Dulbecco's modified Eagle medium (DMEM), supplemented with 10% fetal bovine serum (Gibco), 100 U/ml Penicillin-Streptomycin (Gibco), GlutaMAX and 25 mM glucose. The 293TT cell line was originally generated by Christopher N. Buck by transfection of 293T cells with linearized pTIH plasmid to achieve an increased expression of the SV40 t antigen (C. B. Buck, D. V. Pastrana, D. R. Lowy, J. T. Schiller, Efficient Intracellular Assembly of Papillomaviral Vectors, Journal of virology. 78, 751-757 (2004), doi:10.1128/JVI.78.2.751-757.2004). For selection, 400 μg/ml of hygromycin (Santa Cruz) were added to cell culture medium.

1.2 Plasmid Construction and Propagation

DNA-sequences coding for papillomavirus capsid proteins L1 and L2 were codon-optimized for expression in human cells and synthesized by GeneArt (Invitrogen, Regensburg, Germany). L1- and L2-sequences were cloned into the multiple cloning site of the mammalian expression vector pcDNA3.1+(Invitrogen), the two sequences being connected by an IRES-sequence. Cloning as well as plasmid propagation was performed in *E. coli* DH5a (New England Biolabs). Plasmids for transfection were prepared using a NucleoBond Plasmid PC500 Maxiprep Kit (Macherey Nagel). As reporter plasmids, pCMV-G.Luc (gaussia luciferase reporter), pCR-Luc3 (firefly luciferase reporter) and pEGFP (GFP reporter) were used.

1.3 Transfection

For non-human papilloma virus-like particle—(VLP) and pseudovirion—(PsV) production, approx. 18 h prior to transfection 6×10$^6$ HEK293TT cells were seeded in a 75 cm2 cell culture flask. Transfection mix was prepared by adding 19 μg of the plasmid coding for papillomavirus L1 and L2 and 19 μg of the reporter plasmid to 1 ml of DMEM. Last, 50 μl of polyethyleneimine (1 mg/ml) was added and the preparation was incubated at room temperature for 10 min. Cell culture media was changed to DMEM supplemented with 1.5% FBS and penicillin/streptomycin before adding the transfection mix. Approximately 16 h after transfection, medium was removed, cells were washed with PBS and complete cell culture medium was added.

1.4 VLP and PsV Harvest

Harvest of VLPs and PsVs was performed approximately 40 hours after transfection following the standard protocol of Buck et Al. (C. Buck, D. Pastrana, D. Lowy, J. Schiller, in Human Papillomaviruses, C. Davy, J. Doorbar, Eds. (Humana Press, 2006), vol. 119, pp. 445-462) with a few modifications. Briefly, cells lysed by adding Triton-X 100 at a final concentration of 0.5% in PBS containing an additional 9.5 mM $MgCl_2$, 10 mM HEPES and 25 mM ammonium sulfate. DNA was digested by addition of Benzonase nuclease (final concentration ≥0.25 U/µp and Plasmid Safe exonuclease (final concentration 0.01 U/µl) for 24 hours. The lysate was chilled on ice, centrifuged at 5,000 g for 10 min at 4° C. After removal of the VLP or PsV containing supernatant, the remaining cell pellet was resuspended in 100 µl of PBS containing an additional 0.8M NaCl. After initial screening experiments, PBS without additional NaCl was used for PcPV1 preparations. The resuspended cells were again centrifuged as above and supernatant was pooled with the supernatant from the first centrifugation step. This resulting clarified lysate was either stored at −80° C. or purified by density gradient ultracentrifugation. Density gradient ultracentrifugation was performed using OptiPrep (Axis-Shield) diluted with PBS+0.8M NaCl to 27%, 33%, and 39%. Gradients were cast by underlayering in a 5 ml tube (Beckman Coulter). Clarified lysate was layered on top and tubes were centrifuged in an SW 55 Ti rotor (Beckman Coulter) at 50,000 rpm (234,000 g) for 3.5 hours at 16° C. After centrifugation, the upper layer up to the transition from 27% to 33% OptiPrep was discarded and subsequently 12 fractions of 250 µl each were collected by pipetting into siliconized 1.5 ml tubes.

Alternatively to ultracentrifugation with OptiPrep, Percoll (GE Healthcare) was used for purification of MfPV11 and HPV16 PsVs. Clarified supernatant was layered on top of 4.5 ml of Percoll diluted to 58.3% with PBS+0.8M NaCl. Tubes were centrifuged in an SW 55 Ti rotor at 30,000 rpm for one hour at 16° C. After centrifugation, supernatant was removed until above the Percoll-pellet about 500 µl still remained, which were collected.

1.5 Transduction with Non-Human Papilloma PsVs 24 h prior to transduction 50,000 HEK293TT cells per well were seeded in a 24-well plate or 8000 HEK293TT cells per well were seeded in a 96-well plate. Non-human papilloma PsVs were added directly to cell culture media. When gaussia luciferase was used as reporter, 20 µl of cell culture supernatant was collected and stored at −20° C. until luciferase-assay was performed to check for free luciferase present in PsV suspension. In experiments with ι-carrageenan (Sigma-Aldrich), ι-carrageenan dissolved in PBS was added to cell culture media at the indicated concentrations immediately prior to addition of PsVs. All transduction experiments were performed in triplicates.

1.6 Quantification of Transduction

Gaussia luciferase assay was performed 72 h after transduction by transferring 20 µl of cell culture supernatant into a black luciferase plate (NUNC). Substrate was prepared by 1:1000 dilution of 2 mM coelenterazine (p.j.k.) in assay buffer (1.1M NaCl, 220 mM $K_2HPO_4/KH_2PO_4$, 0.44 mg/ml BSA, 1.3 mM $NaN_3$, pH 5). Centro $XS^3$ LB 960 Microplate Luminometer (Berthold, Bad Wildbad, Germany) was used to inject 100 µl of the substrate, and measurement of relative light units was performed for 1 sec after a delay of 1 sec after injection for each individual well. Background measurements of cell culture media removed directly after transduction were subtracted from measurements 72 h after transduction. Firefly luciferase assay was performed 72 h after transduction by lysing cells for 2 mins by adding Bright-Glo reagent (Promega) and performing the measurement using a Centro $XS^3$ LB 960 Microplate Luminometer within 5 min after addition of the reagent. When GFP was used as reporter, GFP-positive cells were counted 72 h after transduction and transducing units per ml were calculated.

1.7 Western Blot

20 µl of each fraction was mixed with β-mercaptoethanol-containing loading buffer and proteins were separated by SDS-PAGE. After blotting onto a nitrocellulose membrane, membranes were blocked with 5% non-fat dry milk in PBS-T (PBS containing 0.1% Tween-20) and incubated over night with MD2H11 antibody (from Martin Müller, DKFZ Heidelberg). MD2H11 is directed against a conserved sequence in human papillomavirus capsid protein L1. After incubation with the secondary antibody (polyclonal sheep anti-mouse IgG (H+L), peroxidase-conjugated, Jackson Immuno), the signal was detected by chemiluminescence with ECL substrate (Pierce) using an Intas chemo star system.

1.8 Extraction of DNA from Non-Human Papilloma PsVs and Quantitative PCR

10 µl of pseudovirus samples were subjected to DNA-digest with 4 units DNaseI (NEB) for 60 min at 37° C. to remove any residual DNA that may still be present. DNaseI was heat inactivated for 30 min at 75° C. before DNA was extracted using the Qiamp MinElute Virus Spin Kit (Qiagen). DNA was eluted in 100 µl, of which 5 µl were used per reaction in qPCR. QuantiNova SYBR Green PCR Kit (Qiagen) was used for PCR reaction with the following primers for GFP: 5' ATC CTG GTC GAG CTG GAC GG 3' (forward) (SEQ ID NO: 41) and 5' GAC GTA GCC TTC GGG CAT GG 3' (reverse) (SEQ ID NO: 42). In order to quantify the extracted DNA, a standard curve was created by diluting pEGFP plasmid to contain $3\times10^5$ to 30 copies per reaction.

1.9 Transmission Electron Microscopy

Density gradient ultracentrifugation purified VLPs were fixed for 24 h with 2% formaldehyde in the presence of 0.05M HEPES. Samples were contrasted with phosphotungstic acid before analysis by transmission electron microscopy.

1.10 Mice 9-12 weeks old female BALB/c mice were obtained from in-house breeding. Mice were kept in isolated ventilated cages with unrestricted access to water and rodent chow. All animal experiments were carried out in accordance with the EU Directive 2010/63/EU for animal experiments and were approved by local authorities (No.: TVV 49/15). For in vivo transduction experiments, 50 µl of non-human papilloma PsV suspension was injected into the left thigh muscle under inhalative isoflurane anesthesia.

1.11 Bioluminescence Imaging

200 µl of d-luciferin (15 mg/ml in PBS) were injected intraperitoneally after inhalative isoflurane aesthesia of the mice. 20 min after injection, luminescent images were acquired (1 min exposure, medium binning and f/1) using an IVIS SPECTRUM (Xenogen, Perkin Elmer).

1.12 Statistical Analysis

Statistical analyses were performed using GraphPad Prism6. Differences were regarded as significant for $p<0.05$. Statistically significant differences are indicated as follows: *=$p<0.05$, =$p<0.01$, *=$p<0.001$, ns=not significant.

Example 2: Results

2.1 Analysis of Ten Different Non-Human Papilloma PsVs

Aim of the present study was to explore the abundance of non-human (nh) papillomaviruses for their suitability to be used as gene carriers. Sequences for capsid proteins L1 and L2 of ten different papilloma viruses were identified in NCBI's GenBank database (table 3, abbreviations as published (A. Rector, M. van Ranst, Animal papillomaviruses, Virology. 445, 213-223 (2013), doi:10.1016/j.virol.2013.05.007)). Based on the successful application of HPV PsVs as gene delivery vectors (B. S. Graham et al., Mucosal delivery of human papillomavirus pseudovirus-encapsidated plasmids improves the potency of DNA vaccination, Mucosal immunology. 3, 475-486 (2010), doi:10.1038/mi.2010.31; R. C. Kines et al., Vaccination with Human Papillomavirus Pseudovirus-Encapsidated Plasmids Targeted to Skin Using Microneedles, PLoS ONE. 10, e0120797 (2015), doi:10.1371/journal.pone.0120797), half of the analyzed papilloma viruses belong to the group of alpha-papillomaviruses and naturally infect non-human primates. After synthesis of the codon-optimized DNA-sequences and cloning into pcDNA3.1+ expression vector, VLPs were produced in HEK293TT cells and purified by OptiPrep density gradient ultracentrifugation. First analyses were performed by western blotting of the resulting fractions to check for the expected pattern in which the majority of the purified VLPs would be found in fractions 4-6 due to their size and molecular weight. Eight of the ten non-human papilloma VLPs were detectable by western blot (FIG. 1) in the expected fractions. PtPV and RaPV VLPs were not detectable, but it is possible that the MD2H11 antibody does not bind to the respective L1 proteins. In order to test the functionality of the non-human papilloma PsVs as gene carriers, PsVs carrying pCMV-G.Luc as reporter plasmid were produced and used to transfect HEK293TT cells. 10 µl per fraction after ultracentrifugation were used to transduce 50,000 HEK293TT cells in a 24-well plate. Luciferase assays revealed at least some low level of luciferase expression after transduction for all tested PsVs, with the exception of PtPV. Luciferase expression—as indirect measure for transduction efficiency—differed substantially between the individual papillomavirus types (FIG. 2, A). After several PsV preparations of each non-human papillomavirus type, PcPV1 and MfPV11 proved to be the types that not only lead to the highest transduction rates, but can also be produced very reliably. Thus, in the following experiments PcPV1 and MfPV11 were analyzed further.

2.2 PcPV1 and MfPV11 as Gene Vectors

In order to confirm the formation of papillomavirus capsid structures, PcPV1 and MfPV11 VLPs were produced and purified by OptiPrep ultracentrifugation. Electron microscopic analysis revealed that PcPV1 and MfPV11 indeed form capsids resembling papilloma virions as published previously by others (C. Cerqueira et al., Efficient Production of Papillomavirus Gene Delivery Vectors in Defined In Vitro Reactions, Molecular therapy. Methods & clinical development. 5, 165-179 (2017), doi:10.1016/j.omtm.2017.04.005; Q. Zhao et al., Disassembly and reassembly of human papillomavirus virus-like particles produces more virion-like antibody reactivity, Virology journal. 9, 52 (2012), doi:10.1186/1743-422X-9-52). As transduction with *gaussia* luciferase reporter only provides an indirect measure of transduction efficiency, the inventors repeated transduction experiments with PcPV11 and MfPV11 PsVs carrying pEGFP as reporter to be able to determine transducing units by quantifying GFP-positive cells 72 h after transduction (FIG. 4, A). Additionally, DNA was extracted from PsVs and pEGFP was quantified by qPCR. The titer expression in pEGFP-plasmids per ml is based on the assumption that one plasmid is packaged per PsV (FIG. 4, B). Analysis by qPCR reveals a drastic difference between the amount of PsVs with a packaged reporter plasmid and the amount of transducing units, leading to the conclusion that not the number of produced particles but rather the efficiency of transduction is the limiting factor when using papilloma PsVs for gene transfer. In order to further characterize PcPV1 and MfPV11 PsVs, the inventors tested the ability of ι-carrageenan to inhibit transduction as it had been described before (C. B. Buck et al., Carrageenan is a potent inhibitor of papillomavirus infection, PLoS pathogens. 2, e69 (2006), doi:10.1371/journal.ppat.0020069). While t-carrageenan did indeed prevent transduction with MfPV11 PsVs when it was added to cell culture medium together with the PsVs, the observed effect was just contrary for PcPV1 PsVs (FIG. 5, B). When ι-carrageenan was added to PcPV1 PsVs upon transduction, the expression of the gaussia luciferase reporter protein was significantly increased (FIG. 5, A). This experiment was repeated with pEGFP as reporter plasmid and confirmed that the observed effect is due to a larger number of transduced cells and not to an increased amount of expressed reporter plasmid (FIG. 5, B). A similar ι-carrageenan induced increase in transduction efficiency was also observed for PlPV1, CcrPV1 and MmPV1 PsVs, while transduction with MfPV6 PsVs was inhibited (data not shown).

2.3 MfPV11 and PcPV1 as Gene Carriers In Vivo

It is worth noting that transduction of cell lines with PcPV1 and MfPV11 PsVs has only been moderately effective on any tested cell lines other than HEK293TT in our hands. Therefore, the most pressing question was whether transduction in vivo would be observable. As a simple way to assess gene transfer by non-human papilloma PsVs and subsequent protein expression in vivo, the inventors chose firefly luciferase (F.Luc) as reporter. MfPV11 and PcPV1 PsVs carrying an F.Luc reporter plasmid were produced without purification by ultracentrifugation, 2 µl were used to transduce HEK293TT cells and F.Luc assay was performed 72 h after transduction (FIG. 6, A). PsV preparations were then diluted such that all mice would receive the same amount of transducing units as measured by F.Luc assay in cell culture. 50 µl of PsV suspension containing theoretical $2.5 \times 10^5$ RLU were injected intramuscularly into the left hind leg of female Balb/c mice. Approx. 3 h after application, mice were subjected to bioluminescent imaging in order to check for any free F.Luc that may have been present in the PsV preparation (FIG. 6, B, "Day 0"). Mice were then monitored in a weekly manner by bioluminescent imaging (FIG. 6, B). Mice who had received PcPV1 PsVs showed pronounced expression of F.Luc 7 days after application, while it took 28 days until a weak F.Luc signal was detectable in mice who had received MfPV11 PsVs. The F.Luc signal in the PcPV1 group remained detectable until at least 10 weeks after application, which is when the last bioluminescent imaging was performed. Importantly, mice never showed any signs of adverse reaction or inflammation at the site of non-human papilloma PsV injection.

Example 3: Discussion

Gene-delivery based on viral vectors holds great potential to increase the applicability of genetic vaccines, which are not a competitive alternative to currently approved protein-based vaccines yet. In this study, the inventors show that it is worth exploring the wide range of non-human papilloma viruses for gene delivery, and identified PcPV1 PsVs as efficient delivery vector in vivo. Gene sequences for the capsid proteins L1 and L2 of more than one hundred animal papilloma viruses are available and can be used quite easily to produce pseudovirions, as exemplified for PcPV1 PsVs, in the present application. Since transduction in vitro and in vivo has been shown for PsVs of several human papilloma types belonging to the α-papillomaviruses, the inventors speculated that this genus might provide especially suitable candidates for gene delivery. Interestingly, this did not prove to be true. Of all tested PsVs of non-human α-papillomaviruses (CgPV1, PtPV1, MfPV6, MfPV11, MmPV1) only MfPV11 yielded good transduction rates in vitro. Upon intramuscular injection, however, MfPV11 PsVs showed only very week transduction of the reporter plasmid and subsequent expression in vivo. As the preferred site of entry of different papillomavirus genera can be either cutaneous or mucosal (E.-M. de Villiers, C. Fauquet, T. R. Broker, H.-U. Bernard, H. Zur Hausen, Classification of papillomaviruses, Virology. 324, 17-27 (2004), doi:10.1016/j.virol.2004.03.033), it might be necessary to take this into account when choosing the route of administration. Most HPV types belong to the genus of α-papillomaviruses and therefore infect the mucosa. HPV PsVs have indeed been successfully used for genital transmission in mice (C. Cerqueira et al., Efficient Production of Papillomavirus Gene Delivery Vectors in Defined In Vitro Reactions, Molecular therapy. Methods & clinical development. 5, 165-179 (2017), doi:10.1016/j.omtm.2017.04.005). Although this approach shows promise for a mucosal application of papilloma PsVs as gene vectors, intense pretreatment of the mucosa was necessary, as the intact mouse genital epithelium was found to be quite resistant to infection with HPV16 PsVs (B. S. Graham et al., Mucosal delivery of human papillomavirus pseudovirus-encapsidated plasmids improves the potency of DNA vaccination, Mucosal immunology. 3, 475-486 (2010), doi:10.1038/mi.2010.31). Intramuscular injection uses the well established and commonly accepted route for vaccine administration. The inventors show here that this form of application could be a simple alternative for the administration of papilloma PsVs for gene transfer.

Furthermore, it would be interesting to analyze the use of ι-carrageenan as additional transduction enhancer in vivo. ι-carrageenan has previously been shown to be a potent inhibitor of human papillomavirus infection by preventing the virions from binding to cells (C. B. Buck et al., Carrageenan is a potent inhibitor of papillomavirus infection, PLoS pathogens. 2, e69 (2006), doi:10.1371/journal.ppat.0020069). To the inventors' best knowledge, it has not been reported before that for certain non-human papilloma virus types the effect of ι-carrageenan can be just the opposite, leading to a significantly increased transduction in vitro. Whether this is also the case in vivo remains to be elucidated. Studies analyzing the attachment mechanisms of HPV have shown that on epithelial cells HPV uses heparan sulfate proteoglycans as primary attachment factors. This finding is supported by the fact that infection with HPV can be blocked by heparin or other sulfated polymers like carrageenan. Little is known about a potentially different entry pathway employed by animal papillomaviruses. The mechanism behind t-carrageenan mediated enhancement of transduction that the inventors observe for certain papillomavirus types is therefore unknown at this point. As many non-human papillomaviruses enter the body via the skin it might be worth exploring the cutaneous route for PsV application. In the context of genetic vaccine application, the skin is an attractive target due to the presence of large amounts of Langerhans and dendritic cells.

In conclusion, the inventors show that PcPV1 PsVs—and potentially many more non-human papilloma PsVs—effectively transduce a reporter plasmid in vivo after application into the muscle, leading to a several weeks long expression of a reporter plasmid. The vast amount of known and sequenced non-human papillomaviruses provide great potential to be explored further for the application as gene vectors.

The invention claimed is:

1. A non-human papilloma pseudovirus or virus-like particle comprising at least one codon-optimized nucleic acid sequence encoding a papilloma capsid protein for expression in eukaryotic cells or cell lines, wherein the codon-optimized nucleic acid sequence is as shown in SEQ ID NOS. 1 to 20.

2. The non-human papilloma pseudovirus or virus-like particle of claim 1, wherein the papilloma capsid protein is L1 and/or L2.

3. The non-human papilloma pseudovirus or virus-like particle of claim 1, wherein the papilloma capsid protein is from *Caretta caretta* papillomavirus 1, *Colobus guereza* papillomavirus 1, Common chimpanzee papillomavirus 1,

*Crocuta crocuta* papillomavirus 1, *Macaca fascicularis* papillomavirus type 11, isolate Mac1637, *Macaca fascicularis* papillomavirus type 6, isolate Mac39, *Procyon lotor* papillomavirus 1, *Puma concolor* papillomavirus 1, *Rhesus* papillomavirus type 1b isolate Mac170 or *Rousettus aegyptiacus* papillomavirus type 1.

4. The non-human papilloma pseudovirus or virus-like particle of claim 1, wherein the non-human papilloma virus-like particle is for gene delivery in vitro or in vivo.

5. The non-human papilloma pseudovirus or virus-like particle of claim 1, wherein the non-human papilloma virus-like particle further comprises a targeting peptide.

6. The non-human papilloma pseudovirus or virus-like particle of claim 5, wherein the targeting peptide is capable of directing the non-human papilloma virus-like particle to liver cells, lung cells, heart cells, kidney cells, blood cells, brain cells, gut cells, stem cells, cells of the mucosa of the throat or the nose, or cancer cells.

* * * * *